United States Patent
Kittleson et al.

(10) Patent No.: US 12,325,730 B2
(45) Date of Patent: Jun. 10, 2025

(54) COMPOSITIONS AND METHODS FOR PRODUCING HIGH SECRETED YIELDS OF RECOMBINANT PROTEINS

(71) Applicant: BOLT THREADS, INC., Emeryville, CA (US)

(72) Inventors: Joshua Kittleson, Pleasant Hill, CA (US); Thomas Stevens, San Francisco, CA (US); Rena Hill, Oakland, CA (US); Carlos Gustavo Pesce, San Francisco, CA (US); David N. Breslauer, San Francisco, CA (US); Daniel M. Widmaier, San Francisco, CA (US)

(73) Assignee: BOLT THREADS, INC., Emeryville, CA (US)

(*) Notice: Subject to any disclaimer, the term of this patent is extended or adjusted under 35 U.S.C. 154(b) by 0 days.

(21) Appl. No.: 18/341,669

(22) Filed: Jun. 26, 2023

(65) Prior Publication Data

US 2024/0150416 A1 May 9, 2024

Related U.S. Application Data

(63) Continuation of application No. 17/695,219, filed on Mar. 15, 2022, now Pat. No. 11,725,030, which is a continuation of application No. 15/920,291, filed on Mar. 13, 2018, now Pat. No. 11,306,127, which is a continuation of application No. PCT/US2018/021812, filed on Mar. 9, 2018.

(60) Provisional application No. 62/470,144, filed on Mar. 10, 2017.

(51) Int. Cl.
*C07K 14/435* (2006.01)
*C07K 14/395* (2006.01)
*C12P 21/02* (2006.01)

(52) U.S. Cl.
CPC ...... *C07K 14/43586* (2013.01); *C07K 14/395* (2013.01); *C12P 21/02* (2013.01); *C07K 2319/02* (2013.01)

(58) Field of Classification Search
CPC ............ C07K 14/43586; C07K 14/395; C07K 2319/02; C07K 2319/036; C12P 21/02; C12N 15/815
See application file for complete search history.

(56) References Cited

U.S. PATENT DOCUMENTS

| 9,963,554 | B2 | 5/2018 | Widmaier et al. |
| 11,370,815 | B2 | 6/2022 | Kittleson et al. |
| 2003/0013154 | A1 | 1/2003 | Crawford et al. |
| 2003/0203417 | A1 | 10/2003 | Fowlkes et al. |
| 2003/0233675 | A1 | 12/2003 | Cao et al. |
| 2006/0140965 | A1 | 6/2006 | Cassart et al. |
| 2007/0117186 | A1* | 5/2007 | Sahara ............... C07K 14/4702 536/23.5 |
| 2007/0248967 | A1 | 10/2007 | Ohgiya et al. |
| 2011/0124046 | A1 | 5/2011 | Linger et al. |
| 2011/0165681 | A1 | 7/2011 | Boyden et al. |
| 2013/0259862 | A1 | 10/2013 | Nishimura et al. |
| 2016/0039911 | A1 | 2/2016 | Lesnicki et al. |
| 2016/0222174 | A1 | 8/2016 | Widmaier et al. |
| 2020/0032279 | A1 | 1/2020 | Love et al. |
| 2024/0026331 | A1* | 1/2024 | Celis Luna .... C12Y 304/21026 |

FOREIGN PATENT DOCUMENTS

| EP | 2258855 A1 | 12/2010 |
| JP | 2003-135058 A | 5/2003 |
| JP | 2016-516412 A | 6/2016 |
| WO | 01/77351 A1 | 10/2001 |
| WO | 03/60141 A1 | 7/2003 |
| WO | 2003/103706 A2 | 12/2003 |
| WO | 2005/070962 A1 | 8/2005 |
| WO | 2007/015178 A2 | 2/2007 |
| WO | 2008/052043 A2 | 5/2008 |
| WO | 2010/058057 A1 | 5/2010 |
| WO | 2012/131302 A1 | 10/2012 |
| WO | 2014/066374 A1 | 5/2014 |
| WO | 2015/042164 A2 | 3/2015 |
| WO | 2016/077457 A1 | 5/2016 |
| WO | 2016/149414 A1 | 9/2016 |
| WO | 2016/201369 A1 | 12/2016 |

OTHER PUBLICATIONS

European Application No. 18764854.8 Supplementary European search report and Search Opinion, mailed Dec. 8, 2020.

(Continued)

*Primary Examiner* — Delia M Ramirez
(74) *Attorney, Agent, or Firm* — MARSHALL, GERSTEIN & BORUN LLP

(57) ABSTRACT

The present disclosure relates to methods for producing recombinant proteins, as well as compositions used in and produced by such methods. Specifically, the present disclosure relates to methods for producing high secreted yields of recombinant proteins, and the compositions provided herein include expression constructs, recombinant vectors, and recombinant host cells that comprise polynucleotide sequences encoding proteins operably linked to recombinant secretion signals that comprise the leader peptide of the α-mating factor (αMF) of *Saccharomyces cerevisiae* and a non-αMF signal peptide.

17 Claims, 9 Drawing Sheets

Specification includes a Sequence Listing.

(56) References Cited

OTHER PUBLICATIONS

Extended European Search Report for EP 18 76 4964, dated Dec. 1, 2020, 13 pages.
Fahnestock, R. et al. "Microbial Production of Spider Silk Proteins," Reviews in Molecular Biotechnology, 2000, pp. 105-119, vol. 74.
Fitzgerald, I. et al. "Secretion of a Foreign Protein from Budding Yeasts is Enhanced by Cotranslational Translocation and by Suppression of Vacuolar Targeting," Microbial Cell Factories, 2014, pp. 1-12, vol. 13, No. 125.
Gauthier et al., Increase in Xylanase Production by Streptomyces lividans through Simultaneous Use of the Sec- and Tat-Dependent Protein Export Systems, Appl. Environ. Microbial., 2005, 71, 3085-92.
GenBank accession No. AGW24992; mating factor alpha 1 [*Saccharomyces cerevisiae*], dated by Sep. 25, 2013.
Heiss et al., Multistep processing of the secretion leader of the extracellular protein Epx1 in Pichia pastoris and implications for protein localization, Microbiology, 161:1356-1368 (2015).
International Application No. PCT/US2018/021812, International Preliminary Report on Patentability, mailed Sep. 19, 2019.
International Application No. PCT/US2018/021812, International Search Report and Written Opinion, mailed Aug. 28, 2018.
La Grange et al., Degradation of Xylan to D-Xylose by Recombinant *Saccharomyces cerevisiae* Coexpressing the Aspergillus niger b-Xylosidase (xlnD) and the Trichoderma reesei Xylanase II (xyn2) Genes, Appl. Environ. Microbial., 2001, 67, 5512-19.
La Grange, et al., Expression of a trichoderma reesei beta-xylanase gene (XYN2) in *Saccharomyces cerevisiae*, Appl. Environ. Microbial., 1996, 62, 1036-44.
Liang, et al., Endogenous signal peptides efficiently mediate the secretion of recombinant proteins in Pichia pastoris, Biotechnol. Lett., 2013, 35, 97-105.
Liu, S.-H. et al. "Improved Secretory Production of Glucoamylase in Pichia pastoris by Combination of Genetic Manipulations," Biochemical and Biophysical Research Communications, 2005, pp. 817-824, vol. 326.
Obst, U. et al. "A Modular Toolkit for Generating Pichia pastoris Secretion Libraries," ACS Synthetic Biology, 2017, pp. 1016-1025, vol. 6.
Paifer et al., Efficient Expression and Secretion of Recombinant Alpha Amylase in Pichia pastoris using two different Signal Sequences, Yeast, 1994, 10, 1415-19.
PCT International Search Report and Written Opinion, PCT Application No. PCT/US18/21812, dated Aug. 28, 2018, 20 pages.
PCT International Search Report and Written Opinion, PCT Application No. PCT/US18/21817, dated Aug. 3, 2018, 22 pages.
PCT Invitation to Pay Additional Fees, PCT Application No. PCT/US18/21817, dated Jun. 14, 2018, 2 pages.
Puseenam, et al., Co-expression of Endoxylanase and Endoglucanase in Scheffersomyces stipitis and its Application in Ethanol Production, Appl. Biochem. Biotechnol., 2015, 177, 1690-1700.
Romanos, et al., Foreign gene expression in yeast, Yeast, 1992, 8, 423-88.

* cited by examiner

Figure 3

COMPOSITIONS AND METHODS FOR PRODUCING HIGH SECRETED YIELDS OF RECOMBINANT PROTEINS

CROSS-REFERENCE TO RELATED APPLICATIONS

This application is a continuation of U.S. patent application Ser. No. 17/695,219 (now U.S. Pat. No. 11,725,030), filed Mar. 15, 2022, which is a continuation of U.S. patent application Ser. No. 15/920,291 (now U.S. Pat. No. 11,306,127), filed on Mar. 13, 2018, which is a bypass continuation of and claims priority to International Patent Application No. PCT/US2018/021812, filed Mar. 9, 2018, which claims the benefit of U.S. Provisional Patent Application No. 62/470,144, filed Mar. 10, 2017, the disclosures of which are incorporated herein by reference in their entirety.

SEQUENCE LISTING

The instant application contains a Sequence Listing which has been submitted electronically and is hereby incorporated by reference in its entirety. Said copy, created on Sep. 5, 2023, is named 50008C_SubSeqlisting.xml and is 268,721 bytes in size.

FIELD OF THE INVENTION

The present disclosure relates to methods for producing recombinant proteins, as well as compositions used in and produced by such methods. Specifically, the present disclosure relates to methods for producing high secreted yields of recombinant proteins, as well as expression constructs, recombinant vectors, recombinant host cells, and fermentations used in such methods.

BACKGROUND OF THE INVENTION

Many proteins needed for research, industrial, or therapeutic purposes (e.g., enzymes, vaccines, hormones, and biopharmaceutical proteins) are produced industrially in recombinant host cells. Yeasts, in particular budding yeasts, are favored eukaryotic host organisms for such application. Yeast cells grow rapidly to high cell density in inexpensive media, and comprise cellular machinery for protein folding and post-translational modification (e.g., proteolytic maturation, disulfide bond formation, phosphorylation, O- and N-linked glycosylation). The most commonly used yeast species for production of recombinant proteins include *Saccharomyces cerevisiae, Pichia pastoris, Hansenula polymorpha*, and *Kluyveromyces lactis*. Of these, *Pichia pastoris* is particularly suitable for applications in which recombinant proteins are to be produced at larger (e.g., industrial) scale because it can achieve high density cell growth.

Industrial scale production of recombinant proteins in recombinant host cells is facilitated when the recombinant proteins are secreted from the cells because secreted proteins are readily separated from intact cells, obviating the need for cellular lysis and subsequent separation of the proteins from cellular debris. *Pichia pastoris* is particularly suitable for production of secreted recombinant proteins because it can grow in minimal salt media, which permits isolation of secreted proteins via filtration and chromatography at low conductivity, and because *Pichia pastoris* natively secretes relatively few fermentative products (i.e., small proteins), which further facilitates isolation and purification of secreted recombinant proteins.

Recombinant host cells used for production of secreted recombinant proteins ideally produce large quantities of the recombinant protein, and secrete large fractions of the recombinant protein produced. The former is typically achieved by employing strategies well known in the art, such as, for example, codon optimizing the polynucleotide sequences that are engineered into the recombinant host cells and that encode the recombinant proteins, placing the transcription of such polynucleotide sequences under the control of strong promoters and effective terminators, optimizing translation by introducing suitable ribose binding sites, and increasing the copy number of the polynucleotide sequences in the recombinant host cells (e.g., by engineering host cells that comprise 2 or more copies of a particular polynucleotide sequence). These strategies, however, tend to reach a natural limit in their effectiveness as high copy numbers genetically destabilize the recombinant host cells, and strong promoters yield higher levels of the recombinant proteins than the recombinant host cells can properly fold and/or secrete (Damasceno et al. [2012] Appl Microbiol Biotechnol 93:31-39; Parekh et al. [1995] Protein Expr Purif. 6(4):537-45; Zhu et al. [2009] J Appl Microbiol 107:954-963; Liu et al. [2003] Protein Expr. Purif. 30:262-274). As a result, yields of the recombinant proteins tend to plateau or even decline as unfolded or mis-folded recombinant proteins accumulate inside the recombinant host cells and the recombinant host cells activate molecular stress responses (e.g., the unfolded protein response [UPR] or the ER-associated protein degradation pathway [ERAD] (Hohenblum et al. [2004] Biotechnol Bioeng. 12:367-375; Vassileva et al. [2001] J Biotechnol. 12:21-35; Inan et al. [2006] Biotechnol Bioeng. 12:771-778; Zhu et al. [2009] J Appl Microbiol. 12(3):954-963). Indeed, up-regulation of chaperone proteins or of the main UPR transcriptional regulator (Hac1p) have been shown to reduce the effects of the UPR and to boost recombinant protein yields (Zhang et al. [2006] Biotechnol Prog. 12:1090-1095; Lee et al. [2012] Process Biochem. 12:2300-2305; Valkonen et al. [2003] Appl Environ Microbiol. 12:6979-6986). However, such measures have produced mixed results (Guerfal et al. [2010] Microb Cell Fact. 12:49) and still do not completely eliminate the saturation of the secretory pathways of recombinant host cells (Inan et al. [2006] Biotechnol Bioeng. 12:771-778). The capacity of the secretion machinery of recombinant host cells thus remains a major bottleneck for production of recombinant proteins.

What is needed therefore, are methods and compositions that allow increased expression of desirable recombinant proteins while alleviating the negative impact of overexpression on the recombinant host cells.

BRIEF DESCRIPTION OF THE DRAWINGS

FIGS. 3 through 6 show extracellular (secreted) yields of the recombinant silk-like protein produced by various *Pichia pastoris* recombinant host cells as assayed by ELISA.

Figure 1:
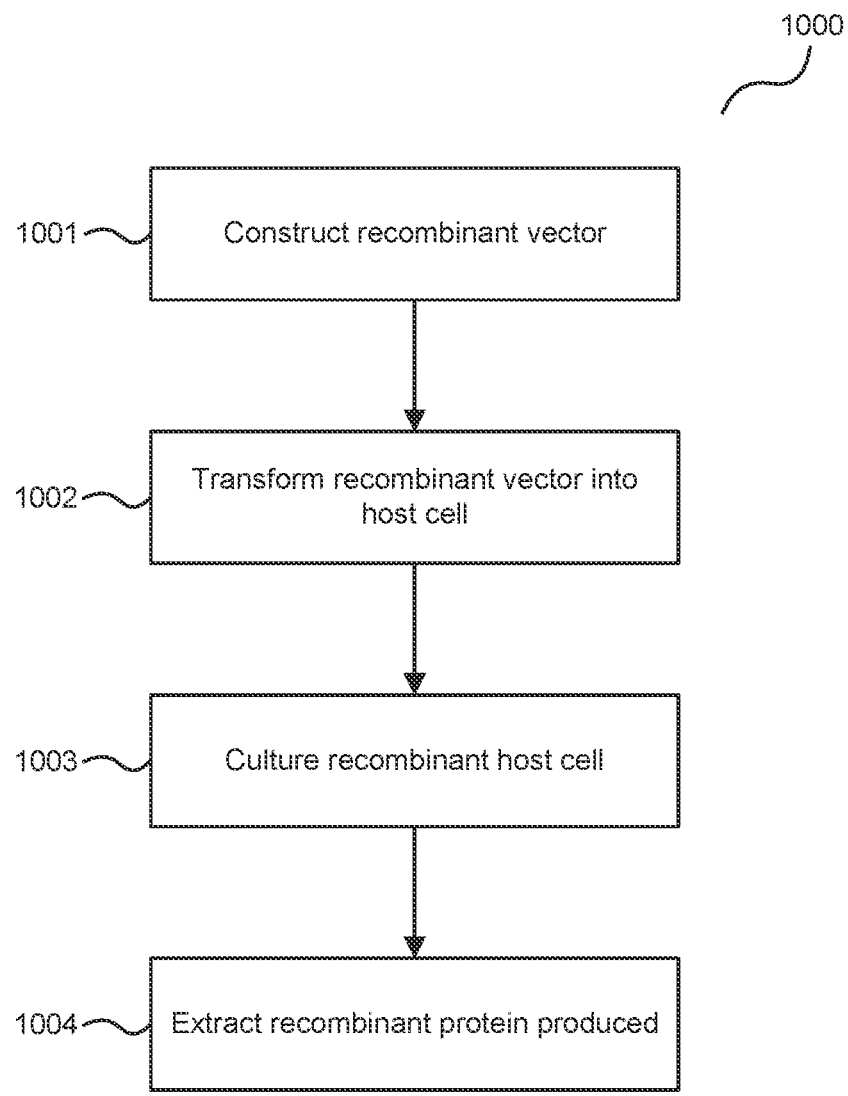
FIG. 1 is a flow diagram of methods for producing high secreted yields of recombinant proteins.

The figures depict various embodiments of the present disclosure for purposes of illustration only. One skilled in the art will readily recognize from the following discussion that alternative embodiments of the structures and methods illustrated herein may be employed without departing from the principles described herein.

DETAILED DESCRIPTION OF THE INVENTION

Definitions

Unless defined otherwise, all technical and scientific terms used herein have the same meaning as is commonly understood by one of ordinary skill in the art to which this disclosure pertains The terms "a" and "an" and "the" and similar referents as used herein refer to both the singular and the plural, unless otherwise indicated herein or clearly contradicted by context.

Amino acids can be referred to by their single-letter codes or by their three-letter codes. The single-letter codes, amino acid names, and three-letter codes are as follows: G—Glycine (Gly), P—Proline (Pro), A—Alanine (Ala), V—Valine (Val), L—Leucine (Leu), I—Isoleucine (Ile), M—Methionine (Met), C—Cysteine (Cys), F—Phenylalanine (Phe), Y—Tyrosine (Tyr), W—Tryptophan (Trp), H—Histidine (His), K—Lysine (Lys), R—Arginine (Arg), Q—Glutamine (Gln), N—Asparagine (Asn), E—Glutamic Acid (Glu), D—Aspartic Acid (Asp), S—Serine (Ser), T—Threonine (Thr).

The term "functional variant" as used herein refers to a protein that differs in composition from a native protein, where the functional properties are preserved to within 10% of the native protein properties. In some embodiments, the difference between the functional variant and the native protein can be in primary amino acid sequence (e.g., one or more amino acids are removed, inserted, or substituted) or post-translation modifications (e.g., glycosylation, phosphorylation). Amino acid insertions may comprise N-terminal and/or C-terminal fusions as well as intra-sequence insertions of single or multiple amino acids. Amino acid substitution includes non-conservative and conservative substitutions, where conservative amino acid substitution tables are well known in the art (see, for example, Creighton (1984) Proteins. W. H. Freeman and Company (Eds)). In some embodiments, the functional variant and the native protein have an at least 80%, at least 85%, at least 90%, at least 95%, or at least 99% amino acid or nucleotide sequence identity.

The terms "identity" or "identical" in the context of nucleic acid or amino acid sequences as used herein refer to the nucleotide or amino acid residues in the two sequences that are the same when the sequences are aligned for maximum correspondence. Depending on the application, the percent "identity" can exist over a region of the sequences being compared (i.e., subsequence [e.g., over a functional domain]) or, alternatively, exist over the full length of the sequences. A "region" is considered to be a continuous stretch of at least 9, 20, 24, 28, 32, or 36 nucleotides, or at least 6 amino acids. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra). One example of an algorithm that is suitable for determining percent sequence identity and sequence similarity is the BLAST algorithm (see, for example, Altschul et al. J. Mol. Biol. 215:403-410; Gish & States. [1993] Nature Genet. 3:266-272; Madden et al. [1996] Meth. Enzymol. 266:131-141; Altschul et al. [1997] Nucleic Acids Res. 25:3389-3402; Zhang 7 Madden. [1997] Genome Res. 7:649-656). Software for performing BLAST analyses is publicly available through the National Center for Biotechnology Information. Such software also can be used to determine the mole percentage of any specified amino acid found within a polypeptide sequence or within a domain of such a sequence. As the person of ordinary skill will recognize such percentages also can be determined through inspection and manual calculation.

The terms "including," "includes," "having," "has," "with," or variants thereof are intended to be inclusive in a manner similar to the term "comprising".

The term "microbe" as used herein refers to a microorganism, and refers to a unicellular organism. As used herein, the term includes all bacteria, all archaea, unicellular protista, unicellular animals, unicellular plants, unicellular fungi, unicellular algae, all protozoa, and all chromista.

The term "native" as used herein refers to what is found in nature in its natural, unmodified state.

The term "operably linked" as used herein refers to polynucleotide or amino acid sequences that are in contiguous linkage with a polynucleotide sequence encoding a protein or a protein, as well as to polynucleotide or amino acid sequences that act in trans or at a distance to a polynucleotide sequence encoding a protein, and that control the transcription, translation, folding, secretion, or other functional aspect of the polynucleotide encoding the protein or the protein.

The terms "optional" or "optionally" mean that the feature or structure may or may not be present, or that an event or circumstance may or may not occur, and that the description includes instances where a particular feature or structure is present and instances where the feature or structure is absent, or instances where the event or circumstance occurs and instances where the event or circumstance does not occur.

The term "protein" as used herein refers to both a polypeptide without functional structure and a polypeptide that folds into an active structure.

The term "recombinant protein" as used herein refers to a protein that is produced in a recombinant host cell, or to a protein that is synthesized from a recombinant nucleic acid.

The term "recombinant host cell" as used herein refers to a host cell that comprises a recombinant nucleic acid.

The term "recombinant nucleic acid" as used herein refers to a nucleic acid that is removed from its naturally occurring environment, or a nucleic acid that is not associated with all or a portion of a nucleic acid abutting or proximal to the nucleic acid when it is found in nature, or a nucleic acid that is operatively linked to a nucleic acid that it is not linked to in nature, or a nucleic acid that does not occur in nature, or a nucleic acid that contains a modification that is not found in that nucleic acid in nature (e.g., insertion, deletion, or point mutation introduced artificially, e.g., by human intervention), or a nucleic acid that is integrated into a chromosome at a heterologous site. The term includes cloned DNA isolates and nucleic acids that comprise chemically-synthesized nucleotide analog.

The term "recombinant secretion signal" as used herein refers to a secretion signal that comprises a non-native combination of a signal peptide and a leader peptide.

The term "recombinant vector" as used herein refers to a nucleic acid molecule capable of transporting another nucleic acid molecule to which it has been linked. The term includes "plasmids", which generally refers to a circular double stranded DNA loop into which additional DNA segments can be ligated, and linear double-stranded molecules, such as those resulting from amplification by the polymerase chain reaction (PCR) or from treatment of a plasmid with a restriction enzyme. Other non-limiting examples of vectors include bacteriophages, cosmids, bacterial artificial chromosomes (BAC), yeast artificial chromosomes (YAC), and viral vectors (i.e., complete or partial viral genomes into which additional DNA segments are ligated). Certain vectors are capable of autonomous replication in a recombinant host cell into which they are introduced (e.g., vectors having an origin of replication that functions in the cell). Other vectors upon introduction can be integrated into the genome of a recombinant host cell, and are thereby replicated along with the cell genome.

The term "secreted recombinant protein" as used herein refers to a recombinant protein that is exported across the cellular membrane and/or cell wall of a recombinant host cell that produces the recombinant protein.

The term "secreted yield" as used herein refers to the amount of secreted protein produced by a host cell based on a fixed amount of carbon supplied to a fermentation comprising the host cell.

The term "total yield" as used herein refers to the amount of total protein produced by a host cell based on a fixed amount of carbon supplied to a fermentation comprising the host cell.

The term "truncated" as used herein refers to a protein sequence that is shorter in length than a native protein. In some embodiments, the truncated protein can be greater than 10%, or greater than 20%, or greater than 30%, or greater than 40%, or greater than 50%, or greater than 60%, or greater than 70%, or greater than 80%, or greater than 90% of the length of the native protein.

Exemplary methods and materials are described below, although methods and materials similar or equivalent to those described herein can also be used in the practice of the present invention and will be apparent to those of skill in the art. All publications and other references mentioned herein are incorporated by reference in their entirety. In case of conflict, the present specification, including definitions, will control. The materials, methods, and examples are illustrative only and not intended to be limiting.

Wherever a range of values is recited, that range includes every value falling within the range, as if written out explicitly, and further includes the values bounding the range. Thus, a range of "from X to Y" includes every value falling between X and Y, and includes X and Y.

Compositions and Methods for Producing High Secreted Yields of Recombinant Proteins Provided herein are expression constructs, recombinant vectors, recombinant host cells, and fermentations, and methods that use such expression constructs, recombinant vectors, recombinant host cells, and fermentations for producing high secreted yields of recombinant proteins.

Advantages of the compositions and methods provided herein include that they provide cost-effective means for producing large quantities of recombinant proteins. The large quantities are obtained using recombinant host cells that secrete recombinant proteins via their secretory pathways. Such secretion of recombinant proteins a) avoids toxicity from intracellular accumulation of recombinant proteins; b) simplifies purification by eliminating cell disruption, separation from cellular components, and protein refolding processes; and c) provides properly folded recombinant proteins with post-translational modifications that may be critical to the activity/function of the recombinant proteins.

Expression Constructs

Provided herein are expression constructs comprising polynucleotide sequences that encode proteins operably linked to recombinant secretion signals provided herein. The recombinant secretion signals are typically operably linked to the N-termini of the proteins.

Recombinant Secretion Signals

To be secreted, a protein has to travel through the intracellular secretory pathway of a cell that produces it. The protein is directed to this pathway, rather than to alternative cellular destinations, via an N-terminal secretion signal. At a minimum, a secretion signal comprises a signal peptide. Signal peptides typically consist of 13 to 36 mostly hydrophobic amino acids flanked by N-terminal basic amino acids and C-terminal polar amino acids. The signal peptide interacts with the signal recognition particle (SRP) or other transport proteins (e.g., SND, GET) that mediates the co- or post-translational translocation of the nascent protein from the cytosol into the lumen of the ER. In the ER, the signal peptide is typically cleaved off and the protein folds and undergoes post-translational modifications. The protein is then delivered from the ER to the Golgi apparatus and then on to secretory vesicles and the cell exterior. In addition to a signal peptide, a subset of nascent proteins natively destined for secretion carry a secretion signal that also comprises a leader peptide. Leader peptides typically consist of hydrophobic amino acids interrupted by charged or polar amino acids. Without wishing to be bound by theory, it is believed that the leader peptide slows down transport and ensures proper folding of the protein, and/or facilitates transport of the protein from the ER to the Golgi apparatus, where the leader peptide is typically cleaved off.

The amount of protein that is secreted from a cell varies significantly between proteins, and is dependent in part on the secretion signal that is operably linked to the protein in its nascent state. A number of secretion signals are known in the art, and some are commonly used for production of secreted recombinant proteins. Prominent among these is the secretion signal of the α-mating factor (αMF) of *Saccharomyces cerevisiae*, which consists of a N-terminal 19-amino-acid signal peptide (also referred to herein as pre-αMF(sc)) followed by a 70-amino-acid leader peptide (also referred to herein as pro-αMF(sc); SEQ ID NO: 1). Inclusion of pro-αMF(sc) in the secretion signal of the αMF of *Saccharomyces cerevisiae* (also referred to herein as pre-αMF (sc)/pro-αMF(sc) (SEQ ID NO: 115) has proven critical for achieving high secreted yields of proteins (see, for example, Fitzgerald & Glick [2014] Microb Cell Fact 28; 13(1):125; Fahnestock et al. [2000] J Biotechnol 74(2):105). Addition of pro-αMF(sc) or functional variants thereof to signal peptides other than pre-αMF(sc) has also been explored as a means of achieving secretion of recombinant proteins, but has shown variable degrees of effectiveness, increasing secretion for certain recombinant proteins in certain recombinant host cells but having no effect or decreasing secretion for other recombinant proteins (Fitzgerald & Glick. [2014] Microb Cell Fact 28; 13(1):125; Liu et al. [2005] Biochem Biophys Res Commun. 326(4):817-24; Obst et al. [2017] ACS Synth Biol. 2017 Mar. 2).

The invention provided herein is based on the identification by the inventors of recombinant secretion signals comprising a functional variant of native pro-αMF(sc) (referred to herein as *pro-αMF(sc)) in combination with certain signal peptides other than pre-αMF(sc) that provide for various secreted yields of recombinant proteins. In some embodiments, the recombinant secretion signals provide larger secreted yields of recombinant proteins than is achieved with the secretion signal of the α-mating factor (αMF) of *Saccharomyces cerevisiae* and/or the recombinant secretion signals in the prior art (e.g., pre-OST1(sc)/pro-αMF(sc); see Fitzgerald & Glick. [2014] Microb Cell Fact 28; 13(1):125; Liu et al. [2005] Biochem Biophys Res Commun. 326(4):817-24; Obst et al. [2017] ACS Synth Biol. 2017 Mar. 2). In other embodiments, the recombinant secretion signals provide smaller secreted yields of recombinant proteins than is achieved with the secretion signal of the α-mating factor (αMF) of *Saccharomyces cerevisiae*.

Accordingly, in various embodiments, the expression constructs provided herein comprise polynucleotide sequences that encode proteins operably linked to recombinant secretion signals that comprise a leader peptide and a signal peptide, wherein the leader peptide is pro-αMF(sc) (SEQ ID NO: 1) or a functional variant therof than has an at least 80% amino acid sequence identity to SEQ ID NO: 1, and wherein the signal peptide does not comprise pre-αMF (sc).

In some embodiments, the functional variant is native pro-αMF(sc) comprising one or two substituted amino acids. In some embodiments, the functional variant is *pro-αMF (SEQ ID NO: 2). In some embodiments, the functional variant has an at least 85%, at least 90%, at least 95%, or at least 99% amino acid sequence identity to SEQ ID NO: 1. In some embodiments, the functional variant is αMF_no_EAEA or αMFΔ or αMFΔ_no_Kex (Obst et al. [2017] ACS Synth Biol. 2017 Mar. 2).

In some embodiments, the signal peptide selected from Table 1 or is a functional variant that has an at least 80% amino acid sequence identity to a signal peptide selected from Table 1. In some embodiments, the functional variant is a signal peptide selected from Table 1 that comprises one or two substituted amino acids. In some such embodiments, the functional variant has an at least 85%, at least 90%, at least 95%, or at least 99% amino acid sequence identity to a signal peptide selected from Table 1. In some embodiments, the signal peptide mediates translocation of the nascent recombinant protein into the ER post-translationally (i.e., protein synthesis precedes translocation such that the nascent recombinant protein is present in the cell cytosol prior to translocating into the ER). In other embodiments, the signal peptide mediates translocation of the nascent recombinant protein into the ER co-translationally (i.e., protein synthesis and translocation into the ER occur simultaneously). An advantage of using a signal peptide that mediates co-translational translocation into the ER is that recombinant proteins prone to rapid folding are prevented from assuming conformations that hinder translocation into the ER and thus secretion.

TABLE 1

Signal Peptides

| Source Gene ID | Species | Name | SEQ ID | Amino Acid Sequence |
|---|---|---|---|---|
| P01239 | Bos taurus | pre-PRL(bt) | 3 | MDSKGSSQKGSRLLLLLVVSNLLLCSA |
| P00698 | Gallus gallus | pre-CLSP(gg) | 4 | MRSLLILVLCFLPLAALG |
| PRC1 | Saccharomyces cerivisae | pre-CPY(sc) | 5 | MKAFTSLLCGLGLSTTLAKA |
| PAS_chr2-2_0084 | Pichia pastoris | pre-PHO8(pp) | 6 | MDSEPLLPNPNDSRKPANWRRIIKYISLTLAWIGIFSYVYIYHGTA |
| PEP4 | Saccharomyces cerevisiae | pre-PEP4(sc) | 7 | MFSLKALLPLALLLVSANQVAA |
| SUC2 | Saccharomyces cerevisiae | pre-SUC2(sc) | 8 | MLLQAFLFLLAGFAAKISA |
| EPX1 | Pichia pastoris | pre-EPX1(pp) | 9 | MKLSTNLILAIAAASAVVSA |
| DAP2 | Saccharomyces cerivisae | pre-DAP2(sc) | 116 | MEGGEEEVERIPDELFDTKKKHLLDKLIRVGIILVLLIWGTVLLLKSI |
| KAR2 | Saccharomyces cerivisae | pre-KAR2(sc) | 117 | MFFNRLSAGKLLVPLSVVLYALFVVILPLQNSFHSSNVLVRGA |

TABLE 1-continued

Signal Peptides

| Source Gene ID | Species | Name | SEQ ID | Amino Acid Sequence |
|---|---|---|---|---|
| NCP1 | Saccharomyces cerivisae | pre-NCP1(sc) | 118 | MPFGIDNTDFTVLAGLVLAVLLYVKR |
| RRT12 | Saccharomyces cerivisae | pre-RRT12(sc) | 119 | MKPQCILISLLVNLAYA |
| PGU1 | Saccharomyces cerivisae | pre-PGU1(sc) | 120 | MISANSLLISTLCAFAIATPLSKR |
| SRL1 | Saccharomyces cerivisae | pre-SRL1(sc) | 121 | MLQSVVFFALLTFASSVSA |
| P08721 | Rattus norvegicus | pre-OSP(m) | 122 | MRLAVVCLCLFGLASCLPVKV |
| PAS_chr2-1_0140 | Pichia pastoris | pre-KAR2(pp) | 123 | MLSLKPSWLTLAALMYAMLLVVVPFAKPVRA |
| PAS_chr1-1_0130 | Pichia pastoris | pre-DSE4(pp) | 124 | MSFSSNVPQLFLLLVLLTNIVSG |
| PAS_chr2-1_0454 | Pichia pastoris | pre-EXG1(pp) | 125 | MNLYLITLLFASLCSA |
| GET1 | Saccharomyces cerivisae | pre-GET1(sc) | 126 | MHWAAAVAIFFIVVTKFLQ |
| PAS_chr1-3_0229 | Pichia pastoris | pre-SCW10(pp) | 127 | MRFSNFLTVSALLTGALG |
| CTS1 | Saccharomyces cerivisae | pre-CTS1(sc) | 128 | MSLLYIILLFTQFLLLPTDA |
| PAS_chr1-3_0251 | Pichia pastoris | pre-OCH1(pp) | 129 | MAKADGSLLYYNPHNPPRRYYFYMAIFAVSVICVLYGPSQQLSS |

Thus, in some embodiments, the expression constructs comprise polynucleotide sequences that encode proteins operably linked to recombinant secretion signal that are selected from Table 2 or are functional variants that have an at least 80% amino acid sequence identity to a recombinant secretions signal selected from Table 2. In some such embodiments, the functional variant has an at least 85%, at least 90%, at least 95%, or are at least 99% amino acid sequence identity to a recombinant secretion signal selected from Table 2.

In some embodiments, the expression constructs provided herein comprise the polynucleotide sequences in multiple (e.g., 2, 3, 4, 5, etc.) copies. In some such embodiments, the polynucleotide sequences are identical. In other such embodiments, at least 2 of the polynucleotide sequences are not identical. In embodiments in which at least 2 of the polynucleotide sequences are not identical, the at least 2 polynucleotide sequences may differ from each other in the proteins and/or the recombinant secretion signals and/or optional tag peptides or polypeptides (see below) they encode.

TABLE 2

Recombinant Secretion Signals

| Name | SEQ ID NO | Amino Acid Sequence |
|---|---|---|
| pre-PRL(bt)/ *pro-αMF(sc) | 10 | MDSKGSSQKGSRLLLLLVVSNLLLCSAAPVNTTTEDETAQIPAEAVIGYSDLEGDFDVAVLPFSNSTNNGLLFINTTIASIAAKEEGVSLEKREAEA |
| pre-CLSP(gg)/ *pro-αMF(sc) | 11 | MRSLLILVLCFLPLAALGAPVNTTTEDETAQIPAEAVIGYSDLEGDFDVAVLPFSNSTNNGLLFINTTIASIAAKEEGVSLEKREAEA |
| pre-CPY(sc)/ *pro-αMF(sc) | 12 | MKAFTSLLCGLGLSTTLAKAAPVNTTTEDETAQIPAEAVIGYSDLEGDFDVAVLPFSNSTNNGLLFINTTIASIAAKEEGVSLEKREAEA |
| pre-PHO8(pp)/ *pro-αMF(sc) | 13 | MDSEPLLPNPNDSRKPANWRRIIKYISLTLAWIGIFSYVYIYHGTAAPVNTTTEDETAQIPAEAVIGYSDLEGDFDVAVLPFSNSTNNGLLFINTTIASIAAKEEGVSLEKREAEA |
| pre-PEP4(sc)/ *pro-αMF(sc) | 14 | MFSLKALLPLALLLVSANQVAAAPVNTTTEDETAQIPAEAVIGYSDLEGDFDVAVLPFSNSTNNGLLFINTTIASIAAKEEGVSLEKREAEA |

TABLE 2-continued

Recombinant Secretion Signals

| Name | SEQ ID NO | Amino Acid Sequence |
|---|---|---|
| pre-SUC2(sc)/<br>*pro-αMF(sc) | 15 | MLLQAFLFLLAGFAAKISAAPVNTTTEDETAQIPAEAVIGYSDLEGDFDVAVLPFSNSTNNGL<br>LFINTTIASIAAKEEGVSLEKREAEA |
| pre-OCH1(pp)/<br>*pro-αMF(sc) | 16 | MAKADGSLLYYNPHNPPRRYYFYMAIFAVSVICVLYGPSQQLSSAPVNTTTEDETAQIPAEA<br>VIGYSDLEGDFDVAVLPFSNSTNNGLLFINTTIASIAAKEEGVSLEKREAEA |
| pre-EPX1(pp)/<br>*pro-αMF(sc) | 130 | MKLSTNLILAIAAASAVVSAAPVNTTTEDETAQIPAEAVIGYSDLEGDFDVAVLPFSNSTNNG<br>LLFINTTIASIAAKEEGVSLEKREAEA |
| pre-DAP2(sc)/<br>*pro-αMF(sc) | 131 | MEGGEEEVERIPDELFDTKKKHLLDKLIRVGIILVLLIWGTVLLLKSIAPVNTTTEDETAQIPA<br>EAVIGYSDLEGDFDVAVLPFSNSTNNGLLFINTTIASIAAKEEGVSLEKREAEA |
| pre-KAR2(sc)/<br>*pro-αMF(sc) | 132 | MFFNRLSAGKLLVPLSVVLYALFVVILPLQNSFHSSNVLVRGAAPVNTTTEDETAQIPAEAVI<br>GYSDLEGDFDVAVLPFSNSTNNGLLFINTTIASIAAKEEGVSLEKREAEA |
| pre-NCP1(sc)/<br>*pro-αMF(sc) | 133 | MPFGIDNTDFTVLAGLVLAVLLYVKRAPVNTTTEDETAQIPAEAVIGYSDLEGDFDVAVLPF<br>SNSTNNGLLFINTTIASIAAKEEGVSLEKREAEA |
| pre-RRT12(sc)/<br>*pro-αMF(sc) | 134 | MKPQCILISLLVNLAYAAPVNTTTEDETAQIPAEAVIGYSDLEGDFDVAVLPFSNSTNNGLLF<br>INTTIASIAAKEEGVSLEKREAEA |
| pre-PGU1(sc)/<br>*pro-αMF(sc) | 135 | MISANSLLISTLCAFAIATPLSKRAPVNTTTEDETAQIPAEAVIGYSDLEGDFDVAVLPFSNST<br>NNGLLFINTTIASIAAKEEGVSLEKREAEA |
| pre-SRL1(sc)/<br>*pro-αMF(sc) | 136 | MLQSVVFFALLTFASSVSAAPVNTTTEDETAQIPAEAVIGYSDLEGDFDVAVLPFSNSTNNGL<br>LFINTTIASIAAKEEGVSLEKREAEA |
| pre-OSP(m)/<br>*pro-αMF(sc) | 137 | MRLAVVCLCLFGLASCLPVKVAPVNTTTEDETAQIPAEAVIGYSDLEGDFDVAVLPFSNSTN<br>NGLLFINTTIASIAAKEEGVSLEKREAEA |
| pre-KAR2(pp)/<br>*pro-αMF(sc) | 138 | MLSLKPSWLTLAALMYAMLLVVVPFAKPVRAAPVNTTTEDETAQIPAEAVIGYSDLEGDFD<br>VAVLPFSNSTNNGLLFINTTIASIAAKEEGVSLEKREAEA |
| pre-DSE4(pp)/<br>*pro-αMF(sc) | 139 | MSFSSNVPQLFLLLVLLTNIVSGAPVNTTTEDETAQIPAEAVIGYSDLEGDFDVAVLPFSNST<br>NNGLLFINTTIASIAAKEEGVSLEKREAEA |
| pre-EXG1(pp)/<br>*pro-αMF(sc) | 140 | MNLYLITLLFASLCSAAPVNTTTEDETAQIPAEAVIGYSDLEGDFDVAVLPFSNSTNNGLLFI<br>NTTIASIAAKEEGVSLEKREAEA |
| pre-GET1(sc)/<br>*pro-αMF(sc) | 141 | MHWAAAVAIFFIVVTKFLQAPVNTTTEDETAQIPAEAVIGYSDLEGDFDVAVLPFSNSTNNG<br>LLFINTTIASIAAKEEGVSLEKREAEA |
| pre-SCW10(pp)/<br>*pro-αMF(sc) | 142 | MRFSNFLTVSALLTGALGAPVNTTTEDETAQIPAEAVIGYSDLEGDFDVAVLPFSNSTNNGL<br>LFINTTIASIAAKEEGVSLEKREAEA |
| pre-CTS1(sc)/<br>*pro-αMF(sc) | 143 | MSLLYIILLFTQFLLLPTDAAPVNTTTEDETAQIPAEAVIGYSDLEGDFDVAVLPFSNSTNNGL<br>LFINTTIASIAAKEEGVSLEKREAEA |

Recombinant Proteins

The proteins encoded by the polynucleotide sequences comprised in the expression constructs provided herein may be any protein.

In some embodiments, the proteins are silk or silk-like proteins. Such silk or silk-like proteins can be selected from a vast array of full-length or truncated native silk proteins or of functional variants of full-length or truncated native silk proteins, or comprise domains of native silk proteins or of functional variants of silk proteins. Putative native silk proteins can be identified by searching sequence databases (e.g., GenBank) for relevant terms (e.g., silkworm silk, spider silk, spidroin, fibroin, MaSp), and translating any nucleotide sequences into amino acid sequences.

In some embodiments, the silk or silk or silk-like proteins are full-length or truncated native silk proteins of a silkworm, or functional variants of full-length or truncated native silk proteins of a silkworm, or comprise domains of native or functional variants of native silk proteins of a silkworm. In some such embodiments, the silkworm is *Bombyx mori*.

In some embodiments, the silk or silk or silk-like proteins are full-length or truncated native silk proteins of a spider, or functional variants of full-length or truncated native silk proteins of a spider, or comprise domains of native or functional variants of native silk proteins of a spider. In some embodiments, the native silk proteins are selected from the group consisting of Major Ampullate spider fibroin (MaSp, also called dragline; e.g., MaSp1, MaSp2) silk proteins, Minor Ampullate spider fibroin (MiSp) silk proteins, Flagelliform spider fibroin (Flag) silk proteins, Aciniform spider fibroin (AcSp) silk proteins, Tubuliform spider fibroin (TuSp) silk proteins, and Pyriform spider fibroin (PySp) silk proteins of orb weaving spiders. In some embodiments, the spider is selected from the group consisting of *Agelenopsis aperta, Aliatypus gulosus, Aphonopelma seemanni, Aptostichus* sp. AS21 7, *Aptostichus* sp. AS220, *Araneus diadematus, Araneus gemmoides, Araneus ventricosus, Argiope amoena, Argiope argentata, Argiope bruennichi, Argiope trifasciata, Atypoides riversi, Avicularia juruensis, Bothriocyrtum californicum, Deinopis Spinosa, Diguetia canities, Dolomedes tenebrosus, Euagrus chiso-* seus, *Euprosthenops australis*, *Gasteracantha mammosa*, *Hypochilus thorelli*, *Kukulcania hibernalis*, *Latrodectus hesperus*, *Megahexura fulva*, *Metepeira grandiosa*, *Nephila antipodiana*, *Nephila clavata*, *Nephila clavipes*, *Nephila madagascariensis*, *Nephila pilipes*, *Nephilengys cruentata*, *Parawixia bistriata*, *Peucetia viridans*, *Plectreurys tristis*, *Poecilotheria regalis*, *Tetragnatha kauaiensis*, or *Uloborus diversus*.

Typically, silk proteins are large proteins (>150 kDa, >1000 amino acids) that can be broken down into 3 domains: an N-terminal non-repetitive domain (NTD), a repeat domain (REP), and a C-terminal non-repetitive domain (CTD). The REP comprises blocks of amino acid sequences ("repeat units") that are at least 12 amino acids long and that are repeated either perfectly ("exact-repeat units") or imperfectly ("quasi-repeat units"), and that can comprise 2 to 10 amino acid long sequence motifs (see FIG. 1). REPs typically make up about 90% of the native spider silk proteins, and assemble into the alanine-rich nano-crystalline (<10 nm) domains (likely made up of alternating beta sheets) and glycine-rich amorphous domains (possibly containing alpha-helices and/or beta-turns) that, without wanting to be bound by theory, are believed to confer strength and flexibility to spider silk fibers, respectively. The lengths and compositions of the REPs are known to vary among different spider silk proteins and across different spider species, giving rise to a broad range of silk fibers with specific properties.

In some embodiments, the silk or silk-like proteins comprise one or more native or functional variants of native REPs (e.g., 1, 2, 3, 4, 5, 6, 7, 8), zero or more native or functional variants of NTDs (e.g., 0, 1), and zero or more native or functional variants of native CTDs (e.g., 0, 1). In some embodiments, the silk or silk-like proteins comprise one or more NTDs that each comprise from 75 to 350 amino acids. In some embodiments, the silk or silk or silk-like proteins comprise one or more CTDs that each comprise from 75 to 350 amino acids. In some embodiments, the silk or silk or silk-like proteins comprise one or more REPs that comprise repeat units that each comprise more than 60, more than 100, more than 150, more than 200, more than 250, more than 300, more than 350, more than 400, more than 450, more than 500, more than 600, more than 700, more than 800, more than 900, more than 1000, more than 1250, more than 1500, more than 1750, or more than 2000; from 60 to 2000, to 1750, to 1500, to 1250, to 1000, to 900, to 800, to 700, to 600, to 500, to 450, to 400, to 350, to 300, to 250, to 200, to 150, or to 100; from 100 to 2000, to 1750, to 1500, to 1250, to 1000, to 900, to 800, to 700, to 600, to 500, to 450, to 400, to 350, to 300, to 250, to 200, or to 150; from 150 to 2000, to 1750, to 1500, to 1250, to 1000, to 900, to 800, to 700, to 600, to 500, to 450, to 400, to 350, to 300, to 250, or to 200; from 200 to 2000, to 1750, to 1500, to 1250, to 1000, to 900, to 800, to 700, to 600, to 500, to 450, to 400, to 350, to 300, or to 250; from 250 to 2000, to 1750, to 1500, to 1250, to 1000, to 900, to 800, to 700, to 600, to 500, to 450, to 400, to 350, or to 300; from 300 to 2000, to 1750, to 1500, to 1250, to 1000, to 900, to 800, to 700, to 600, to 500, to 450, to 400, or to 350; from 350 to 2000, to 1750, to 1500, to 1250, to 1000, to 900, to 800, to 700, to 600, to 500, to 450, or to 400; from 400 to 2000, to 1750, to 1500, to 1250, to 1000, to 900, to 800, to 700, to 600, to 500, or to 450; from 450 to 2000, to 1750, to 1500, to 1250, to 1000, to 900, to 800, to 700, to 600, or to 500; from 500 to 2000, to 1750, to 1500, to 1250, to 1000, to 900, to 800, to 700, or to 600; from 600 to 2000, to 1750, to 1500, to 1250, to 1000, to 900, to 800, or to 700; from 700 to 2000, to 1750, to 1500, to 1250, to 1000, to 900, or to 800; from 800 to 2000, to 1750, to 1500, to 1250, to 1000, or to 900; from 900 to 2000, to 1750, to 1500, to 1250, or to 1000; from 1000 to 2000, to 1750, to 1500, or to 1250; from 1250 to 2000, to 1750, or to 1500; from 1500 to 2000, or to 1750; or from 1750 to 2000 amino acid residues.

In some embodiments, the silk or silk or silk-like proteins comprise greater than 2, greater than 4, greater than 6, greater than 8, greater than 10, greater than 12, greater than 14, greater than 16, greater than 18, greater than 20, greater than 22, greater than 24, greater than 26, greater than 28, or greater than 30; from 2 to 30, to 28, to 26, to 24, to 22, to 20, to 18, to 16, to 14, to 12, to 10, to 8, to 6, or to 4; from 4 to 30, to 28, to 26, to 24, to 22, to 20, to 18, to 16, to 14, to 12, to 10, to 8, or to 6; from 6 to 30, to 28, to 26, to 24, to 22, to 20, to 18, to 16, to 14, to 12, to 10, or to 8; from 8 to 30, to 28, to 26, to 24, to 22, to 20, to 18, to 16, to 14, to 12, or to 10; from 10 to 30, to 28, to 26, to 24, to 22, to 20, to 18, to 16, to 14, or to 12; from 12 to 30, to 28, to 26, to 24, to 22, to 20, to 18, to 16, or to 14; from 14 to 30, to 28, to 26, to 24, to 22, to 20, to 18, or to 16; from 16 to 30, to 28, to 26, to 24, to 22, to 20, or to 18; from 18 to 30, to 28, to 26, to 24, to 22, or to 20; from 20 to 30, to 28, to 26, to 24, or to 22; from 22 to 30, to 28, to 26, or to 24; from 24 to 30, to 28, or to 26; from 26 to 30, or to 28; from 28 to 30 exact-repeat and/or quasi-repeat units that each have molecular weights of greater than 5 kDa, greater than 10 kDa, greater than 20 kDa, greater than 30 kDa, greater than 40 kDa, greater than 50 kDa, greater than 60 kDa, greater than 70 kDa, greater than 80 kDa, or greater than 90 kDa; from 5 kDa to 100 kDa, to 90 kDa, to 80 kDa, to 70 kDa, to 60 kDa, to 50 kDa, to 40 kDa, to 30 kDa, to 20 kDa, or to 10 kDa; from 10 kDa to 100 kDa, to 90 kDa, to 80 kDa, to 70 kDa, to 60 kDa, to 50 kDa, to 40 kDa, to 30 kDa, or to 20 kDa; from 20 kDa to 100 kDa, to 90 kDa, to 80 kDa, to 70 kDa, to 60 kDa, to 50 kDa, to 40 kDa, or to 30 kDa; from 30 kDa to 100 kDa, to 90 kDa, to 80 kDa, to 70 kDa, to 60 kDa, to 50 kDa, or to 40 kDa; from 40 kDa to 100 kDa, to 90 kDa, to 80 kDa, to 70 kDa, to 60 kDa, or to 50 kDa; from 50 kDa to 100 kDa, to 90 kDa, to 80 kDa, to 70 kDa, or to 60 kDa; from 60 kDa to 100 kDa, to 90 kDa, to 80 kDa, or to 70 kDa; from 70 kDa to 100 kDa, to 90 kDa, or to 80 kDa; from 80 kDa to 100 kDa, or to 90 kDa; or from 90 kDa to 100 kDa. In some such embodiments, the order of the 2 or more exact-repeat or quasi-repeat units within the silk or silk or silk-like proteins is not native.

In some embodiments, the silk or silk or silk-like proteins comprise more than 1, more than 2, more than 4, more than 6, more than 8, more than 10, more than 15, more than 20, or more than 25; from 1 to 30, to 25, to 20, to 15, to 10, to 8, to 6, to 4, or to 2; from 2 to 30, to 25, to 20, to 15, to 10, to 8, to 6, or to 4; from 4 to 30, to 25, to 20, to 15, to 10, to 8, or to 6; from 6 to 30, to 25, to 20, to 15, to 10, or to 8; from 8 to 30, to 25, to 20, to 15, or to 10; from 10 to 30, to 25, to 20, or to 15; from 15 to 30, to 25, or to 20; from 20 to 30, or to 25; or from 25 to 30 exact-repeat and/or quasi-repeat units that are glycine-rich. In some such embodiments, one or more of the glycine-rich exact-repeat and/or quasi-repeat units comprise more than 4, more than 6, more than 8, more than 10, more than 12, more than 15, more than 18, more than 20, more than 25, more than 30, more than 40, more than 50, more than 60, more than 70, more than 80, more than 90, more than 100, or more than 150; from 4 to 200, to 150, to 100, to 90, to 80, to 70, to 60, to 50, to 40, to 30, to 25, to 20, to 18, to 15, to 12, to 10, to 8, or to 6; from 6 to 200, to 150, to 100, to 90, to 80, to 70, to 60, to 50, to 40, to 30, to 25, to 20, to 18, to 15, to 12, to 10, or to 8; from 8 to 200, to 150, to 100, to 90, to 80, to 70, to 60, to 50, to 40, to 30, to 25, to 20, to 18, to 15, to 12, or to 10; from 10 to 200, to 150, to 100, to 90, to 80, to 70, to 60, to 50, to 40, to 30, to 25, to 20, to 18, to 15, or to 12; from 12 to 200, to 150, to 100, to 90, to 80, to 70, to 60, to 50, to 40, to 30, to 25, to 20, to 18, or to 15; from 15 to 200, to 150, to 100, to 90, to 80, to 70, to 60, to 50, to 40, to 30, to 25, to 20, or to 18; from 18 to 200, to 150, to 100, to 90, to 80, to 70, to 60, to 50, to 40, to 30, to 25, or to 20; from 20 to 200, to 150, to 100, to 90, to 80, to 70, to 60, to 50, to 40, to 30, or to 25; from 25 to 200, to 150, to 100, to 90, to 80, to 70, to 60, to 50, to 40, or to 30; from 30 to 200, to 150, to 100, to 90, to 80, to 70, to 60, to 50, or to 40; from 40 to 200, to 150, to 100, to 90, to 80, to 70, to 60, or to 50; from 50 to 200, to 150, to 100, to 90, to 80, to 70, or to 60; from 60 to 200, to 150, to 100, to 90, to 80, or to 70; from 70 to 200, to 150, to 100, to 90, or to 80; from 80 to 200, to 150, to 100, or to 90; from 90 to 200, to 150, or to 100; from 100 to 200, or to 150; or from 150 to 200 consecutive amino acids that are more than 30%, more than 40%, more than 45%, more than 50%, more than 55%, more than 60%, more than 70%, or more than 80%; from 30% to 100%, to 90%, to 80%, to 70%, to 60%, to 55%, to 50%, to 45%, or to 40%; from 40% to 100%, to 90%, to 80%, to 70%, to 60%, to 55%, to 50%, or to 45%; from 45% to 100%, to 90%, to 80%, to 70%, to 60%, to 55%, or to 50%; from 50% to 100%, to 90%, to 80%, to 70%, to 60%, or to 55%; from 55% to 100%, to 90%, to 80%, to 70%, or to 60%; from 60% to 100%, to 90%, to 80%, or to 70%; from 70% to 100%, to 90%, or to 80%; from 80% to 100%, or to 90%; or from 90% to 100% glycine.

In some embodiments, the silk or silk or silk-like proteins comprise more than 1, more than 2, more than 4, more than 6, more than 8, more than 10, more than 15, more than 20, or more than 25; from 1 to 30, to 25, to 20, to 15, to 10, to 8, to 6, to 4, or to 2; from 2 to 30, to 25, to 20, to 15, to 10, to 8, to 6, or to 4; from 4 to 30, to 25, to 20, to 15, to 10, to 8, or to 6; from 6 to 30, to 25, to 20, to 15, to 10, or to 8; from 8 to 30, to 25, to 20, to 15, or to 10; from 10 to 30, to 25, to 20, or to 15; from 15 to 30, to 25, or to 20; from 20 to 30, or to 25; or from 25 to 30 exact-repeat and/or quasi-repeat units that are alanine-rich. In some such embodiments, one or more of the alanine-rich exact-repeat and/or quasi-repeat units comprise more than 4, more than 6, more than 8, more than 10, more than 12, more than 15, or more than 18; from 4 to 20, to 18, to 15, to 12, to 10, to 8, or to 6; from 6 to 20, to 18, to 15, to 12, to 10, or to 8; from 8 to 20, to 18, to 15, to 12, or to 10; from 10 to 18, to 15, or to 12; from 12 to 20, to 18, or to 15; from 15 to 20, or to 18; or from 18 to 20; consecutive amino acids that are more than 70%, more than 75%, more than 80%, more than 85%, or more than 90%; from 70% to 100%, to 90%, to 85%, to 80%, or to 75%; from 75% to 100%, to 90%, to 85%, or to 80%; from 80% to 100%, to 90%, or to 85%; from 85% to 100%, or to 90%; or from 90% to 100% alanine.

In some embodiments, the silk or silk or silk-like proteins comprise one or more glycine-rich exact-repeat and/or quasi-repeat units that are from 20 to 100 amino acids long and that are concatenated with poly-alanine-rich regions that are from 4 to 20 amino acids long. In some embodiments, the silk or silk or silk-like proteins comprise 5-25% poly-alanine regions (from 4 to 20 poly-alanine residues). In some embodiments, the silk or silk or silk-like proteins comprise 25-50% glycine. In some embodiments, the silk or silk or silk-like proteins comprise 15-35% GGX, where X is any amino acid. In some embodiments, the silk or silk or silk-like proteins comprise 15-60% GPG. In some embodiments, the silk or silk or silk-like proteins comprise 10-40% alanine. In some embodiments, the silk or silk or silk-like proteins comprise 0-20% proline. In some embodiments, the silk or silk or silk-like proteins comprise 10-50% beta-turns. In some embodiments, the silk or silk or silk-like proteins comprise 10-50% alpha-helix composition. In some embodiments, all of these compositional ranges apply to the same silk or silk or silk-like protein. In some embodiments, 2 or more of these compositional ranges apply to the same silk or silk or silk-like protein.

In some embodiments, the structure of the silk or silk or silk-like proteins form beta-sheet structures, beta-turn structures, or alpha-helix structures. In some embodiments, the secondary, tertiary, and quaternary structures of the silk or silk or silk-like proteins have nanocrystalline beta-sheet regions, amorphous beta-turn regions, amorphous alpha helix regions, randomly spatially distributed nanocrystalline regions embedded in a non-crystalline matrix, or randomly oriented nanocrystalline regions embedded in a non-crystalline matrix. In some embodiments, the silk or silk or silk-like proteins are highly crystalline. In other embodiments, the silk or silk or silk-like proteins are highly amorphous. In some embodiments, the silk or silk or silk-like proteins comprise both crystalline and amorphous regions. In some embodiments, the silk or silk or silk-like proteins comprise from 10% to 40% crystalline material by volume.

In some embodiments, the silk or silk or silk-like proteins comprise one or more exact-repeat or quasi-repeat units that have at least 80%, at least 85%, at least 90%, at least 95%, or at least 99% amino acid sequence identity to a repeat unit of a native spider silk protein. In some embodiments, the silk or silk or silk-like proteins comprise one or more exact-repeat or quasi-repeat units that have an at least 80%, at least 85%, at least 90%, at least 95%, or at least 99% amino acid sequence identity to a repeat unit of a native spider dragline silk protein. In some embodiments, the silk or silk or silk-like proteins comprise one or more exact-repeat or quasi-repeat units that have at least 80%, at least 85%, at least 90%, at least 95%, or at least 99% amino acid sequence identity to a repeat unit of a native MA dragline silk protein. In some embodiments, the silk or silk or silk-like proteins comprise one or more exact-repeat or quasi-repeat units that have at least 80%, at least 85%, at least 90%, at least 95%, or at least 99% amino acid sequence identity to a repeat unit of a native MaSp2 dragline silk protein.

In some embodiments, the silk or silk or silk-like proteins comprise one or more quasi-repeat units, wherein the amino acid sequence of each quasi-repeat unit is described by Equation 1, wherein the amino acid sequence of X1 (termed a "motif") is described by Equation 2 and can vary randomly within each quasi-repeat unit. The sequence $[\text{GPG-X1}]_{n1}$ (SEQ ID NO: 147) is referred to as "first region", and is glycine-rich. The sequence $(A)_{n2}$ (SEQ ID NO: 148) is referred to as "second region", and is alanine-rich. In some embodiments, the value of n1 is any one of 4, 5, 6, 7, or 8. In some embodiments, the value of n2 is any one of 6, 7, 8, 9, 10, 11, 12, 13, 14, 15, 16, 17, 18, 19, or 20. In some embodiments, the value of n3 is any one from 2 to 20. In some embodiments, the silk or silk or silk-like proteins comprise one or more of quasi-repeat units that have at least 80%, 90%, 95%, or 99% sequence identity to a quasi-repeat unit described by Equations 1 and 2.

$$\{\text{GGY-}[\text{GPG-X1}]_{n1}\text{-GPS-}(A)_{n2}\}_{n3} \text{ (SEQ ID NO: 149)} \quad \text{(Equation 1)}$$

X1=SGGQQ (SEQ ID NO: 150) or GAGQQ (SEQ
ID NO: 151) or GQGPY (SEQ ID NO: 152) or
AGQQ (SEQ ID NO: 153) or SQ    (Equation 2)

In some embodiments, the silk or silk or silk-like proteins comprise quasi-repeat units as described by Equation 1 and Equation 2, wherein n1 is 4 or 5 for at least half of the quasi-repeat units. In some embodiments, the silk or silk or silk-like proteins comprise quasi-repeat units as described by Equation 1 and Equation 2, wherein n2 is from 5 to 8 for at least half of the quasi-repeat units.

The term "short quasi-repeat unit" as used herein refers to a repeat unit in which n1 is 4 or 5 (as shown in Equation 1). The term "long quasi-repeat unit" as used herein refers to a repeat in which n1 is 6, 7, or 8 (as shown in Equation 1). In some embodiments, n1 is from 4 to 5 for at least half of the quasi-repeat units. In some embodiments, n2 is from 5 to 8 for at least half of the quasi-repeat units. In some embodiments, the silk or silk or silk-like proteins comprise 3 "long quasi-repeat units" followed by 3 "short quasi-repeat units". In some embodiments, the silk or silk or silk-like proteins comprise quasi-repeat units that do not have the same $X_1$ motifs more than twice in a row, or more than 2 times, in a single quasi-repeat. In some embodiments, the silk or silk or silk-like proteins comprise quasi-repeat units that comprise the same $X_1$ motifs in the same location. In some embodiments, the silk or silk or silk-like proteins comprise quasi-repeat units that comprise the same Equation 2 sequence in the same location. In some embodiments, the silk or silk or silk-like proteins comprise quasi-repeat units wherein no more than 3 quasi-repeat units out of 6 share the same $X_1$.

In some embodiments, the silk or silk or silk-like proteins comprise Xqr quasi-repeat units, wherein $$Xqr = Xsqr + Xlqr \quad \text{(Equation 3)},$$

wherein Xqr is a number from 2 to 20; Xsqr is the number of short quasi-repeats, and a number from 1 to (Xqr-1); and Xlqr is the number of long quasi-repeats, and a number from 1 to (Xqr-1). In some embodiments, $X_{qr}$ is a number from 2 to 20. Non-limiting examples of amino acid sequences of repeat units are given in Table 3.

TABLE 3

Exemplary Repeat Units of Silk or Silk-Like Proteins

| SEQ ID NO | Amino Acid Sequence |
|---|---|
| 17 | GGYGPGAGQQGPGSGGQQGPGGQGPYGSGQQGPGGAGQQGPGGQGPYGPGAAAAAAAAGGYGPGAGQQGPGGAGQQGP<br>GSQGPGGQGPYGPGAGQQGPGSQGPGSGGQQGPGGQGPYGPSAAAAAAAAGGYGPGAGQRSQGPGGQGPYGPGAGQQGPG<br>SQGPGSGGQQGPGGQGPYGPSAAAAAAAAGGYGPGAGQQGPGSQGPGSGGQQGPGGQGPYGPGAAAAAAAVGGYGPGAGQ<br>QGPGSQGPGSGGQQGPGGQGPYGPSAAAAAAAAGGYGPGAGQQGPGSQGPGSGGQQGPGGQGPYGPSAAAAAAAA |
| 18 | GGGQGGRGGFGGLGSQGAGGAGQGGAGAAAAAAAAGGDGGSGLGGYGAGRGHGVGLGGAGGAGAASAAAAAGGQGGRGG<br>FGGLGSQGAGGAGQGGAGAAAAAAAAGGDGGSGLGGYGAGRGHGAGLGGAGGAGAASAAAAAGGQGGRGGFGGLGSQGS<br>GGAGQGGSGAAAAAAAAGGDGGSGLGGYGAGRGYGAGLGGAGGAGAASAAAAAGGQGGRGGFGGLGSQGAGGAGQGGS<br>GAAAAAAAAVADGGSGLGGYGAGRGYGAGLGGAGGAGAASAAAAT |
| 19 | GSAPQGAGGPAPQGPSQQGPVSQGPYGPGAAAAAAAAGGYGPGAGQQGPGSQGPGSGGQQGPGSQGPGSGGQQGPGGQGPY<br>GPSAAAAAAAAGGYGPGAGQQGPGSQGPGSGGQQGPGGQGPYGPGAAAAAAAVGGYGPGAGQQGPGSQGPGSGGQQGPG<br>GQGPYGPSAAAAAAAAGGYGPGAGQQGPGSQGPGSGGQQGPGGQGPYGPSAAAAAAAAGGYGPGAGQQGPGSGGQQGPGG<br>QGPYGSGQQGPGGAGQQGPGGQGPYGPGAAAAAAAA |
| 20 | GGYGPGAGQQGPGSGGQQGPGGQGPYGSGQQGPGGAGQQGPGGQGPYGPGAAAAAAAAGGYGPGAGQQGPGGAGQQGP<br>GSQGPGGQGPYGPGAGQQGPGSQGPGSGGQQGPGGQGPYGPSAAAAAAAAGGYGPGAGQQGPGSQGPGSGGQQGPGGQGPY<br>GPSAAAAAAAAGGYGPGAGQQGPGSGGQQGPGGQGPYGSGQQGPGGAGQQGPGGQGPYGGYGPGAGQQGPGSQGPGSGG<br>QQGPGGQGPYGPSAAAAAAAA |
| 21 | GPGARRQGPGSQGPGSGGQQGPGGQGPYGSGQQGPGGAGQQGPGGQGPYGPGAAAAAAAAGGYGPGAGQQGPGGAGQQG<br>PGSQGPGGQGPYGPGAGQQGPGSQGPGSGGQQGPGGQGPYGPSAAAAAAAAGGYGPGAGQQGPGSQGPGSGGQQGPGGQG<br>PYGPGAAAAAAAVGGYGPGAGQQGPGSQGPGSGGQQGPGGQGPYGPSAAAAAAAAGGYGPGAGQQGPGSQGPGSGGQQGP<br>GGQGPYGPSAAAAAAAA |
| 22 | GPGARRQGPGSQGPGSGGQQGPGGQGPYGSGQQGPGGAGQQGPGGQGPYGPGAAAAAAAAGGYGPGAGQQGPGGAGQQG<br>PGSQGPGGQGPYGPGAGQQGPGSQGPGSGGQQGPGGQGPYGPSAAAAAAAAGGYGPGAGQQGPGSQGPGSGGQQGPGGQP<br>YGPGAAAAAAAVGGYGPGAGQQGPGSQGPGSGGQQGPGGQGPYGPSAAAAAAAAGGYGPGAGQQGPGSQGPGSGGQQGPG<br>GQGPYGPSAAAAAAAA |
| 23 | GGYGPGAGQQGPGSGGQQGPGGQGPYGSGQQGPGGAGQQGPGGQGPYGPGAAAAAAAAGGYGPGAGQQGPGGAGQQGPE<br>GPGSQGPGSGGQQGPGGQGPYGPGAAAAAAAVGGYGPGAGQQGPGSQGPGSGGQQGPGGQGPYGPSAAAAAAAAGGYGPG<br>AGQQGPGSQGPGSGGQQGPGGQGPYGPSAAAAAAAAGGYGPGAGQQGPGSGGQQGPGGQGPYGSGQQGPGGAGQQGPGGQ<br>GPYGPGAAAAAAAA |
| 24 | GVFSAGQGATPWENSQLAESFISRFLRFIGQSGAFSPNQLDDMSSIGDTLKTAIEKMAQSRKSSKSKLQALNMAFASSMAEIAVA<br>EQGGLSLEAKTNAIASALSAAFLETTGYVNQQFVNEIKTLIFMIAQASSNEISGSAAAAGGSSGGGGSGQGGYGQGAYASASA<br>AAAYGSAPQGTGGPASQGPSQQGPVSQPSYGPSATVAVTAVGGRPQGPSAPRQQGPSQQGPGQQGPGGRGPYGPSAAAAAAA<br>A |
| 25 | GAGAGAGAGAGAGAGAGSGASTSVSTSSSSGSGAGAGAGSGAGSGAGAGSGAGAGAGAGGAGAGFGSGLGLGYGVGLSSAQ<br>AQAQAQAAAQAQAQAQAYAAAQAQAQAQAQAAAAAAAAAAGAGAGAGAGAGAGAGSGASTSVSTSSSGSGA<br>GAGAGSGAGSGAGAGSGAGAGAGAGGAGAGFGSGLGLGYGVGLSSAQAQAQAQAAAQAQAQAQAYAAAQAQAQA<br>QAQAAAAAAAAAA |

TABLE 3-continued

Exemplary Repeat Units of Silk or Silk-Like Proteins

| SEQ ID NO | Amino Acid Sequence |
|---|---|
| 26 | GAGAGAGAGAGAGAGAGSGASTSVSTSSSSGSGAGAGAGSGAGSGAGAGSGAGAGAGAGGAGAAFGSGLGLGYGVGLSSAQ AQAQAQAAAQAQADAQAQAYAAAQAQAQAQAQAQAAAAAAAAAAAGAGAGAGAGSGAGAGAGSGASTSVSTSSSSGSGA GAGAGSGAGSGAGAGSGAGAGAGAGGAGAGFGSGLGLGYGVGLSSAQAQAQAQAAAQAQADAQAQAYAAAQAQAQAQA QAQAAAAAAAAAA |
| 27 | GAGAGAGAGSGAGAGAGSGASTSVSTSSSSGSGAGAGAGSGAGSGAGAGSGAGAGAGAGGAGAGFGSGLGLGYGVGLSSAQ AQAQSAAAARAQADAQAQAYAAAQAQAQAQAQAQAAAAAAAAAAAGAGAGAGAGAGAGAGSGASTSVSTSSSSASGA GAGAGSGAGSGAGAGSGAGAGAGAGGAGAGFGSGLGLGYGVGLSSAQAQAQAQAAAQAQAQAQALAAAQAQAQAQAQ AQAAAATAAAAA |
| 28 | GGYGPGAGQQGPGGAGQQGPGSQGPGGQGPYGPGAGQQGPGSQGPGSGGQQGPGGQGPYGPSAAAAAAAAGGYGPGAGQQ GPGSQGPGSGGQQGPGSQGPGSGGQQGPGGQGPYGPSAAAAAAAAGGYGPGAGQQGPGSQGPGSGGQQGPGGQGPYGPGA AAAAAVGGYGPGAGQQGPGSQGPGSGGQQGPGGQGPYGPSAAAAAAAAGGYGPGAGQQGPGSQGPGSGGQQGPGGQGPY GPSAAAAAAA |
| 29 | GGYGPGAGQQGPGGAGQQGPGSQGPGGQGPYGPGAGQQGPGSQGPGSGGQQGPGGQGPYGPSAAAAAAAAGGYGPGAGQQ GPGSQGPGSGGQQGPGSQGPGSGGQQGPGGQGPYGPSAAAAAAAAGGYGPGAGQQGPGSQGPGSGGQQGPGGQGPYGPAA AAAAAVGGYGPGAGQQGPGSQGPGSGGQQGPGGQGPYGPSAAAAAAAAGGYGPGAGQQGPGSQGPGSGGQQGPGGQPYG PSAAAAAAA |
| 30 | GHQGPHRKTPWETPEMAENFMNNVRENLEASRIFPDELMKDMEAITNTMIAAVDGLEAQHRSSYASLQAMNTAFASSMAQLF ATEQDYVDTEVIAGAIGKAYQQITGYENPHLASEVTRLIQLFREEDDLENEVEISFADTDNAIARAAAGAAAGSAAASSSADASA TAEGASGDSGFLFSTGTFGRGGAGAGAGAAAASAAAASAAAAGAEGDRGLFFSTGDFGRGGAGAGAGAAAASAAAASAAAA |
| 31 | GGAQKHPSGEYSVATASAAATSVTSGGAPVGKPGVPAPIFYPQGPLQQGPAPGPSNVQPGTSQQGPIGGVGESNTFSSSFASALG GNRGFSGVISSASATAVASAFQKGLAPYGTAFALSAASAAADAYNSIGSASASAYAQAFARVLYPLLQQYGLSSSADASAFAS AIASSFSTGVAGQGPSVPYVGQQQPSIMVSAASASAAASAAAVGGGPVVQGPYDGGPQQPNIAASAAAAATATSS |
| 32 | GGQGGRGGFGGLGSQGEGGAGQGGAGAAAAAAAAGADGGFGLGGYGAGRGYGAGLGGAGGAGAASAAAAAGGQGGRSGF GGLGSQGAGGAGQGGAGAAAAAAAAGADGGSGLGGYGAGRGYGASLGGADGAGAASAAAAAGGQGGRGGFGGLGSQGAG GAGQGGAGAAAAAAAASGDGGSGLGGYGAGRGYGAGLGGAGGAGAASAAAAAGGEGGRGGFGGLGSQGAGGAGQGGSLA AAAAAAA |
| 33 | GPGGYGGPGQPGPGQGQYGPGPGQQGPRQGGQQGPASAAAAAAAAGPGGYGGPGQQGPRQGQQGPASAAAAAAAAAAGPR GYGGPGQQGPVQGGQQGPASAAAAAAAAGVGGYGGPGQQGPGQGQYGPGTGQQGQGPSGQQGPAGAAAAAAGGAAGPGG YGGPGQQGPGQGQYGPGTGQQGQGPSGQQGPAGAAAAAAAAAGPGGYGGPGQQGPGQGQYGPGAGQQGQGPGSQQGPASA AAAA |
| 34 | GSGAGQGTGAGAGAAAAAAGAAGSGAGQGAGSGAGAAAAAAAAASAAGAGQGAGSGSGAGAAAAAAAAAAAGAGQGAGSGS GAGAAAAAAAAAAAAAQQQQQQQAAAAAAAAAAAAAAGSGQGASFGVTQQFGAPSGAASSAAAAAAAAAAAAAAAGSGAGQEA GTGAGAAAAAAAAGAAGSGAGQGAGSGAGAAAAAAAAAAAAAGAGQGAGSGSGAGAAAAAAAAAAAAAQQQQQQAAAA AAAAAAA |
| 35 | GGAQKQPSGESSVATASAAATSVTSAGAPVGKPGVPAPIFYPQGPLQQGPAPGPSYVQPATSQQGPIGGAGRSNAFSSSFASALS GNRGFSEVISSASATAVASAFQKGLAPYGTAFALSAASAAADAYNSIGSANAFAYAQAFARVLYPLVQQYGLSSSAKASAFAS AIASSFSSGAAGQGQSIPYGGQQQPPMTISAASASAGASAAAVKGGQVGQGPYGGQQSTAASASAAATTATA |
| 36 | GADGGSGLGGYGAGRGYGAGLGGADGAGAASAAAAAGGQGGRGGFGRLGSQGAGGAGQGGAGAAAAVAAAGGDGGSGL GGYGAGRGYGAGLGGAGGAGAASAAAAAGGQGGRGGFGGLGSQGAGGAGQGGAGAAAASGDGGSGLGGYGAGRGYGAGL GGADGAGAASAASAAGGQGGRGGFGGLGSQGAGGAGQGGAGAAAAAATAGGDGGSGLGGYGAGRGYGAGLGGAGGAGA ASAAAAA |
| 37 | GAGAGQGGRGGYGQGGFGGQGSGAGAGASAAAGAGAGQGGRGGYGQGGFGGQGSGAGAGASAAAGAGAGQGGRGGYGQ GGFGQGSGAGAGASAAAAAGAGQGGRGGYGQGGLGGSGSGAGAGAGAAAAAAAGAGGYGQGGLGGYGQGAGAGQGGL GGYGSGAGAGASAAAAGAGGAGQGGLGGYGQGAGAGQGGLGGYGSGAGAGAAAAAAAGAGGSGQGGLGGYGSGGGAG GASAAAA |
| 38 | GAYAYAYAIANAFASILANTGLLSVSSAASVASSVASAIATSVSSSSAAAAASASAAAAAASAGASAASSASASSSASAAAGAGAG AGAGASGASGAAGGSGGFGLSSGFGAGIGGLGGYPSGALGGLGIPSGLLSSGLLSPAANQRIASLIPLILSAISPNGVNFGVIGSNIA SLASQISQSGGGIAASQAFTQALLELVAAFIQVLSSAQIGAVSSSSASAGATANAFAQSLSSAFAG |
| 39 | GAAQKQPSGESSVATASAAATSVTSGGAPVGKPGVPAPIFYPQGPLQQGPAPGPSNVQPGTSQQGPIGGVGGSNAFSSSFASALS LNRGFTEVISSASATAVASAFQKGLAPYGTAFALSAASAAADAYNSIGSANAFAYAQAFARVLYPLVRQYGLSSSGKASAFAS AIASSFSSGTSGQGPSIGQQQPPVTISAASASAGASAAAVGGGQVGQGPYGGQQSTAASASAAAATATS |
| 40 | GAAQKQPSGESSVATASAAATSVTSGGAPVGKPGVPAPIFYPQGPLQQGPAPGPSNVQPGTSQQGPIGGVGGSNAFSSSFASALS LNRGFTEVISSASATAVASAFQKGLAPYGTAFALSAASAAADAYNSIGSANAFAYAQAFARVLYPLVRQYGLSSSGKASAFAS AIASSFSSGTSGQGPSIGQQQPPVTISAASASAGASAAAVGGGQVGQGPYGGQQSTAASASAAAATATS |
| 41 | GAAQKQPSGESSVATASAAATSVTSGGAPVGKPGVPAPIFYPQGPLQQGPAPGPSNVQPGTSQQGPIGGVGGSNAFSSSFASALS LNRGFTEVISSASATAVASAFQKGLAPYGTAFALSAASAAADAYNSIGSANAFAYAQAFARVLYPLVQQYGLSSSAKASAFAS AIASSFSSGTSGQGPSIGQQQPPVTISAASASAGASAAAVGGGQVGQGPYGGQQSTAASASAAAATATS |

TABLE 3-continued

Exemplary Repeat Units of Silk or Silk-Like Proteins

| SEQ ID NO | Amino Acid Sequence |
|---|---|
| 42 | GGAQKQPSGESSVATASAAATSVTSAGAPVGKPGVPAPIFYPQGPLQQGPAPGPSNVQPGTSQQGPIGGVGGSNAFSSSFASALS LNRGFTEVISSASATAVASAFQKGLAPYGTAFALSAASAAADAYNSIGSGANAFAYAQAFARVLYPLVQQYGLSSSAKASAFAS AIASSFSSGTSGQGPSNGQQQPPVTISAASASAGASAAAVGGGQVSQGPYGGQQQSTAASASAAAATATS |
| 43 | GGAQKQPSGESSVATASAAATSVTSAGAPGGKPGVPAPIFYPQGPLQQGPAPGPSNVQPGTSQQGPIGGVGGSNAFSSSFASALS LNRGFTEVISSASATAVASAFQKGLAPYGTAFALSAASAAADAYNSIGSGANAFAYAQAFARVLYPLVQQYGLSSSAKASAFAS AIASSFSSGTSGQGPSIGQQQPPVTISAASASAGASAAAVGGGQVGQGPYGGQQQSTAASASAAAATATS |
| 44 | GPGGYGGPGQQGPGQGQQQGPASAAAAAAAAGPGGYGGPGQQGPGQGQQQGPASAAAAAAAAAAGPGGYGGPGQQRPGQA QYGRGTGQQGQGPGAQQGPASAAAAAAAAGAGLYGGPGQQGPGQGQQQGPASAAAAAAAAAAAGPGGYGGPGQQGPGQAQ QQGPASAAAAAAAAGPGGYSGPGQQGPGQAQQQGPASAAAAAAAAAAGPGGYGGPGQQGPGQGQQQGPASAAAAAAATAA |
| 45 | GAGGDGGLFLSSGDFGRGGAGAGAGAAAASAAAASSAAAGARGGSGFGVGTGGFGRGGAGDGASAAAASAAAASAAAAGA GGDSGLFLSSGDFGRGGAGAGAGAAAASAAAASAAAAGTGGVGGLFLSSGDFGRGGAGAGAGAAAASAAAASSAAAGARGG SGFGVGTGGFGRGGPGAGTGAAAASAAAASAAAAGAGGDSGLFLSSEDFGRGGAGAGTGAAAASAAAASAAAA |
| 46 | GAGRGYGGGYGGGAAAGAGAGAGAGRGYGGGYGGGAGSGAGSGAGAGGGSGYGRGAGAGAGAGAAAAAGAGAGGAGG YGGGAGAGAGASAAAGAGAGAGGAGGYGGGYGGGAGAGAGAGAAAAAGAGAGAGAGRGYGGGFGGGAGSGAGAGAGA GGGSGYGRGAGGYGGGYGGGAGTGAGAAAATGAGAGAGAGRGYGGGYGGGAGAGAGAGAGAGGGSGYGRGAGAGASVA A |
| 47 | GALGQGASVWSSPQMAENFMNGFSMALSQAGAFSGQEMKDFDDVRDIMNSAMDKMIRSGKSGRGAMRAMNAAFGSAIAEIV AANGGKEYQIGAVLDAVTNTLLQLTGNADNGFLNEISRLITLFSSVEANDVSASAGADASGSSPVGGYSSGAGAAVGQGTAQ AVGGYGGGAQGVASSAAAGATNYAQGVSTGSTQNVATSTVTTTTNVAGSTATGYNTGYGIGAAAGAAA |
| 48 | GGQGGQGGYDGLGSQGAGQGGYGQGGAAAAAAAASGAGSAQRGGLGAGGAGQGGYGAGSGGQGGAGQGGAAAATAAAAG GQGGQGGYGGLGSQGSGQGGYGQGGAAAAAAAAASGDGGAGQEGLGAGGAGQGGYGAGLGGQGGAGQGGAAAAAAAAAGG QGGQGGYGGLGSQGAGQGGYGQGGAAAAAAAAASGAGGAGQGGLGAAGAGQGGYGAGSGGQGGAGQGGAAAAAAAAA |
| 49 | GGQGGQGGYGGLGSQGAGQGGYGQGGVAAAAAAASGAGGAGRGGLGAGGAGQEYGAVSGGQGGAGQGGEAAAAAAAAG GQGGQGGYGGLGSQGAGQGGYGQGGAAAAAAAAASGAGGARRGGLGAGGAGQGGYGAGLGGQGGAGQGSASAAAAAAAAGG QGGQGGYGGLGSQGSGQGGYGQGGAAAAAAAAASGAGGAGRGSLGAGGAGQGGYGAGLGGQGGAGQGGAAAAASAAA |
| 50 | GPGGYGGPGQQGPGQGQYGPGTGQQGQGPGGQQGPVGAAAAAAAAVSSGGYGSQGAGQGGQQGSGQRGPAAAGPGGYSGP GQQGPGQGGQQGPASAAAAAAAAAGPGGYGGSGQQGPGQGRGTGQQGQGPGGQQGPASAAAAAAAGPGGYGGPGQQGPG QGQYGPGTGQQGQGPASAAAAAAAAGPGGYGGPGQQGPGQGQYGPGTGQQGQGPGGQQGPGGASAAAAAAA |
| 51 | GGYGPGAGQQGPGSGQQGPGGQGPYGSGQQGPGGAGQQGPGGQGPYGPGAAAAAAAAAGGYGPGAGQQGPGGAGQQGP GSQGPGGQGPYGPGAGQQGPGSQGPGSGQQGPGGQGPYGPSAAAAAAAAAGGYGPGAGQRSQGPGGQGPYGPGAGQQGPG SQGPGSGQQGPGGQGPYGPSAAAAAAAAGPGAGRQGPGSQGPGSGQQGPGGQGPYGPSAAAAAAAA |
| 52 | GQGGQGGQGGLGQGGYGQGAGSSAAAAAAAAAAAAAAGRGQGGYGQGSGGNAAAAAAAAAAAAASGQGSQGGQGGQGG GYGQGAGSSAAAAAAAAAAAASGRGQGGYGQGAGGNAAAAAAAAAAAAAGQGGQGGYGGLGQGGYGQGAGSSAAAA AAAAAAAGGQGGQGGQGGYGQGSGGSAAAAAAAAAAAAAAAGRGQGGYGQGSGGNAAAAAAAAAAAAAAA |
| 53 | GRGPGGYGPGQQGPGGPGAAAAAAGPGGYGPGGYGPGQQGPGGPGAAAAAAAGRGPGGYGPGQQGPGQQGPGGSAAAAA AGRGPGGYGPGQQGPGGPGAAAAAAGPGGYGPGQQGPGAAAAAAAAGRGPGGYGPGQQGPGGPGAAAAAAAGRGPGGYGP GQQGPGQQGPGGSAAAAAAGRGPGGYGPGQQGPGGPGAAAAAAGPGGYGPGQQGPGAAAAAAAA |
| 54 | GRGPGGYGPGQQGPGGSGAAAAAAGRGPGGYGPGQQGPGGPGAAAAAAGPGGYGPGQQGTGAAAAAAAGSGAGGYGPGQ QGPGGPGAAAAAAGPGGYGPGQQGPGAAAAAAAGSGPGGYGPGQQGPGGSSAAAAAAAGPGRYGPGQQGPGAAAAASAGRG PGGYGPGQQGPGGPGAAAAAAGPGGYGPGQQGPGAAAAAAGSGPGGYGPGQQGPGGPGAAAAAAA |
| 55 | GAAATAGAGASVAGGYGGGAGAAAGAGAGGYGGGYGAVAGSGAGAAAASSGAGGAAGYGRGYGAGSGAGAGAGTVAA YGGAGGVATSSSSATASGSRIVTSGGYGYGTSAAAGAGVAAGSYAGAVNRLSSAEAASRVSSNIAAIASGGASALPSVISNIYSG VVASGVSSNEALIQALLELLSALVHVLSSASIGNVSSVGVDSTLNVVQDSVGQYVG |
| 56 | GGGQGGFSGQGQGGFGPGAGSSAAAAAAAAAAARQGGGQGGFGQGAGGNAAAAAAAAAAAAAAAQGGGQGGFSGRGQGGF GPGAGSSAAAAAAGQGGQGGFGQGAGGNAAAAAAAAAAAAAAAGQGGQGRGGFGQGAGGNAAAAAAAAAAAAAAAAQ QGGGQGGFGGRGQGGFGPGAGSSAAAAAAGQGGQGRGGFGQGAGGNAAASAAAAASAAAAGQ |
| 57 | GGYGPGAGQQGPGGAGQQGPGSQGPGGAGQQGPGGQGPYGPGAAAAAAAAVGGYGPGAGQQGPGSQGPGSGQQGPGGQGP YGPSAAAAAAAAAGGYGPGAGQQGPGSQGPGSGQQGPGGLGPYGPSAAAAAAAAAGGYGPGAGQQGPGSQGPGSGQQRPGG LGPYGPSAAAAAAAAAGGYGPGAGQQGPGSQGPGSGQQRPGGLGPYGPSAAAAAAAA |
| 58 | GAGAGGGYGGGYSAGGGAGAGSGAAAGAGAGRGGAGGYSAGAGTGAGAAAGAGTAGGYSGGYGAGASSSAGSSFISSSSMS SSQATGYSSSSGYGGGAASAAAGAGAAAGGYGGGYGAGAGAGAAAASGATGRVANSLGAMASGGINALPGVFSNIFSQVSAA SGGASGGAVLVQALTEVIALLLHILSSASIGNVSSQGLEGSMAIAQQAIGAYAG |
| 59 | GAGAGGAGGYAQGYGAGAGAGAGTGAGGAGGYGQGYGAGSGAGAGGAGGYGAGAGAGAGAGDASGYGQGYGDGAG AGAGAAAAGAAAGARGAGGYGGGAGAGAGAGAGAAGGYGQGYGAGAGEGAGAGAGAVAGAGAAAAGAGAGAGG AEGYGAGAGAGGAGGYGQSYGDGAAAAAGSGAGAGGSGGYGAGAGAGSGAGAAGGYGGGAGA |

TABLE 3-continued

Exemplary Repeat Units of Silk or Silk-Like Proteins

| SEQ ID NO | Amino Acid Sequence |
|---|---|
| 60 | GPGGYGPGQQGPGGYGPGQQGPGRYGPGQQGPSGPGSAAAAAAGSGQQGPGGYGPRQQGPGGYGQGQQGPSGPGSAAAASA AASAESGQQGPGGYGPGQQGPGGYGPGQQGPGGYGPGQQGPSGPGSAAAAAAAASGPGQQGPGGYGPGQQGPGGYGPGQQG PSGPGSAAAAAAASGPGQQGPGGYGPGQQGPGGYGPGQQGLSGPGSAAAAAAA |
| 61 | GRGPGGYGQGQQGPGGPGAAAAAAGPGGYGPGQQGPGAAAAAAAGSGPGGYGPGQQGPGRSGAAAAAAAGRGPGGYGPG QQGPGGPGAAAAAAGPGGYGPGQQGPGAAAAAASAGRGPGGYGPGQQGPGGSGAAAAAAAGRGPGGYGPGQQGPGGPGAAAA AAAGRGPGGYGPGQQGPGQQGPGGSGAAAAAAAGRGPGGYGPGQQGPGGPGAAAAAA |
| 62 | GVGAGGEGGYDQGYGAGAGAGSGGGAGGAGGYGGGAGAGSGGGAGGAGGYGGGAGAGAGAGGAGGYGGGAGAGTG ARAGAGGVGGYGQSYGAGASAAAGAGVGAGGAGGAGGYGQGYGAGAGIGAGDAGGYGGGAGAGASAGAGGYGGGAG AGAGGVGGYGKGYGAGSGAGAAAAAGAGAGSAGGYGRGDGAGAGGASGYGQGYGAGAAA |
| 63 | GYGAGAGRGYGAGAGAGAGAVAASGAGAGAGYGAGAGAGAGAGYGAGAGRGYGAGAGAGAGSGAASGAGAGAGYGAG AGAGAGYGAGAGSGYGTGAGAGAAAAGGAGAGAGYGAGAGRGYGAGAGAGAGSGAGAGAGAGAASGAGAGSGYGAG AAAAGGAGAGAGGGYGAGAGRGYGAGAGAGAGSGSGSAAGYGQGYGSGSGAGAAA |
| 64 | GQGTDSSASSVSTSTSVSSSATGPDTGYPVGYYGAGQAEAAASAAAAAAASAAEAATIAGLGYGRQGQGTDSSASSVSTSTSVS SSATGPDMGYPVGNYGAGQAEAAASAAAAAAASAAEEAATIASLGYGRQGQGTDSSASSVSTSTSVSSSATGPGSRYPVRDYGA DQAEAAASAAAAAAAASAAEEIASLGYGRQ |
| 65 | GQGTDSVASSASSSASASSSATGPDTGYPVGYYGAGQAEAAASAAAAAAASAAEAATIAGLGYGRQGQGTDSSASSVSTSTSVS SSATGPGSRYPVRDYGADQAEAAASATAAAAAAASAAEEIASLGYGRQGQGTDSVASSASSSASASSSATGPDTGYPVGYYGA GQAEAAASAAAAAAASAAEEAATIAGLGYGRQ |
| 66 | GQGGQGGYGGLGQGGYGQGAGSSAAAAAAAAAAAAAAGGQGGQGQGRYGQGAGSSAAAAAAAAAAAAAAAGRGQGGYGQG SGGNAAAAAAAAAAAAAASGQGSQGGQGGQGQGGYGQGAGSSAAAAAAAAAAAAAASGRGQGGYGQGAGGNAAAAAAAAAA AAAAGQGGQGGYGGLGQGGYGQGAGSSAAAAAAAAAAAA |
| 67 | GGLGGQGGLGGLGSQGAGLGGYGQGGAGQGGAAAAAAAAGGLGGQGGRGGLGSQGAGQGGYGQGGAGQGGAAAAAAAA GGLGGQGGLGALGSQGAGQGGAGQGGYGQGGAAAAAAAGGLGGQGGLGGLGSQGAGQGGYGQGGAGQGGAAAAAAAAGG LGGQGGLGGLGSQGAGPGGYGQGGAGQGGAAAAAAAA |
| 68 | GGQGRGGFGQGAGGNAAAAAAAAAAAAAAAQQVGQFGFGGRGQGGFGPFAGSSAAAAAAASAAAGQGGQGGGFGQGAGG NAAAAAAAAAAAARQGGQGGGFSQGAGGNAAAAAAAAAAAAAAAQQGGQGGFGGRGQGGFGPGAGSSAAAAAAATAA AGQGGQGRGGFGQGAGSNAAAAAAAAAAAAAAAAGQ |
| 69 | GGQGGQGGYGGLGSQGAGQGGYGAGQGAAAAAAAGGAGGAGRGGLGAGGAGQGYGAGLGGQGGAGQAAAAAAAGGA GGARQGGLGAGGAGQGYGAGLGGQGGAGQGGAAAAAAAAGGQGGQGGYGGLGSQGAGQGGYGAGQGGAAAAAAAAGG QGGQGGYGGLGSQGAGQGGYGGRQGGAGAAAAAAAA |
| 70 | GGAGQRGYGGLGNQGAGRGGLGGQGAGAAAAAAAGGAGQGGYGGLGNQGAGRGGQGAAAAAGGAGQGGYGGLGSQGAG RGGQGAGAAAAAAVGAGQGEGIRGQGAGQGGYGGLGSQGSGRGGLGGQGAGAAAAAAAGGAGQGGLGGQGAGQGAGAAAAA AAGGVRQGGYGGLGSQGAGRGGQGAGAAAAAA |
| 71 | GGAGQGGLGGQGAGQGAGASAAAAGGAGQGGYGGLGSQGAGRGGEGAGAAAAAAAGGAGQGGYGGLGGQGAGQGGYGGL GSQGAGRGGLGGQGAGAAAAGGAGQGGLGGQGAGQGAGAAAAAAAGGAGQGGYGGLGSQGAGRGGLGGQGAGAVAAAAA GGAGQGGYGGLGSQGAGRGGQGAGAAAAAA |
| 72 | GAGAGAGAGSGAGAAGGYGGGAGAGAVGAGGAGGYDQGYGAGAGAGSGAGAGGAGGYGGGAGAGADAGAGGAGGYGGG AGAGARAGAGGVGGYGQSYGAGAGAGAGVGAGGAGGAGGADGYGQGYGAGAGTGAGDAGGYGGGAGAGASAGAGGY GGGAGAGGVGVYGKGYGSGSGAGAAAAA |
| 73 | GGAGGYGVGQGYGAGAGAGAAAGAGAGGYGAGQGYGAGAGVGAAAAAGAGAGVGGAGGYGRGAGAGAGAGAA AGAGAGAAAGAGAGGAGGYGAGQGYGAGAGVGAAAAAGAGAGVGGAGGYGRGAGAGAGAGAGGAGGYGRGAGAGA GAGAGGAGGYGAGQGYGAGAGAGAAAAA |
| 74 | GEAFSASSASSASSAVVFESAGPGEEAGSSGDGASAAAASAAAAAGAGSGRRGPGGARSRGGAGAGAGAGSGVGGYGSGSGAGAGA GAGAGAGGEGGFGEGQGYGAGAGAGFGSGAGAGAGAGSGAGAGEGVGSGAGAGAGAGFGVGAGAGAGAGAGFGSGAGAG SGAGAGYGAGRAGGRGRGGRG |
| 75 | GEAFSASSASSASSAVVFESAGPGEEAGSSGGGASAAAASAAAAAGAGSGRRGPGGARSRGGAGAGAGAGSGVGGYGSGSGAGAGA GAGAGAGGEGGFGEGQGYGAGAGAGFGSGAGAGAGAGSGAGAGEGVGSGAGAGAGAGFGVGAGAGAGAGAGFGSGAGAG SGAGAGYGAGRAGGRGRGGRG |
| 76 | GNGLGQALLANGVLNSGNYLQLANSLAYSFGSSLSQYSSSAAGASAAGAASGAAGAGAGAASSGGSSGSASSSTTTTTTTSTSA AAAAAAAAAAAASAAASTSASASASASASASASAFSQTFVQTVLQSAAFGSYFGGNLSLQSAQAAASAAAQAAAQQIGLGSYGYAL ANAVASAFASAGANA |
| 77 | GNGLGQALLANGVLNSGNYLQLANSLAYSFGSSLSQYSSSAAGASAAGAASGAAGAGAGAASSGGSSGSASSSTTTTTTTSTSA AAAAAAAAAAAASAAASTSASASASASASASASAFSQTFVQTVLQSAAFGSYFGGNLSLQSAQAAASAAAQAAAQQIGLGSYGYAL ANAVASAFASAGANA |

TABLE 3-continued

Exemplary Repeat Units of Silk or Silk-Like Proteins

| SEQ ID NO | Amino Acid Sequence |
|---|---|
| 78 | GNGLGQALLANGVLNSGNYLQLANSLAYSFGSSLSQYSSSAAGASAAGAASGAAGAGAGAASSGGSSGSASSSTTTTTTTSTSA AAAAAAAAAAASAAASTSASASASASASASASAFSQTFVQTVLQSAAFGSYFGGNLSLQSAAAASAAAQAAAQQIGLGSYGYAL ANAVASAFASAGANA |
| 79 | GASGAGQGQGYGQQGQGGSSAAAAAAAAAAAAAAAQGQGQGYGQQGQGSAAAAAAAAAAAGASGAGQGQGYGQQGQGSA AAAAAAAAGASGAGQGQGYGQQGQGGSSAAAAAAAAAAAAAAAAQGQGYGQQGQGSAAAAAAAAAAGASGAGQGQGYG QQGQGGSSAAAAAAAAAAAAAAA |
| 80 | GRGQGGYGQGSGGNAAAAAAAGQGGFGGQEGNGQGAGSAAAAAAAAAAAAGGSGQGRYGGRGQGGYGQGAGAAASAAA AAAAAAGQGGFGGQEGNGQGAGSAAAAAAAAAAAAAAGGSGQGGYGGRGQGGYGQGAGAAAAAAAAAAAAAAAAGQGGQ GFGSQGGNGQGAGSAAAAAAAAAA |
| 81 | GQNTPWSSTELADAFINAFMNEAGRTGAFTADQLDDMSTIGDTIKTAMDKMARSNKSSKGKLQALNMAFASSMAEIAAVEQG GLSVDAKTNAIADSLNSAFYQTTGAANPQFVNEIRSLINMFAQSSANEVSYGGGYGGQSAGAAASAAAAGGGGQGGYGNLGG QGAGAAAAAASAA |
| 82 | GQNTPWSSTELADAFINAFLNEAGRTGAFTADQLDDMSTIGDTLKTAMDKMARSNKSSQSKLQALNMAFASSMAEIAAVEQGG LSVAEKTNAIADSLNSAFYQTTGAVNVQFVNEIRSLISMFAQASANEVSYGGGYGGGQGGQSAGAAAAAASAGAGQGGYGGL GGQGAGSAAAAAA |
| 83 | GGQGGQGGYGGLGSQGAGQGGYGQGGAAAAAASAGGQGGQGGYGGLGSQGAGQGGYGGGAFSGQQGGAASVATASAAAS RLSSPGAASRVSSAVTSLVSSGGPTNSAALSNTISNVVSQISSSNPGLSGCDVLVQALLEIVSALVHILGSANIGQVNSSGVGRSASI VGQSINQAFS |
| 84 | GGAGQGGYGGLGGQGAGAAAAAAGGAGQGGYGGQGAGQGAAAAAASGAGQGGYEGPGAGQGAGAAAAAAGGAGQGGY GGLGGQGAGQGAGAAAAAAGGAGQGGYGGLGGQGAGQGAGAAAAAAGGAGQGGYGGQGAGQGAAAAAAGGAGQGGYG GLGSQGGGYGRQGAGAAAAAAAA |
| 85 | GASSAAAAAAATATSGGAPGGYGGYGPGIGGAFVPASTTGTGSGSGSGAGAAGSGGLGGLGSSGGSGGLGGGNGGSGASAAA SAAAASSSPGSGGYGPGQGVGSGSGSAAGGSGTGSGAGGPGSGGYGGPQFFASAYGGQGLLGTSGYGNGQGGASGTGSGGV GGSGSGAGSNS |
| 86 | GQPIWTNPNAAMTMTNNLVQCASRSGVLTADQMDDMGMMADSVNSQMQKMGPNPPQHRLRAMNTAMAAEVAEVVATSPP QSYSAVLNTIGACLRESMMQATGSVDNAFTNEVMQLVKMLSADSANEVSTASASGASYATSTSSAVSSSQATGYSTAAGYGNA AGAGAGAAAAVS |
| 87 | GQKIWTNPDAAMAMTNNLVQCAGRSGALTADQMDDLGMVSDSVNSQVRKMGANAPPHKIKAMSTAVAAGVAEVVASSPPQ SYSAVLNTIGGCLRESMMQVTGSVDNTFTTEMMQMVNMFAADNANEVSASASGSGASYATGTSSAVSTSQATGYSTAGGYGT AAGAGAGAAAAA |
| 88 | GSGYGAGAGAGAGSGYGAGAGAGSGYGAGAGAGAGSGYVAGAGAGAGAGSGYGAGAGAGAGSSYSAGAGAGAGSGYGA GSSASAGSAVSTQTVSSSATTSSQSAAAATGAAYGTRASTGSGASAGAAASGAGAGYGGQAGYGQGGGAAAYRAGAGSQAA YGQGASGSSGAAAAA |
| 89 | GGGQGGRGGFGGLSSQGAGGAGQGGSAAAAAAAGGDGGSGLGDYGAGRGYGAGLGGAGGAGVASAAASAAASRLSSPSA ASRVSSAVTSLISGGGPTNPAALSNTFSNVVYQISVSSPGLSGCDVLIQALLELVSALVHILGSAIIGQVNSSAAGESASLVGQSVY QAFS |
| 90 | GVGQAATPWENSQLAEDFINSFLRFIAQSGAFSPNQLDDMSSIGDTLKTAIEKMAQSRKSSKSKLQALNMAFASSMAEIAVAEQG GLSLEAKTNAIANALASAFLETTGFVNQQFVSEIKSLIYMIAQASSNEISGSAAAAGGGSGGGGGSGQGGYGQGASASASAAAA |
| 91 | GGGDYGQGGYGNQRGVGSYGQGAGAGAAATSAAGGAGSGRGGYGEQGGLGGYGQGAGAGAASTAAGGGDGYGQGGYG NQGGRGSYGQGSGAGAGAAVAAAAGGAVSGQGGYDGEGGQGGYGQGSGAGAAVAAASGGTGAGQGGYGSQGSQAGYGQ GAGFRAAAATAAA |
| 92 | GAGAGYGGQVGYGQGAGASAGAAAAGAGAGYGGQAGYGQGAGGSAGAAAAGAGAGRQAGYGQGAGASARAAAAGAGT GYGQGAGASAGAAAAGAGAGSQVGYGQGAGASSGAAAAAGAGAGYGGQVGYEQGAGASAGAEAAASSAGAGYGGQAGY GQGAGASAGAAAA |
| 93 | GGAGQGGYGGLGGQGAGQGGLGGQRAGAAAAAAGGAGQGGYGGLGSQGAGRGGYGGVGSGASAASAAAASRLSSPEASSRV SSAVSNLVSSGPTNSAALSSTISNVVSQISASNPGLSGCDVLVQALLEVVSALIQILGSSSIGQVNYGTAGQAAQIVGQSVYQALG |
| 94 | GGYGPGSGQQGPGGAGQQGPGGQGPYGPGSSSAAAVGGYGPSSGLQGPAGQGPYGPGAAASAAAAAGASRLSSPQASSRVSS AVSSLVSSGPTNSAALTNTISSVVSQISASNPGLSGCDVLIQALLEISVALVHILGYSSIGQINYDAAAQYASLVGQSVAQALA |
| 95 | GGAGAGQGSYGGQGGYGQGGAGAATAAAAGGAGSGQGGYGGQGGLGGYGQGAGAGAAAAAAAAGGAGAGQGGYG GQGGQGGYGQGAGAGAAAAAAGGAGAGQGGYGGQGGYGQGGGAGAAAAAASGGSGSQGGYGGQGGLGGYGQGAG AGAGAAAASAAAA |
| 96 | GQGGQGGYGRQSQGAGSAAAAAAAAAAAAAAGSGQGGYGGQGGYGQSSASASAAASAASTVANSVSRLSSPSAVSRVSS AVSSLVSNGQVNMAALPNIISNISSSVSASAPGASGCEVIVQALLEVITALVQIVSSSSVGYINPSAVNQITNVVANAMAQVMG |

TABLE 3-continued

Exemplary Repeat Units of Silk or Silk-Like Proteins

| SEQ ID NO | Amino Acid Sequence |
|---|---|
| 97 | GGAGQGGYGGLGGQGSGAAAAGTGQGGYGSLGGQGAGAAGAAAAAVGGAGQGGYGGVGSAAASAAASRLSSPEASSRVSS AVSNLVSSGPTNSAALSNTISNVVSQISSSNPGLSGCDVLVQALLEVVSALIHILGSSSIGQVNYGSAGQATQIVGQSVYQALG |
| 98 | GAGAGGAGGYGAGQGYGAGAGAGAAAGAGAGGARGYGARQGYGSGAGAGAGARAGGAGGYGRGAGAGAAAASGAGAG GYGAGQGYGAGAGAVASAAAGAGSGAGGAGGYGRGAGAVAGAGAGGAGGYGAGAGAAAGVGAGGSGGYGGRQGGYSA GAGAGAAAAA |
| 99 | GQGGQGGYGGLGQGGYGQGAGSSAAAAAAAAAAAGRGQGGYGQGSGGNAAAAAAAAAAAAASGQGGQGGQGGQGQGGYG QGAGSSAAAAAAAAAAAAAAGRGQGGYGQGAGGNAAAAAAAAAAAASGQGGQGGQGGQGQGGYGQGAGSSAAAAAAA AAAAAAA |
| 100 | GGYGPGSGQQGPGQQGPGQQGPGQQGPYGAGASAAAAAAGGYGPGSGQQGPGVRVAAPVASAAASRLSSSAASSRVSSAVSS LVSSGPTTPAALSNTISSAVSQISASNPGLSGCDVLVQALLEVVSALVHILGSSSVGQINYGASAQYQAMVGQSVTQALV |
| 101 | GAGAGGAGYGRGAGAGAGAAAGAGAGAAAGAGAGAGGYGGQGGYGAGAGAGAAAAGAGAGGAAGYSRGGRAGAAGA GAGAAAGAGAGAGGYGGQGGYGAGAGAGAAAAGAGSGGAGGYGRGAGAGAAAGAGAAAGAGAGAGGYGGQGGYGAG AGAAAAA |
| 102 | GAGAGRGGYGRGAGAGGYGGQGGYGAGAGAGAAAAGAGAGGYGDKEIACWSRCRYTVASTTSRLSSAEASSRISSAASTL VSGGYLNTAALPSVISDLFAQVGASSPGVSDSEVLIQVLLEIVSSLIHILSSSSVGQVDFSSVGSSAAAVGQSMQVVMG |
| 103 | GAGAGAGGAGGYGRGAGAGAGAGAAAAGQGYGSGAGAGAGASAGGAGSYGRGAGAGAAAASGAGAGGYGAGQGYGA GAGAVASAAAGAGSGAGGAGGYGRGAVAGSGAGAGAGGAGGYGAGAGAGAAAGAVAGGSGGYGGRQGGYSAGAGAG AAAAA |
| 104 | GPGGYGPVQQGPSGPGSAAGPGGYGPAQQGPARYGPGSAAAAAAAAGSAGYGPGPQASAAASRLASPDSGARVASAVSNLVS SGPTSSAALSSVISNAVSQIGASNPGLSGCDVLIQALLEIVSACVTILSSSSIGQVNYGAASQFAQVVGQSVLSAFS |
| 105 | GTGGVGGLFLSSGDFGRGGAGAGAGAAAASAAAASSAAAGARGGSGFGVGTGGFGRGGAGAGTGAAAASAAAASAAAAGA GGDGGLFLSSGDFGRGGAGAGAGAAAASAAAASSAAAGARGGSGFGVGTGGFGRGGAGDGASAAAASAAAASAAAA |
| 106 | GGYGPGAGQQGPGGAGQQGPGGQGPYGPSVAAAASAAGGYGPGAGQQGPVASAAVSRLSSPQASSRVSSAVSSLVSSGPTNPA ALSNAMSSVVSQVSASNPGLSGCDVLVQALLEIVSALVHILGSSSIGQINYAASSQYAQMVGQSVAQALA |
| 107 | GGAGQGGYGGLGSQGAGRGGYGGQGAGAAAAATGGAGQGGYGGVGSGASAASAAASRLSSPQASSRVSSAVSNLVASGPTN SAALSSTISNAVSQIGASNPGLSGCDVLIQALLEVVSALIHILGSSSIGQVNYSAGQATQIVGQSVYQALG |
| 108 | GGAGQGGYGGLGSQGAGRGGYGGQGAGAAVAAIGVGQGGYGGVGSGASAASAAASRLSSPEASSRVSSAVSNLVSSGPTNS AALSSTISNVVSQIGASNPGLSGCDVLIQALLEVVSALVHILGSSSIGQVNYGSAGQATQIVGQSVYQALG |
| 109 | GASGGYGGGAGEGAGAAAAAGAGAGGAGGYGGGAGSGAGAVARAGAGGAGGYGSGIGGGYGSGAGAAAGAGAGGAGAY GGGYGTGAGAGARGADSAGAAAGYGGGVGTGTGSSAGYGRGAGAGAGAGAAAGSGAGAAGGYGGGYGAGAGAGA |
| 110 | GAGSGQGGYGGQGGLGGYGQGAGAGAAAGASGSGSGGAGQGGLGGYGQGAGAGAAAAAGASGAGQGGFGPYGSSYQSS TSYSVTSQGAAGGLGGYGQGSGAGAAAAGAAGQGGQGGYGQGAGAGAGAGAGQGGLGGYGQGAGSSAASAAAA |
| 111 | GGAGQGGYGGLGGQGVGRGGLGGQGAGAAAAGGAGQGGYGGVGSGASAASAAASRLSSPQASSRLSSAVSNLVATGPTNSA ALSSTISNVVSQIGASNPGLSGCDVLIQALLEVVSALIQILGSSSIGQVNYGSAGQATQIVGQSVYQALG |
| 112 | GAGSGGAGGYGRGAGAGAGAAAGAGAGAGSYGGQGGYGAGAGAGAAAAGAGAGAGGYGRGAGAGAGAGAGAAAARAG AGAGGAGYGGQGGYGAGAGAGAAAAGAGAGGAGGYGRGAGAGAGAAAGAGAGAGGYGGQSGYGAGAGAAAAA |
| 113 | GASGAGGQGQGYGQGQGGSSAAAAAAAAAAQGQGQGYGQGQGYGQGQGGSSAAAAAAAAAAAAAQGQGQGYGQGQG QGSAAAAAAAAAAGASGAGQGQGYGQGQGGSSAAAAAAAAAAAAAAQGQGYGQGQGQSAAAAAAAAAAAAAAA |
| 114 | GGYGPGAGQQGPGSGGQQGPGGQGPYGSGQQGPGAGQQGPGGQGPYGPAAAAAAAAAGGYGPGAGQQGPGGAGQQGP GSQGPGGQGPYGPGAGQQGPGSQGPGSGGQQGPGGQGPYGPSAAAAAAAAAGGYGPGAGQRSQGPGGQGPYGPGAGQQGP SQGPGSGGQQGPGGQGPYGPSAAAAAAAAAGGYGPGAGQQGPGSQGPGSGGQQGPGGQGPYGPAAAAAAAAVGGYGPGAGQ QGPGSQGPGSGGQQGPGGQGPYGPSAAAAAAAAAGGYGPGAGQQGPGSQGPGSGGQQGPGGQPYGPSAAAAAAAAAGGYGPG AGQQGPGSGGQQGPGGQGPYGSGQQGPGGAGQQGPGGQGPYGPAAAAAAAAAGGYGPGAGQQGPGGAGQQGPGGQGPGG QGPYGPGAGQQGPGSQGPGSGGQQGPGGQPYGPSAAAAAAAAAGGYGPGAGQRSQGPGGQGPYGPGAGQQGPGSQGPGSG GQQGPGGQGPYGPSAAAAAAAAAGGYGPGAGQQGPGSQGPGSGGQQGPGGQPYGPAAAAAAAAVGGYGPGAGQQGPGSQG PGSGGQQGPGGQGPYGPSAAAAAAAAAGGYGPGAGQQGPGSQGPGSGGQQGPGGQPYGPSAAAAAAAAAGGYGPGAGQQP GSGGQQGPGGQGPYGSGQQGPGGAGQQGPGGQGPYGPAAAAAAAAAGGYGPGAGQQGPGGAGQQGPGSQGPGGQGPYGP GAGQQGPGSQGPGSGGQQGPGGQGPYGPSAAAAAAAAAGGYGPGAGQRSQGPGGQGPYGPGAGQQGPGSQGPGSGGQQGPG GQGPYGPSAAAAAAAAAGGYGPGAGQQGPGSQGPGSGGQQGPGGQPYGPAAAAAAAAVGGYGPGAGQQGPGSQGPGSGGQ QGPGGQGPYGPSAAAAAAAAAGGYGPGAGQQGPGSQGPGSGGQQGPGGQPYGPSAAAAAAAA |

In some embodiments, the silk or silk or silk-like proteins comprise one or more repeat units comprising SEQ ID NO: 17. This repeat unit contains 6 quasi-repeat units. The quasi-repeat unit can be concatenated 2, 3, 4, 5, 6, 7, 8, 9, 10, 11, 12, 13, 14, 15, 16, 17, 18, 19, or 20 times to form polypeptide molecules from about 50 kDal to about 1,000 kDal. This repeat unit also contains poly-alanine regions related to nano-crystalline regions, and glycine-rich regions related to beta-turn containing less-crystalline regions.

Non-limiting examples of additional suitable silk or silk or silk-like proteins are provided, for example, in International Patent Publication WO/2016/201369, published Dec. 15, 2016; U.S. patent application 62/394,683, filed Sep. 14, 2016; U.S. patent application Ser. No. 15/705,185, filed Sep. 14, 2017, U.S. publication US20160222174, published Aug. 4, 2016; International Patent Publication WO2016/149414, published Mar. 16, 2016; International Patent Publication WO 2014/066374, published Jan. 5, 2014, and International Patent Publication WO 2015/042164, published Mar. 26, 2015, each of which are hereby incorporated by reference in its entirety.

Typically, operable linkage of proteins with secretion signals requires removal of start codons of the polynucleotide sequences encoding the proteins.

Other Components

In some embodiments, the polynucleotide sequences comprised in the expression constructs further encode tag peptides or polypeptides operably linked to the C-termini of the proteins. Such tag peptides or polypeptides can aid in purification of the recombinant proteins. Non-limiting examples of tag peptides or polypeptides include affinity tags (i.e., peptides or polypeptides that bind to certain agents or matrices), solubilization tags (i.e., peptides or polypeptides that assist in proper folding of proteins and prevent precipitation), chromatography tags (i.e., peptides or polypeptides that alter the chromatographic properties of a protein to afford different resolution across a particular separation techniques), epitope tags (i.e., peptides or polypeptides that are bound by antibodies), fluorescence tags, chromogenic tags, enzyme substrate tags (i.e., peptides or polypeptides that are the substrates for specific enzymatic reactions), chemical substrate tags (i.e., peptides or polypeptides that are the substrates for specific chemical modifications), or combinations thereof. Non-limiting examples of suitable affinity tags include maltose binding protein (MBP), glutathione-S-transferase (GST), poly(His) tag, SBP-tag, Strep-tag, and calmodulin-tag. Non-limiting examples of suitable solubility tags include thioredoxin (TRX), poly(NANP), MBP, and GST. Non-limiting examples of chromatography tags include polyanionic amino acids (e.g., FLAG-tag) and polyglutamate tag. Non-limiting examples of epitope tags include V5-tag, VSV-tag, Myc-tag, HA-tag, E-tag, NE-tag, Ha-tag, Myc-tag, and FLAG-tag. Non-limiting examples of fluorescence tags include green fluorescent protein (GFP), blue fluorescent protein (BFP), cyan fluorescent protein (CFP), yellow fluorescent protein (YFP), orange fluorescent protein (OFP), red fluorescent protein (RFP), and derivatives thereof. Non-limiting examples of enzyme substrate tags include peptides or polypeptides comprising a lysine within a sequence suitable for biotinilation (e.g., AviTag, Biotin Carboxyl Carrier Protein [BCCP]). Non-limiting examples of chemical substrate tags include substrates suitable for reaction with FIAsH-EDT2. The fusion of the C-terminal tag peptide or polypeptide to the recombinant proteins can be cleavable (e.g., by TEV protease, thrombin, factor Xa, or enteropeptidase) or non-cleavable.

In some embodiments, the polynucleotide sequences comprised in the expression constructs further encode linker peptides operably linked between the proteins and the recombinant secretion signals. The linker peptides can have various sizes. In some such embodiments, the polynucleotide sequences that encode the linker peptides comprise restriction enzyme sites to permit replacement or addition of other polynucleotide sequences.

The expression constructs may further comprise promoters that are operably linked to the polynucleotide sequences encoding the proteins that are operably linked to the recombinant secretion signals such that they drive the transcription of the polynucleotide sequences. The promotors may be constitutive promoters or inducible promoters. Induction may, for example, occur via glucose repression, galactose induction, sucrose induction, phosphate repression, thiamine repression, or methanol induction. Suitable promoters are promoters that mediate expression of proteins in the recombinant host cells provided herein. Non-limiting examples of suitable promoters include the alcohol oxidase (AOX1) promoter of *Pichia pastoris* (pAOX1), glyceraldehyde-3-phosphate dehydrogenase (GAP) promoter of *Pichia pastoris* (pGAP), YPT1 promoter, 3-phosphoglycerate kinase 1 (PGK1) promoter of *Saccharomyces cerevisae* (pPKG1), SSA4 promoter, HSP82 promoter, GPM1 promoter, KAR2 promoter, triose phosphate isomerase 1 (TPI1) promoter of *Pichia pastoris* (pTPI1), enolase 1 (ENO1) promoter of *Pichia pastoris* (pENO1), PETS promoter, PEX8 (PER3) promoter, AOX2 promoter, AOD promoter, THI11 promoter, DAS promoter, FLD1 promoter, PHO89 promoter, CUP1 promoter, GTH1 promoter, ICL1 promoter, TEF1 promoter, LAC4-PBI promoter, T7 promoter, TAC promoter, GCW14 promoter, GAL1 promoter, λPL promoter, λPR promoter, beta-lactamase promoter, spa promoter, CYC1 promoter, TDH3 promoter, GPD promoter, translation initiation factor 1 (TEF1) promoter of *Saccharomyces cerevisiae*, ENO2 promoter, PGL1 promoter, GAP promoter, SUC2 promoter, ADH1 promoter, ADH2 promoter, HXT7 promoter, PHO5 promoter, and CLB1 promoter. Additional promoters that can be used are known in the art.

The expression constructs may further comprise terminators that are operably linked to the polynucleotide sequences encoding the proteins that are operably linked to the recombinant secretion signals such that they effect termination of transcription of the polynucleotide sequences. Suitable terminators are terminators that terminate transcription in the recombinant host cells provided herein. Non-limiting examples of suitable terminators include the AOX1 terminator of *Pichia pastoris* (tAOX1), PGK1 terminator, and TPS1 terminator. Additional terminators are known in the art.

Recombinant Vectors

The recombinant vectors provided herein comprise expression constructs provided herein. In some embodiments, the recombinant vectors comprise multiple expression constructs (e.g., 2, 3, 4, 5, etc.). In some such embodiments, the expression constructs are identical. In other such embodiments, at least 2 of the expression constructs are not identical. In embodiments in which at least 2 of the expression constructs are not identical, the at least 2 expression constructs may differ from each other in the proteins, recombinant secretion signals, promoters, terminators, and/or other components they encode.

The recombinant vectors may further comprise elements suitable for propagation of the recombinant vectors in recombinant host cells. Non-limiting examples of such other elements include origins of replication and selection markers (e.g., antibiotic resistance genes, auxotrophic markers). Origins of replication and selection markers are known in the art. In various embodiments, the origins of replications are bacterial or yeast origins of replication. In some embodiments, the origins of replication are *Pichia* autonomously replicating sequences (PARS). In some embodiments, the selection markers are drug resistant markers. A drug resistant maker enables cells to detoxify an exogenously added drug that would otherwise kill the cell. Illustrative examples of drug resistant markers include but are not limited to those for resistance to antibiotics such as ampicillin, tetracycline, kanamycin, bleomycin, streptomycin, hygromycin, neomycin, Zeocin™, and the like. In other embodiments, the selection markers are auxotrophic markers. An auxotrophic marker allows cells to synthesize an essential component (usually an amino acid) while grown in media that lacks that essential component. Selectable auxotrophic markers include, for example, hisD, which allows growth in histidine-free media in the presence of histidinol. Other selection markers include a bleomycin-resistance gene, a metallothionein gene, a hygromycin B-phosphotransferase gene, the AURI gene, an adenosine deaminase gene, an aminoglycoside phosphotransferase gene, a dihydrofolate reductase gene, a thymidine kinase gene, and a xanthine-guanine phosphoribosyltransferase gene.

The recombinant vectors may further comprise targeting sequences that can direct integration of the expression constructs to specific locations in the genome of host cells. Non-limiting examples of such targeting sequences are polynucleotide sequences that are homologous to polynucleotide sequences comprised in the genome of host cells. In some embodiments, the targeting sequences are homologous to repetitive elements in the genome of host cells. In some embodiments, the targeting sequences are homologous to transposable elements in the genome of host cells.

Recombinant Host Cells

The recombinant host cells provided herein are cells that comprise expression constructs provided herein. The recombinant host cells can be of mammalian, plant, algae, fungi, or microbe origin.

Non-limiting examples of suitable fungi include methylotrophic yeast, filamentous yeast, *Arxula adeninivorans, Aspergillus niger, Aspergillus niger* var. awamori, *Aspergillus oryzae, Candida etchellsii, Candida guilliermondii, Candida humilis, Candida lipolytica, Candida pseudotropicalis, Candida utilis, Candida versatilis, Debaryomyces hansenii, Endothia parasitica, Eremothecium ashbyii, Fusarium moniliforme, Hansenula polymorpha, Kluyveromyces lactis, Kluyveromyces marxianus, Kluyveromyces thermotolerans, Morteirella vinaceae* var. raffinoseutilizer, *Mucor miehei, Mucor miehei* var. *Cooney et Emerson, Mucor pusillus Lindt, Penicillium roquefortii, Pichia methanolica, Pichia (Komagataella) pastoris, Pichia (Scheffersomyces) stipitis, Rhizopus niveus, Rhodotorula* sp., *Saccharomyces bayanus, Saccharomyces beticus, Saccharomyces cerevisiae, Saccharomyces chevalieri, Saccharomyces diastaticus, Saccharomyces ellipsoideus, Saccharomyces exiguus, Saccharomyces florentinus, Saccharomyces fragilis, Saccharomyces pastorianus, Saccharomyces pombe, Saccharomyces sake, Saccharomyces uvarum, Sporidiobolus johnsonii, Sporidiobolus salmonicolor, Sporobolomyces roseus, Trichoderma reesi, Xanthophyllomyces dendrorhous, Yarrowia lipolytica, Zygosaccharomyces rouxii*, and derivatives and crosses thereof.

Non-limiting examples of suitable microbes include *Acetobacter suboxydans, Acetobacter xylinum, Actinoplane missouriensis, Arthrospira platensis, Arthrospira maxima, Bacillus cereus, Bacillus coagulans, Bacillus licheniformis, Bacillus stearothermophilus, Bacillus subtilis, Escherichia coli, Lactobacillus acidophilus, Lactobacillus bulgaricus, Lactobacillus reuteri, Lactococcus lactis, Lactococcus lactis* Lancefield Group N, *Leuconostoc citrovorum, Leuconostoc dextranicum, Leuconostoc mesenteroides* strain NRRL B-512(F), *Micrococcus lysodeikticus, Spirulina, Streptococcus cremoris, Streptococcus lactis, Streptococcus lactis* subspecies diacetylactis, *Streptococcus thermophilus, Streptomyces chattanoogensis, Streptomyces griseus, Streptomyces natalensis, Streptomyces olivaceus, Streptomyces olivochrornogenes, Streptomyces rubiginosus, Xanthomonas campestris*, and derivatives and crosses thereof.

Additional strains that can be used as recombinant host cells are known in the art. It should be understood that the term "recombinant host cell" is intended to refer not only to the particular subject cell but to the progeny of such a cell. Because certain modifications may occur in succeeding generations due to either mutation or environmental influences, such progeny may not, in fact, be identical to the parent cell, but is still included within the scope of the term "recombinant host cell" as used herein.

In some embodiments, the expression constructs are stably integrated within the genome (e.g., a chromosome) of the recombinant host cells, e.g., via homologous recombination or targeted integration. Non-limiting examples of suitable sites for genomic integration include the Ty 1 loci in the *Saccharomyces cerevisiae* genome, the rDNA and HSP82 loci in the *Pichia pastoris* genome, and transposable elements that have copies scattered throughout the genome of the recombinant host cells. In other embodiments, the expression constructs are not stably integrated within the genome of the recombinant host cells but rather are maintained extrachromosomally (e.g., on a plasmid).

Production of recombinant proteins can be influenced by the number of copies of the expression constructs provided herein that are comprised in the recombinant host cells and/or the rate of transcription of the polynucleotide sequences comprised in the expression constructs. In some embodiments, the recombinant host cells comprise a single expression construct. In other embodiments, the recombinant host cells comprise 2 or more (e.g., 3, 4, 5, or more) expression constructs. In some embodiments, the recombinant host cells comprise expression constructs that comprise polynucleotide sequences that are operably linked to strong promoters. Non-limiting examples of strong promoters include the pGCW14 promoter of *Pichia pastoris*. In some embodiments, the recombinant host cells comprise expression constructs that comprise polynucleotide sequences that are operably linked to medium promoters. Non-limiting examples of such medium promoters include the pGAP promoter of *Pichia pastoris*. In some embodiments, the recombinant host cells comprise expression constructs that comprise polynucleotide sequences that are operably linked to weak promoters.

The recombinant secretion signals provided herein provide high secreted yields of recombinant proteins. Accordingly, in various embodiments, the recombinant host cells produce secreted yields of the protein encoded by the polynucleotide sequences comprised in the expression constructs of at least 1%, 5%, 10%, 20%, or 30%; from 1% to 100%, 90%, 80%, 70%, 60%, 50%, 40%, 30%, 20%, or 10%; from 10% to 100%, 90%, 80%, 70%, 60%, 50%, 40%, 30%, or 20%; from 20% to 100%, 90%, 80%, 70%, 60%, 50%, 40%, or 30%; from 30% to 100%, 90%, 80%, 70%, 60%, 50%, or 40%; from 40% to 100%, 90%, 80%, 70%, 60%, or 50%; from 50% to 100%, 90%, 80%, 70%, or 60%;

from 60% to 100%, 90%, 80%, or 70%; from 70% to 100%, 90%, or 80%; from 80% to 100%, or 90%; or from 90% to 100% by weight of total yields of the protein. The identities of recombinant proteins produced can be confirmed by HPLC quantification, Western blot analysis, polyacrylamide gel electrophoresis, and 2-dimensional mass spectroscopy (2D-MS/MS) sequence identification.

Fermentations

The fermentations provided herein comprise recombinant host cells provided herein and culture media suitable for growing the recombinant host cells.

The fermentations are obtained by culturing the recombinant host cells in culture media that provide nutrients needed by the recombinant host cells for cell survival and/or growth. Such culture media typically contain an excess carbon source. Non-limiting examples of suitable carbon sources include monosaccharides, disaccharides, polysaccharides, alcohols, and combinations thereof. Non-limiting examples of suitable monosaccharides include glucose, galactose, mannose, fructose, ribose, xylose, arabinose, ribose, and combinations thereof. Non-limiting examples of suitable disaccharides include sucrose, lactose, maltose, tehalose, cellobiose, and combinations thereof. Non-limiting examples of suitable polysaccharides include raffinose, starch, glycogen, glycan, cellulose, chitin, and combinations thereof. Non-limiting examples of suitable alcohols include methanol and glycol.

The recombinant secretion signals provided herein provide high secreted yields of recombinant proteins. Accordingly, in various embodiments, the fermentations provided herein comprise at least 1%, 5%, 10%, 20%, or 30%; from 1% to 100%, 90%, 80%, 70%, 60%, 50%, 40%, 30%, 20%, or 10%; from 10% to 100%, 90%, 80%, 70%, 60%, 50%, 40%, 30%, or 20%; from 20% to 100%, 90%, 80%, 70%, 60%, 50%, 40%, or 30%; from 30% to 100%, 90%, 80%, 70%, 60%, 50%, or 40%; from 40% to 100%, 90%, 80%, 70%, 60%, or 50%; from 50% to 100%, 90%, 80%, 70%, or 60%; from 60% to 100%, 90%, 80%, or 70%; from 70% to 100%, 90%, or 80%; from 80% to 100%, or 90%; or from 90% to 100% by weight of total yields of the recombinant proteins as secreted recombinant proteins. In some embodiments, the culture media of the fermentations comprise at least 0.1 g/L, at least 0.5 g/L, at least 1 g/L, at least 2 g/L, at least 5 g/L, at least 7 g/L, at least 10 g/L, at least 15 g/L, or at least 20 g/L; from 0.1 g/L to 30 g/L, to 25 g/L, to 20 g/L, to 15 g/L, to 10 g/L, to 7 g/L, to 5 g/L, to 2 g/L, to 1 g/L, or to 0.5 g/L; from 0.5 g/L to 30 g/L, to 25 g/L, to 20 g/L, to 15 g/L, to 10 g/L, to 7 g/L, to 5 g/L, to 2 g/L, or to 1 g/L; from 1 g/L to 30 g/L, to 25 g/L, to 20 g/L, to 15 g/L, to 10 g/L, to 7 g/L, to 5 g/L, or to 2 g/L; from 2 g/L to 30 g/L, to 25 g/L, to 20 g/L, to 15 g/L, to 10 g/L, to 7 g/L, or to 5 g/L; from 5 g/L to 30 g/L, to 25 g/L, to 20 g/L, to 15 g/L, to 10 g/L, or to 7 g/L; from 7 g/L to 30 g/L, to 25 g/L, to 20 g/L, to 15 g/L, or to 10 g/L; from 10 g/L to 30 g/L, to 25 g/L, to 20 g/L, or to 15 g/L; from 15 g/L to 30 g/L, to 25 g/L, or to 20 g/L; from 20 g/L to 30 g/L, or to 25 g/L; or from 25 g/L to 30 g/L of the recombinant proteins produced by the recombinant host cells.

Methods of Producing High Secreted Yields of Recombinant Proteins

Provided herein are methods for producing high secreted yields of recombinant proteins. The methods are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y., 1989; Ausubel et al. Current Protocols in Molecular Biology, Greene Publishing Associates, 1992, and Supplements to 2002); Harlow and Lane, Antibodies: A Laboratory Manual, Cold Spring Harbor Laboratory Press, Cold Spring Harbor, N.Y., 1990; Taylor and Drickamer, Introduction to Glycobiology, Oxford Univ. Press, 2003; Worthington Enzyme Manual, Worthington Biochemical Corp., Freehold, N.J.; Handbook of Biochemistry: Section A Proteins, Vol I, CRC Press, 1976; Handbook of Biochemistry: Section A Proteins, Vol II, CRC Press, 1976; Essentials of Glycobiology, Cold Spring Harbor Laboratory Press, 1999.

The methods provided herein comprise the step of culturing recombinant host cells provided herein in culture media under conditions suitable for obtaining the fermentations provided herein (step 1003 in FIG. 1). Suitable culture media for use in these methods are known in the art, as are suitable culture conditions. Details of culturing yeast host cells, for example, are described in Idiris et al. (2010) Appl. Microbiol. Biotechnol. 86:403-417; Zhang et al. (2000) Biotechnol. Bioprocess. Eng. 5:275-287; Zhu (2012) Biotechnol. Adv. 30:1158-1170; and Li et al. (2010) MAbs 2:466-477.

In some embodiments, the methods further comprise the step of constructing expression constructs and/or recombinant vectors provided herein (step 1001 in FIG. 1). Methods for constructing expression construct and recombinant vectors are known in the art. In some embodiments, the expression constructs and/or recombinant vectors are synthetically generated. In other embodiments, the expression constructs and/or recombinant vectors are isolated or PCR amplified by standard procedures from organisms, cells, tissues, or plasmid constructs. In some embodiments, the expression constructs and/or recombinant vectors are codon-optimized for expression in particular host cells.

In some embodiments, the methods comprise the step of balancing expression of the recombinant proteins (e.g., by increasing or reducing the number of polynucleotide sequences and/or the strengths of the promoters that are operably linked to the polynucleotide sequences) and efficiency of secretion of the recombinant proteins (e.g., by choosing specific recombinant secretion signals).

In some embodiments, the methods further comprise the step of transforming cells with expression constructs or recombinant vectors provided herein to obtain recombinant host cells provided herein (step 1002 in FIG. 1). For such transformations, the recombinant vectors can be circularized or be linear. Methods for transforming cells are well-known in the art. Non-limiting examples of such methods include calcium phosphate transfection, dendrimer transfection, liposome transfection (e.g., cationic liposome transfection), cationic polymer transfection, electroporation, cell squeezing, sonoporation, optical transfection, protoplast fusion, impalefection, hyrodynamic delivery, gene gun, magnetofection, spheroblast generation, polyethylene glycol (PEP) treatment, and viral transduction. One skilled in the art is able to select one or more suitable methods for transforming cells with expression constructs or recombinant vectors provided herein based on the knowledge in the art that certain techniques for introducing vectors work better for certain types of cells. Recombinant host cell transformants comprising expression constructs or recombinant vectors provided herein can be readily identified, e.g., by virtue of expressing drug resistance or auxotrophic markers encoded by the recombinant vectors that permit selection for or against growth of cells, or by other means (e.g., detection of light emitting peptide comprised in the expression constructs or recombinant vectors, molecular analysis of individual recombinant host cell colonies [e.g., by restriction enzyme mapping, PCR amplification, or sequence analysis of isolated extrachromosomal vectors or chromosomal integration sites]).

In some embodiments, the methods further comprise the step of extracting the secreted recombinant proteins from fermentations provided herein (step 1004 in FIG. 1). Extraction can occur by a variety of methods known in the art for purifying secreted proteins. Common steps in such methods include centrifugation at speeds that cause the pelleting of cells and removal of cell pellets comprising the recombinant host cells and cell debris, followed by precipitation of the recombinant proteins using precipitants (e.g., ammonium sulfate at 5-60% saturation; followed by centrifugation) or affinity separation (e.g., by immunological interaction with antibodies that bind specifically to the recombinant proteins or their C-terminal tags [e.g., FLAG, hemagglutinin], or via binding to nickel columns for isolation of polypeptides tagged with 6 to 8 histidine residues (SEQ ID NO: 154)). The suspended recombinant proteins can be dialyzed to remove the dissolved salts. Additionally, the dialyzed recombinant proteins can be heated to denature other proteins, and the denatured proteins can be removed by centrifugation.

EXAMPLES

Example 1: Generation of *Pichia pastoris* Recombinant Host Cells that Produce High Secreted Yields of Silk-Like Proteins

*Pichia pastoris* (*Komagataella phaffii*) recombinant host cells that secrete a silk-like protein were generated by transforming a HIS+ derivative of GS115 (NRRL Y15851) with various recombinant vectors.

Figure 2:
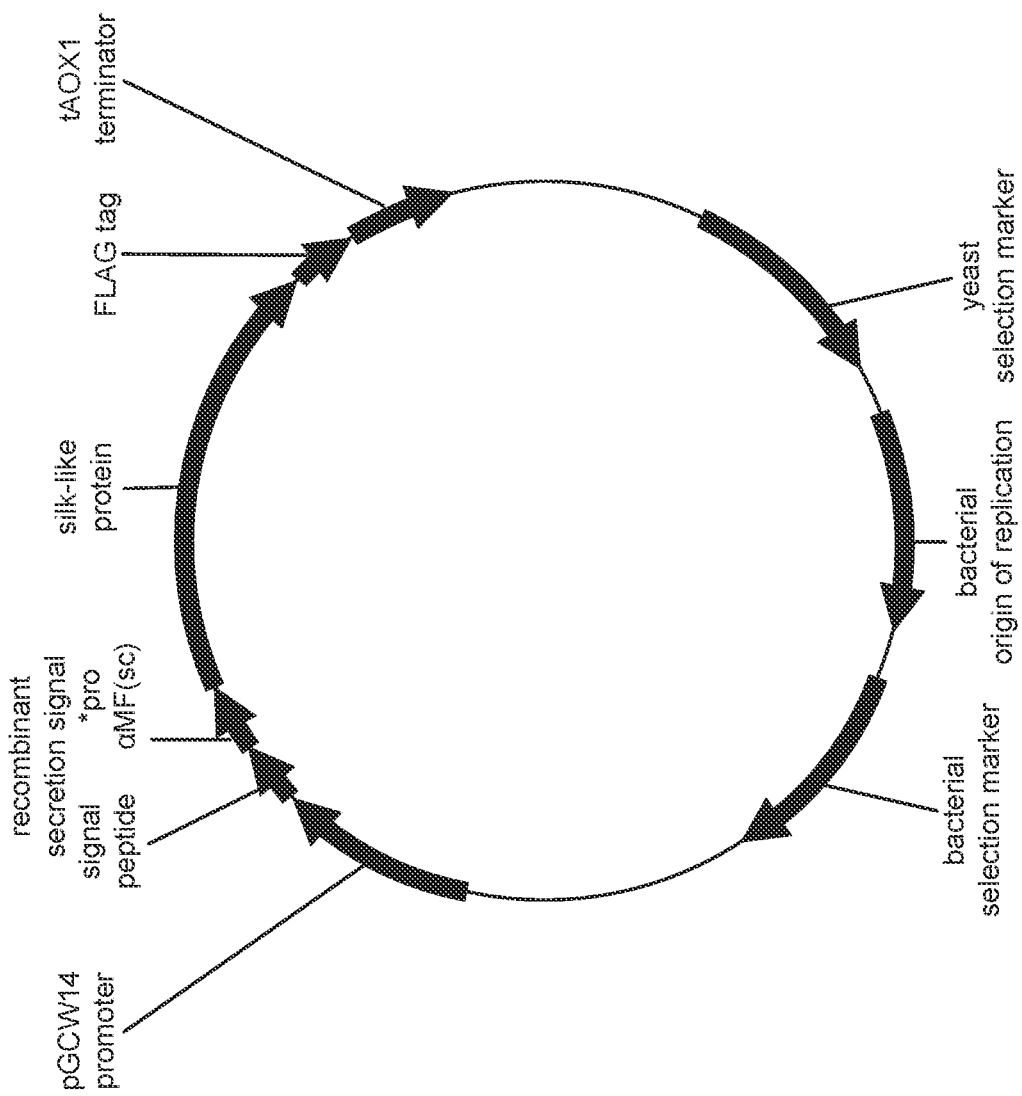
FIG. 2 is an illustrative map of a recombinant vector that comprises a polynucleotide sequence that encodes a silk-like protein operably linked to an N-terminal recombinant secretion signal comprising a functional variant of the leader peptide of the α-mating factor of *Saccharomyces cerevisiae* (*pro-αMF(sc)) and a signal peptide. The amino acid sequences for the various signal peptides and recombinant secretion signals used are given in Tables A and B.

The recombinant vectors (see FIG. 2) comprised an expression construct that comprised a polynucleotide sequence encoding the silk-like protein (SEQ ID NO: 114) operably linked to various N-terminal recombinant secretion signals. The recombinant secretion signals consisted of an N-terminal signal peptide operably linked to *pro-αMF(sc) (SEQ ID NO:2) or to pro-EPX1(pp) (SEQ ID NO: 144). The silk-like protein was further operably linked to a C-terminal FLAG-tag. Each of the polynucleotide sequences was flanked by a promoter (pGCW14) and a terminator (tAOX1 pA signal). The recombinant vectors further comprised a targeting region that directed integration of the expression construct to the region immediately 3' of the ICL1, HSP82, or THI13 loci in the *Pichia pastoris* genome, dominant resistance markers for selection of bacterial and yeast transformants, and a bacterial origin of replication.

The recombinant vectors were transformed into the *Pichia pastoris* host cells via electroporation to generate recombinant host strains. Transformants were plated on YPD agar plates supplemented with antibiotics, and incubated for 48 hours at 30° C.

Clones from each final transformation were inoculated into 400 μL of Buffered Glycerol-complex Medium (BMGY) in 96-well blocks, and incubated for 48 hours at 30° C. with agitation at 1,000 rpm. Following the 48-hour incubation, 4 μL of each culture was used to inoculate 400 μL of minimal media in 96-well blocks, which were then incubated for 48 hours at 30° C.

Guanidine thiocyanate was added to a final concentration of 2.5 M to the cell cultures to extract the recombinant protein for measurement by ELISA. After a 5 min incubation, solutions were centrifuged and the supernatant was sampled.

Figure 3:
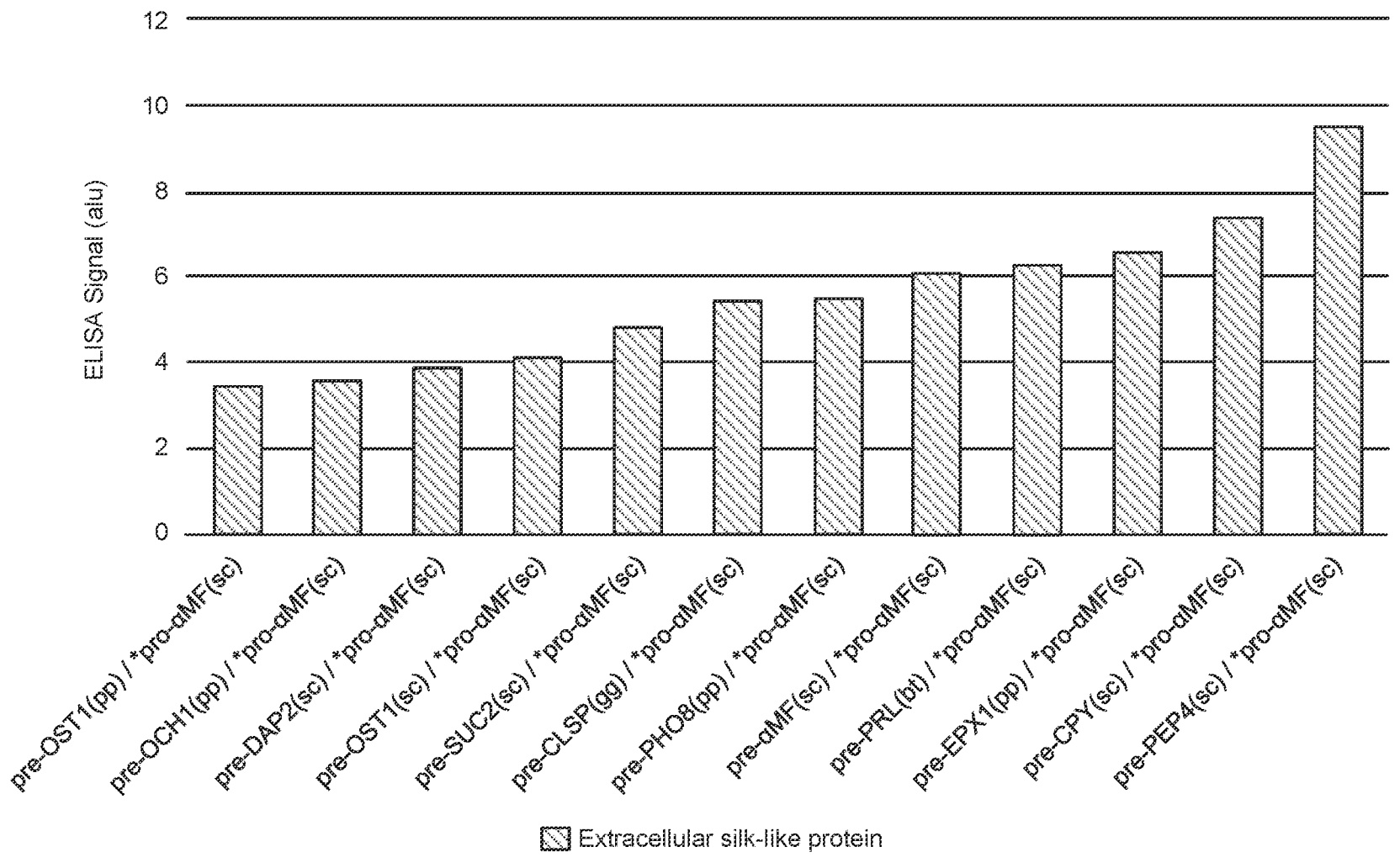

As shown in FIG. 3, a number of recombinant secretion signals produced higher secreted yields of the silk-like protein than the pre-OST1(sc)/*pro-αMF(sc) recombinant secretion signal and/or the pre-αMF(sc)/*pro-αMF(sc) secretion signal, whereas others produced lower secreted yields.

Figure 4:
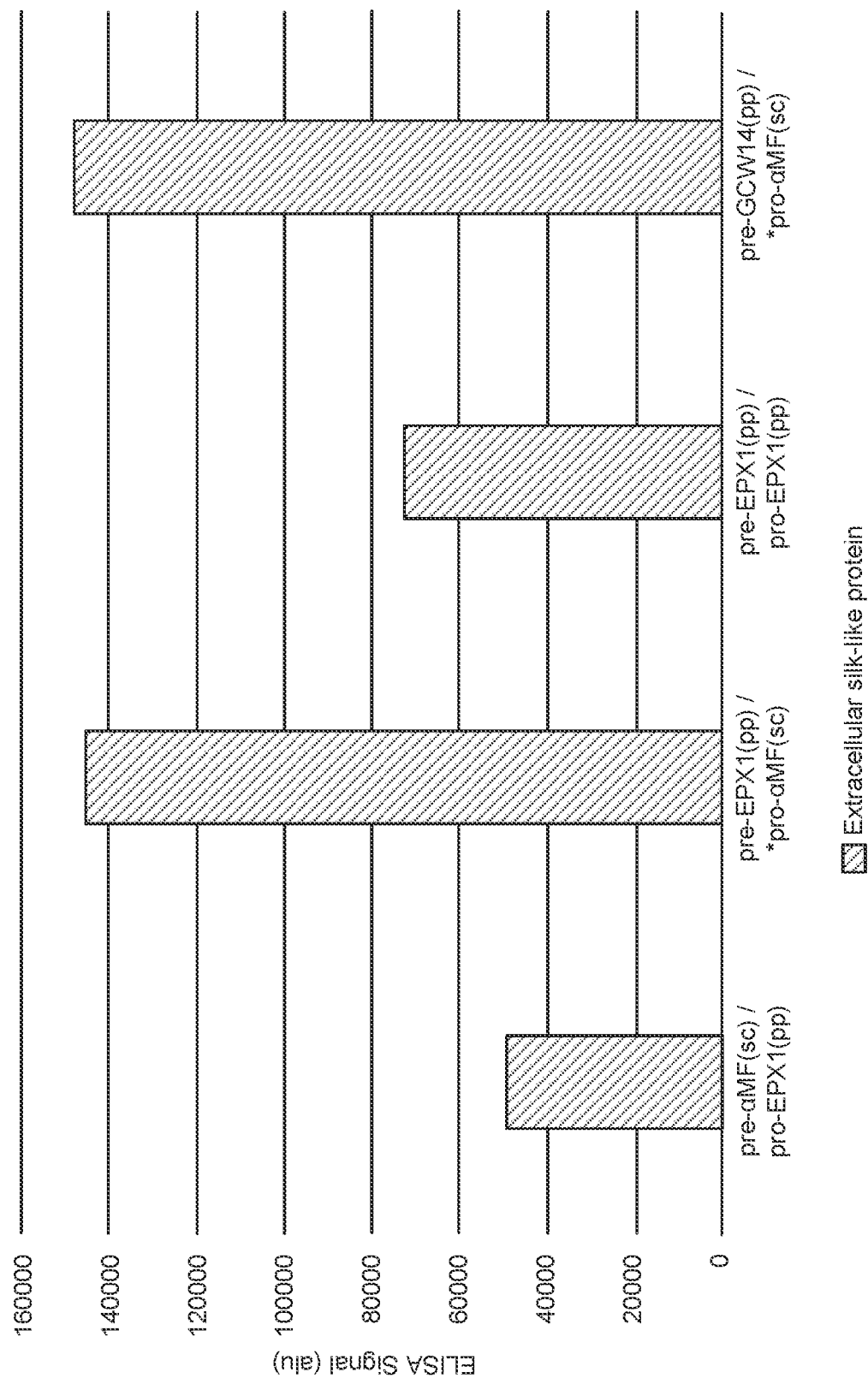

As shown in FIG. 4, secreted yields of the silk-like protein were significantly higher when the recombinant secretion signals comprised pro-αMF(sc) rather than pro-EPX1(pp). As further shown in FIG. 4, slightly higher secreted yields were obtained with the recombinant secretion signal pre-GCW14(pp)/*pro-αMF(sc) than with the recombinant secretion signal pre-EPX1(pp)/*pro-αMF(sc).

Figure 5:
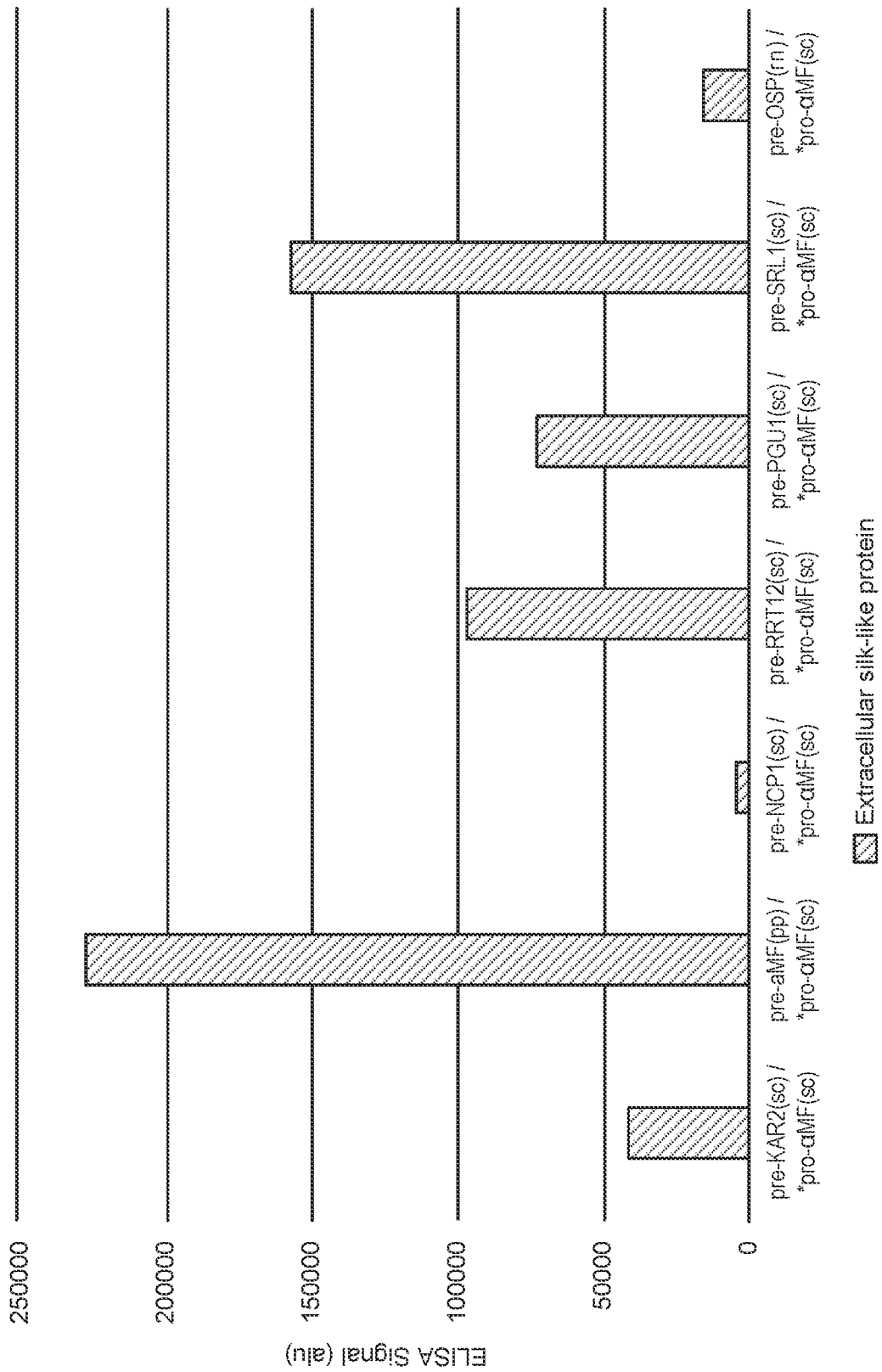
Figure 6:
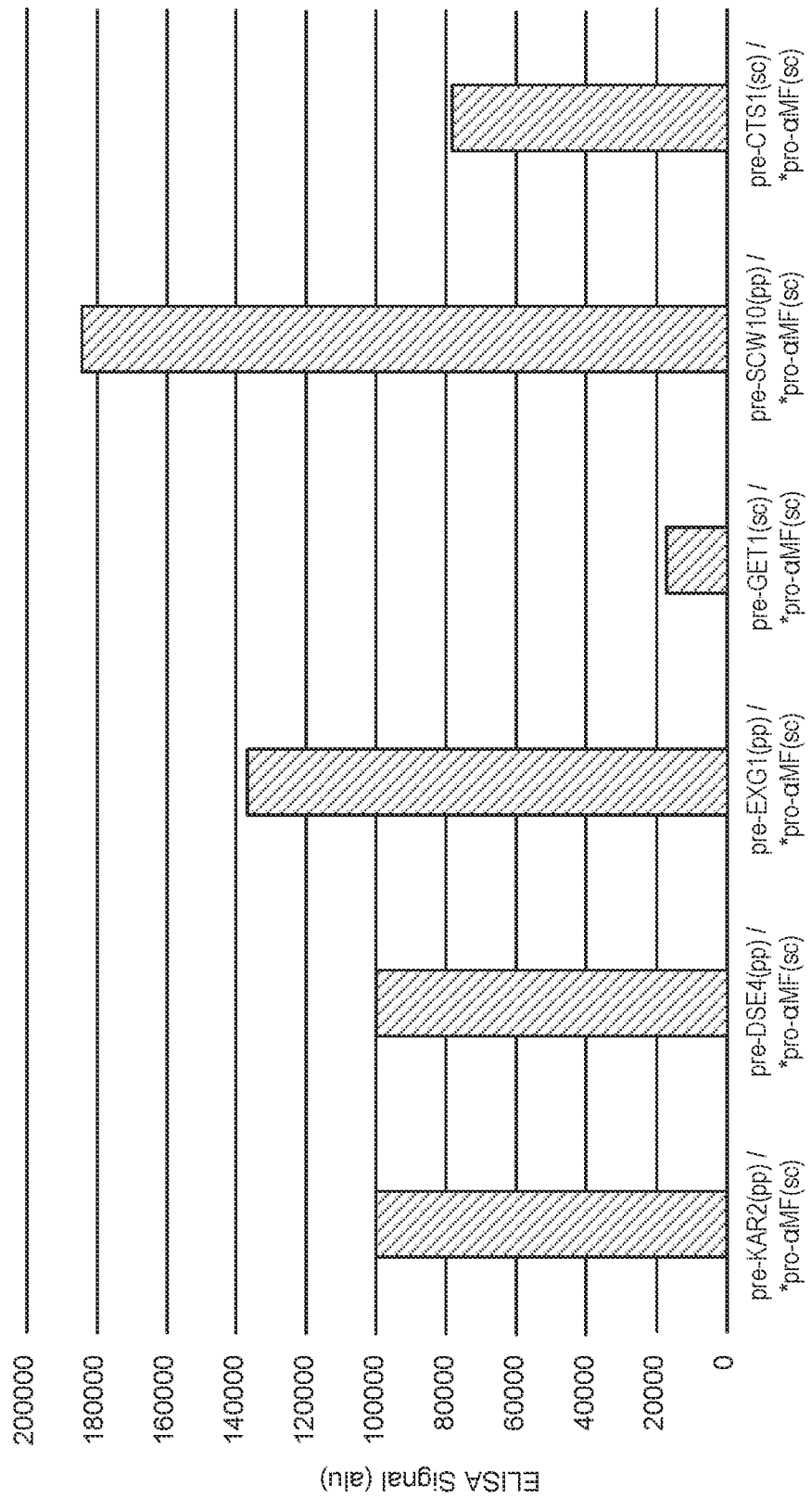

FIGS. 5 and 6 show additional recombinant secretion signals provided herein that achieve secreted yields of the silk-like protein.

Example 2: Generation of *Pichia pastoris* Recombinant Host Cells that Produce High Secreted Yields of Alpha-Amylase or Green Fluorescent Protein

*Pichia pastoris* (*Komagataella phaffii*) recombinant host cells that secrete either an alpha-amylase or green fluorescent protein were generated by transforming a HIS+ derivative of GS115 (NRRL Y15851) with various recombinant vectors.

Figure 7:
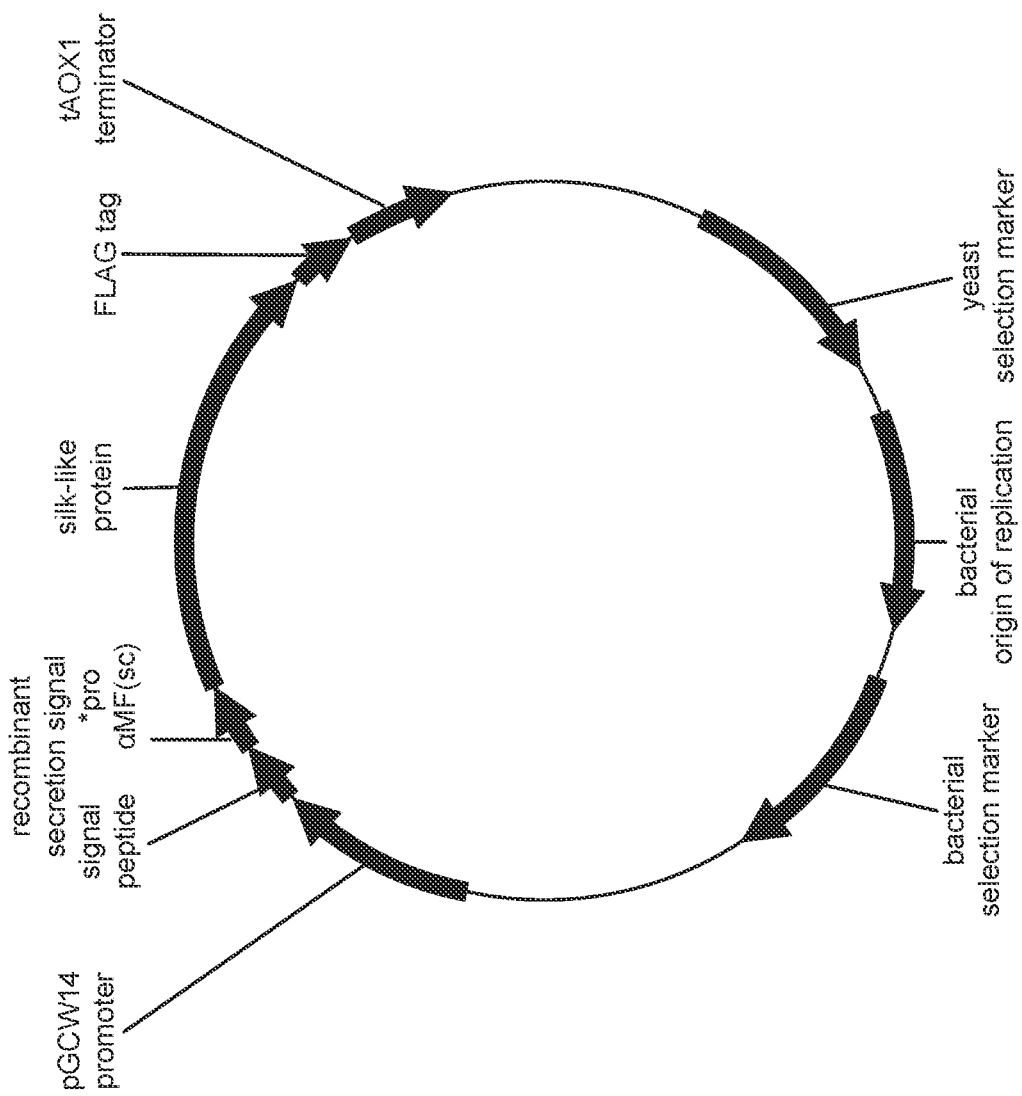
FIG. 7 is a diagram of a recombinant vector comprising an expression construct for expressing a polypeptide with recombinant secretion signals, according to an embodiment of the invention.

The recombinant vectors (see FIG. 7) comprised an expression construct that comprised a polynucleotide sequence encoding either alpha-amylase (SEQ ID NO: 145) or green fluorescent protein (SEQ ID NO: 146) operably linked to various N-terminal recombinant secretion signals. The recombinant secretion signals consisted of an N-terminal signal peptide operably linked to *pro-αMF(sc) (SEQ ID NO:2). The alpha-amylase or green fluorescent protein was further operably linked to a C-terminal FLAG-tag. Each of the polynucleotide sequences was flanked by a promoter (pGCW14) and a terminator (tAOX1 pA signal). The recombinant vectors further comprised a targeting region that directed integration of the expression construct to the region immediately 3' of the THI4 locus in the *Pichia pastoris* genome, dominant resistance markers for selection of bacterial and yeast transformants, and a bacterial origin of replication.

The recombinant vectors were transformed into the *Pichia pastoris* host cells via electroporation to generate recombinant host strains. Transformants were plated on YPD agar plates supplemented with antibiotics, and incubated for 48-96 hours at 30° C.

Clones from each final transformation were inoculated into 400 μL of Buffered Glycerol-complex Medium (BMGY) in 96-well blocks, and incubated for 48 hours at 30° C. with agitation at 1,000 rpm. Following the 48-hour incubation, 4 μL of each culture was used to inoculate 400 μL of minimal media in 96-well blocks, which were then incubated for 48 hours at 30° C.

Guanidine thiocyanate was added to a final concentration of 2.5 M to the cell cultures to extract the recombinant protein for measurement by ELISA. After a 5 min incubation, solutions were centrifuged and the supernatant was sampled.

Figure 8:
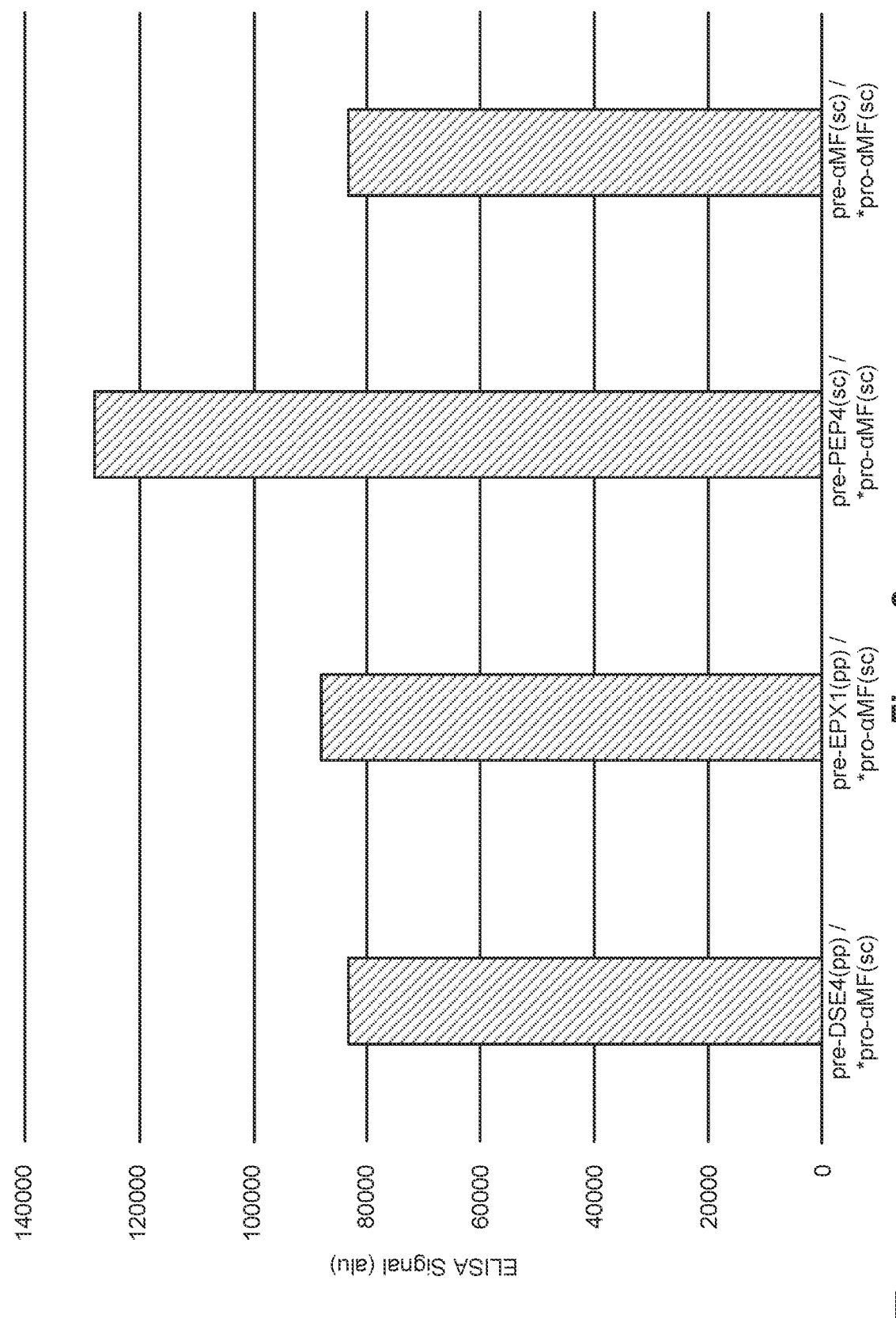
FIG. 8 illustrates secretion levels of alpha-amylase from *Pichia pastoris* transformed to express recombinant alpha-amylase with various recombinant secretion signals.

As shown in FIG. 8, the pre-EPX1(pp)/*pro-αMF(sc) and the pre-PEP4(sc)/*pro-αMF(sc) recombinant secretion signals produced higher secreted yields of amylase than the pre-αMF(sc)/*pro-αMF(sc) recombinant secretion signal while the pre-DSE4(pp)/*pro-αMF(sc) secretion signal produced roughly the same amount of secreted amylase.

Figure 9:
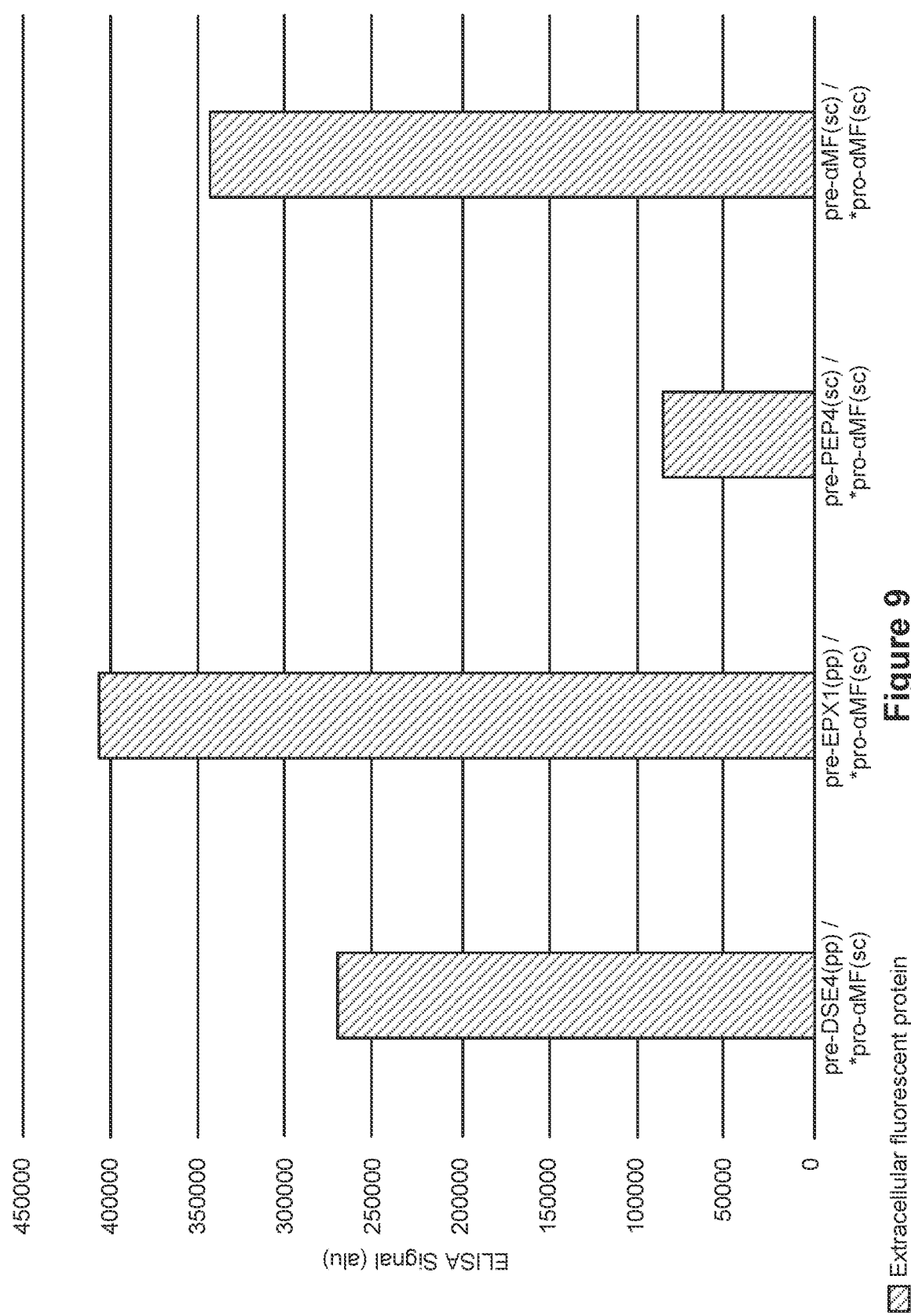
FIG. 9 illustrates secretion levels of fluorescent protein from *Pichia pastoris* transformed to express recombinant fluorescent protein with various recombinant secretion signals.

As shown in FIG. 9, the pre-EPX1(pp)/*pro-αMF(sc) recombinant secretion signal produced higher secreted yields of green fluorescent protein than the pre-αMF(sc)/*pro-αMF(sc) recombinant secretion signal, while the pre-PEP4(sc)/*pro-αMF(sc) and the pre-DSE4(pp)/*pro-αMF(sc) secretion signals produced less secreted fluorescent protein.

The foregoing description of the embodiments of the disclosure has been presented for the purpose of illustration; it is not intended to be exhaustive or to limit the scope of the invention.

In the examples, efforts have been made to ensure accuracy with respect to numbers used (e.g., amounts, temperatures, etc.), but some experimental error and deviation should, of course, be allowed for. The reagents employed in the examples are generally commercially available or can be prepared using commercially available instrumentation, methods, or reagents known in the art. The examples are not intended to provide an exhaustive description of the many different embodiments of the invention. Those of ordinary skill in the art will realize readily that many changes and modifications can be made to the embodiments presented in the examples without departing from the spirit or scope of the appended claims.

TABLE 4

Additional Sequences

| SEQ ID NO | Name | Amino Acid Sequence |
|---|---|---|
| 1 | pro-αMF(sc) | APVNTTTEDETAQIPAEAVIGYLDLEGDFDVAVLPFSNSTNNGLLFINTTIA SIAAKEEGVSLDKREAEA |
| 2 | *pro-αMF(sc) | APVNTTTEDETAQIPAEAVIGYSDLEGDFDVAVLPFSNSTNNGLLFINTTIA SIAAKEEGVSLEKREAEA |
| 115 | pre-αMF(sc)/ pro-αMF(sc) | MRFPSIFTAVLFAASSALAAPVNTTTEDETAQIPAEAVIGYLDLEGDFDVA VLPFSNSTNNGLLFINTTIASIAAKEEGVSLDKREAEA |
| 144 | pro-EPX1(pp) | APVAPAEEAANHLHKRAYYTDTTKTHTFTEVVTVYRT |
| 145 | alpha-amylase | ANLNGTLMQYFEWYMPNDGQHWKRLQNDSAYLAEHGITAVWIPPAYK GTS QDDVGYGAYDLYDLGEFHQKGTVRTKYGTKGELQSAINSLHSRDIN VYGDVVINHKGGADATEDVTAVEVDPADRNRVTSGEQRIKAWTHFQFP GRGSTYSDFKWHWYHFDGTDWDESRKLNRIYKFQGKAWDWEVSNVNG NYDYLMYADIDYDHPDATAEIKRWGTWYANELQLDGFRLDAVKHIKFSF LRDWVNHVREKTGKEMFTVAEYWQNDLGALENYLNKTNFNHSVFDVPL HYQFHAASTQGGGYDMRKLLNGTVVSKHPVKAVTFVDNHDTQPGQSLE STVQTWFKPLAYAFILTREAGYPQIFYGDMYGTKGASQREIPALKHKIEPI LKARIQYAYGAQHDYFDHHDIVGWTREGDSSVANSGLAALITDGPGGTK RMYVGRQNAGETWHDITGNRSDSVVINAEGWGEFHVNGGSVSIYVQR |
| 146 | green fluorescent protein | TALTEGAKLFEKEIPYITELEGDVEGMKFIIKGEGTGDATTGTIKAKYICTT GDLPVPWATLVSTLSYGVQCFAKYPSHIKDFFKSAMPEGYTQERTISFEG DGVYKTRAMVTYERGSIYNRVTLTGENFKKDGHILRKNVAFQCPPSILYI LPDTVNNGIRVEFNQAYDIEGVTEKLVTKCSQMNRPLAGSAAVHIPRYHH ITYHTKLSKDRDERRDHMCLVEVVKAVDLDTYQ |

SEQUENCE LISTING

```
Sequence total quantity: 154
SEQ ID NO: 1              moltype = AA  length = 70
FEATURE                   Location/Qualifiers
source                    1..70
                          mol_type = protein
                          organism = Saccharomyces cerevisiae
SEQUENCE: 1
APVNTTTEDE TAQIPAEAVI GYLDLEGDFD VAVLPFSNST NNGLLFINTT IASIAAKEEG  60
VSLDKREAEA                                                        70

SEQ ID NO: 2              moltype = AA  length = 70
FEATURE                   Location/Qualifiers
source                    1..70
                          mol_type = protein
                          organism = synthetic construct
SEQUENCE: 2
APVNTTTEDE TAQIPAEAVI GYSDLEGDFD VAVLPFSNST NNGLLFINTT IASIAAKEEG  60
VSLEKREAEA                                                        70
```

| | | |
|---|---|---|
| SEQ ID NO: 3<br>FEATURE<br>source | moltype = AA   length = 27<br>Location/Qualifiers<br>1..27<br>mol_type = protein<br>organism = Bos taurus | |
| SEQUENCE: 3<br>MDSKGSSQKG SRLLLLLVVS NLLLCSA | | 27 |
| SEQ ID NO: 4<br>FEATURE<br>source | moltype = AA   length = 18<br>Location/Qualifiers<br>1..18<br>mol_type = protein<br>organism = Gallus gallus | |
| SEQUENCE: 4<br>MRSLLILVLC FLPLAALG | | 18 |
| SEQ ID NO: 5<br>FEATURE<br>source | moltype = AA   length = 20<br>Location/Qualifiers<br>1..20<br>mol_type = protein<br>organism = Saccharomyces cerevisiae | |
| SEQUENCE: 5<br>MKAFTSLLCG LGLSTTLAKA | | 20 |
| SEQ ID NO: 6<br>FEATURE<br>source | moltype = AA   length = 46<br>Location/Qualifiers<br>1..46<br>mol_type = protein<br>organism = Pichia pastoris | |
| SEQUENCE: 6<br>MDSEPLLPNP NDSRKPANWR RIIKYISLTL AWIGIFSYVY IYHGTA | | 46 |
| SEQ ID NO: 7<br>FEATURE<br>source | moltype = AA   length = 22<br>Location/Qualifiers<br>1..22<br>mol_type = protein<br>organism = Saccharomyces cerevisiae | |
| SEQUENCE: 7<br>MFSLKALLPL ALLLVSANQV AA | | 22 |
| SEQ ID NO: 8<br>FEATURE<br>source | moltype = AA   length = 19<br>Location/Qualifiers<br>1..19<br>mol_type = protein<br>organism = Saccharomyces cerevisiae | |
| SEQUENCE: 8<br>MLLQAFLFLL AGFAAKISA | | 19 |
| SEQ ID NO: 9<br>FEATURE<br>source | moltype = AA   length = 20<br>Location/Qualifiers<br>1..20<br>mol_type = protein<br>organism = Pichia pastoris | |
| SEQUENCE: 9<br>MKLSTNLILA IAAASAVVSA | | 20 |
| SEQ ID NO: 10<br>FEATURE<br>source | moltype = AA   length = 97<br>Location/Qualifiers<br>1..97<br>mol_type = protein<br>organism = synthetic construct | |
| SEQUENCE: 10<br>MDSKGSSQKG SRLLLLLVVS NLLLCSAAPV NTTTEDETAQ IPAEAVIGYS DLEGDFDVAV<br>LPFSNSTNNG LLFINTTIAS IAAKEEGVSL EKREAEA | | 60<br>97 |
| SEQ ID NO: 11<br>FEATURE<br>source | moltype = AA   length = 88<br>Location/Qualifiers<br>1..88<br>mol_type = protein<br>organism = synthetic construct | |
| SEQUENCE: 11<br>MRSLLILVLC FLPLAALGAP VNTTTEDETA QIPAEAVIGY SDLEGDFDVA VLPFSNSTNN<br>GLLFINTTIA SIAAKEEGVS LEKREAEA | | 60<br>88 |
| SEQ ID NO: 12<br>FEATURE<br>source | moltype = AA   length = 90<br>Location/Qualifiers<br>1..90<br>mol_type = protein<br>organism = synthetic construct | |

```
SEQUENCE: 12
MKAFTSLLCG LGLSTTLAKA APVNTTTEDE TAQIPAEAVI GYSDLEGDFD VAVLPFSNST    60
NNGLLFINTT IASIAAKEEG VSLEKREAEA                                    90

SEQ ID NO: 13           moltype = AA   length = 116
FEATURE                 Location/Qualifiers
source                  1..116
                        mol_type = protein
                        organism = synthetic construct
SEQUENCE: 13
MDSEPLLPNP NDSRKPANWR RIIKYISLTL AWIGIFSYVY IYHGTAAPVN TTTEDETAQI    60
PAEAVIGYSD LEGDFDVAVL PFSNSTNNGL LFINTTIASI AAKEEGVSLE KREAEA       116

SEQ ID NO: 14           moltype = AA   length = 92
FEATURE                 Location/Qualifiers
source                  1..92
                        mol_type = protein
                        organism = synthetic construct
SEQUENCE: 14
MFSLKALLPL ALLLVSANQV AAAPVNTTTE DETAQIPAEA VIGYSDLEGD FDVAVLPFSN    60
STNNGLLFIN TTIASIAAKE EGVSLEKREA EA                                 92

SEQ ID NO: 15           moltype = AA   length = 89
FEATURE                 Location/Qualifiers
source                  1..89
                        mol_type = protein
                        organism = synthetic construct
SEQUENCE: 15
MLLQAFLFLL AGFAAKISAA PVNTTTEDET AQIPAEAVIG YSDLEGDFDV AVLPFSNSTN    60
NGLLFINTTI ASIAAKEEGV SLEKREAEA                                     89

SEQ ID NO: 16           moltype = AA   length = 114
FEATURE                 Location/Qualifiers
source                  1..114
                        mol_type = protein
                        organism = synthetic construct
SEQUENCE: 16
MAKADGSLLY YNPHNPPRRY YFYMAIFAVS VICVLYGPSQ QLSSAPVNTT TEDETAQIPA    60
EAVIGYSDLE GDFDVAVLPF SNSTNNGLLF INTTIASIAA KEEGVSLEKR EAEA         114

SEQ ID NO: 17           moltype = AA   length = 315
FEATURE                 Location/Qualifiers
source                  1..315
                        mol_type = protein
                        organism = synthetic construct
SEQUENCE: 17
GGYGPGAGQQ GPGSGGQQGP GGQGPYGSGQ QGPGGAGQQG PGGQGPYGPG AAAAAAAAAG    60
GYGPGAGQQG PGGAGQQGPG SQGPGGQGPY GPGAGQQGPG SQGPGSGGQQ GPGGQGPYGP   120
SAAAAAAAAA GGYGPGAGQR SQGPGGQGPY GPGAGQQGPG SQGPGSGGQQ GPGGQGPYGP   180
SAAAAAAAAG GYGPGAGQQG PGSQGPGSGG QQGPGGQGPY GPGAAAAAAA VGGYGPGAGQ   240
QGPGSQGPGS GGQQGPGGQG PYGPSAAAAA AAAGGYGPGA GQQGPGSQGP GSGGQQGPGG   300
QGPYGPSAAA AAAAA                                                   315

SEQ ID NO: 18           moltype = AA   length = 280
FEATURE                 Location/Qualifiers
source                  1..280
                        mol_type = protein
                        organism = synthetic construct
SEQUENCE: 18
GGQGGRGGFG GLGSQGAGGA GQGGAGAAAA AAAAGGDGGS GLGGYGAGRG HGVGLGGAGG    60
AGAASAAAAA GGQGGRGGFG GLGSQGAGGA GQGGAGAAAA AAAAGGDGGS GLGGYGAGRG   120
HGAGLGGAGG AGAASAAAAA GGQGGRGGFG GLGSQGSGGA GQGGSGAAAA AAAAGGDGGS   180
GLGGYGAGRG YGAGLGGAGG AGAASAAAAA GGQGGRGGFG GLGSQGAGGA GQGGSGAAAA   240
AAAAVADGGS GLGGYGAGRG YGAGLGGAGG AGAASAAAAT                        280

SEQ ID NO: 19           moltype = AA   length = 278
FEATURE                 Location/Qualifiers
source                  1..278
                        mol_type = protein
                        organism = synthetic construct
SEQUENCE: 19
GSAPQGAGGP APQGPSQQGP VSQGPYGPGA AAAAAAAGGY GPGAGQQGPG SQGPGSGGQQ    60
GPGSQGPGSG GQQGPGGQGP YGPSAAAAAA AAAGGYGPGA GQQGPGSQGP GSGGQQGPGG   120
QGPYGPGAAA AAAVGGYGP GAGQQGPGSQ GPGSGGQQGP GGQGPYGPSA AAAAAAAGGY   180
GPGAGQQGPG SQGPGSGGQQ GPGGQGPYGP SAAAAAAAAG GYGPGAGQQG PGSGGQQGPG   240
GQGPYGSGQQ GPGGAGGQQGP GGQGPYGPGA AAAAAAA                          278

SEQ ID NO: 20           moltype = AA   length = 261
FEATURE                 Location/Qualifiers
```

```
source                  1..261
                        mol_type = protein
                        organism = synthetic construct
SEQUENCE: 20
GGYGPGAGQQ GPGSGGQQGP GGQGPYGSGQ QGPGGAGQQG PGGQGPYGPG AAAAAAAAAG     60
GYGPGAGQQG PGGAGQQGPG SQGPGGQGPY GPGAGQQGPG SQGPGSGGQQ GPGGQGPYGP    120
SAAAAAAAAG GYGPGAGQQG PGSQGPGSGG QQGPGGQGPY GPSAAAAAAA AGGYGPGAGQ    180
QGPGSGGQQG PGGQGPYGSG QQGPGGAGQQ GPGGQGPYGG GYGPGAGQQG PGSQGPGSGG    240
QQGPGGQGPY GPSAAAAAAA A                                             261

SEQ ID NO: 21           moltype = AA   length = 258
FEATURE                 Location/Qualifiers
source                  1..258
                        mol_type = protein
                        organism = synthetic construct
SEQUENCE: 21
GPGARRQGPG SQGPGSGGQQ GPGGQGPYGS GQQGPGGAGQ QGPGGQGPYG PGAAAAAAAA     60
AGGYGPGAGQ QGPGGAGQQG PGSQGPGGQG PYGPGAGQQG PGSQGPGSGG QQGPGGQGPY    120
GPSAAAAAAA AAGGYGPGAG QQGPGSQGPG SGGQQGPGGQ GPYGPGAAAA AAAVGGYGPG    180
AGQQGPGSQG PGSGGQQGPG GQGPYGPSAA AAAAAGGYG PGAGQQGPGS QGPGSGGQQG    240
PGGQGPYGPS AAAAAAA                                                  258

SEQ ID NO: 22           moltype = AA   length = 257
FEATURE                 Location/Qualifiers
source                  1..257
                        mol_type = protein
                        organism = synthetic construct
SEQUENCE: 22
GPGARRQGPG SQGPGSGGQQ GPGGQGPYGS GQQGPGGAGQ QGPGGQGPYG PGAAAAAAAA     60
AGGYGPGAGQ QGPGGAGQQG PGSQGPGGQG PYGPGAGQQG PGSQGPGSGG QQGPGGQGPY    120
GPSAAAAAAA AGGYGPGAGQ QGPGSQGPGS GGQQGPGGQG PYGPGAAAAA AAVGGYGPGA    180
GQQGPGSQGP GSGGQQGPGG QGPYGPSAAA AAAAAGGYGP GAGQQGPGSQ GPGSGGQQGP    240
GGQGPYGPSA AAAAAAA                                                  257

SEQ ID NO: 23           moltype = AA   length = 255
FEATURE                 Location/Qualifiers
source                  1..255
                        mol_type = protein
                        organism = synthetic construct
SEQUENCE: 23
GGYGPGAGQQ GPGSGGQQGP GGQGPYGSGQ QGPGGAGQQG PGGQGPYGPG AAAAAAAAAG     60
GYGPGAGQQG PGGAGQQGPE GPGSQGPGSG QQGPGGQGPY GPGAAAAAAA AVGGYGPGAG    120
QQGPGSQGPG SGGQQGPGGQ GPYGPSAAAA AAAAGGYGPG AGQQGPGSQG PGSGGQQGPG    180
GQGPYGPSAA AAAAAGGYG PGAGQQGPGS GGQQGPGGQ PYGSGQQGPG GAGQQGPGGQ     240
GPYGPAAAA AAAAA                                                     255

SEQ ID NO: 24           moltype = AA   length = 252
FEATURE                 Location/Qualifiers
source                  1..252
                        mol_type = protein
                        organism = synthetic construct
SEQUENCE: 24
GVFSAGQGAT PWENSQLAES FISRFLRFIG QSGAFSPNQL DDMSSIGDTL KTAIEKMAQS     60
RKSSKSKLQA LNMAFASSMA EIAVAEQGGL SLEAKTNAIA SALSAAFLET TGYVNQQFVN    120
EIKTLIFMIA QASSNEISGS AAAAGGSSGG GGGSGQGGYG QGAYASASAA AAYGSAPQGT    180
GGPASQGPSQ QGPVSQPSYG PSATVAVTAV GGRPQGPSAP RQQGPSQQGP GQQGPGGRGP    240
YGPSAAAAAA AA                                                       252

SEQ ID NO: 25           moltype = AA   length = 252
FEATURE                 Location/Qualifiers
source                  1..252
                        mol_type = protein
                        organism = synthetic construct
SEQUENCE: 25
GAGAGAGAGA GAGAGAGSGA STSVSTSSSS GSGAGAGAGS GAGSGAGAGS GAGAGAGAGG     60
AGAGFGSGLG LGYGVGLSSA QAQAQAQAAA QAQAQAQAQA YAAAQAQAQA QAQAQAAAAA    120
AAAAAGAGA GAGAGAGAGA GAGSGASTSV STSSSSGSGA GAGSGAGS GAGAGSGAGA    180
GAGAGGAGAG FGSGLGLGYG VGLSSAQAQA QAQAAAQAQA QAQAQAYAAA QAQAQAQAQA    240
QAAAAAAAAA AA                                                       252

SEQ ID NO: 26           moltype = AA   length = 252
FEATURE                 Location/Qualifiers
source                  1..252
                        mol_type = protein
                        organism = synthetic construct
SEQUENCE: 26
GAGAGAGAGA GAGAGAGSGA STSVSTSSSS GSGAGAGAGS GAGSGAGAGS GAGAGAGAGG     60
AGAAFGSGLG LGYGVGLSSA QAQAQAQAAA QAQADAQAQA YAAAQAQAQA QAQAQAAAAA    120
AAAAAGAGA GAGAGSGAGA GAGSGASTSV STSSSSGSGA GAGSGAGS GAGAGSGAGA    180
```

-continued

```
GAGAGGAGAG FGSGLGLGYG VGLSSAQAQA QAQAAAQAQA DAQAQAYAAA QAQAQAQAQA    240
QAAAAAAAAA AA                                                       252

SEQ ID NO: 27           moltype = AA  length = 252
FEATURE                 Location/Qualifiers
source                  1..252
                        mol_type = protein
                        organism = synthetic construct
SEQUENCE: 27
GAGAGAGAGS GAGAGAGSGA STSVSTSSSS GSGAGAGAGS GAGSGAGAGS GAGAGAGAGG    60
AGAGFGSGLG LGYGVGLSSA QAQAQSAAAA RAQADAQAQA YAAAQAQAQA QAQAQAAAAA    120
AAAAAAGAGA GAGAGAGAGA GAGSGASTSV STSSSSASGA GAGAGSGAGS GAGAGSGAGA    180
GAGAGGAGAG FGSGLGLGYG VGLSSAQAQA QAQAAAQAQA QAQAQALAAA QAQAQAQAQA    240
QAAAATAAAA AA                                                       252

SEQ ID NO: 28           moltype = AA  length = 252
FEATURE                 Location/Qualifiers
source                  1..252
                        mol_type = protein
                        organism = synthetic construct
SEQUENCE: 28
GGYGPGAGQQ GPGGAGQQGP GSQGPGGQGP YGPGAGQQGP GSQGPGSGGQ QGPGGQGPYG    60
PSAAAAAAAA GGYGPGAGQQ GPGSQGPGSG GQQGPGSQGP GSGGQQGPGG QGPYGPSAAA    120
AAAAAAGGYG PGAGQQGPGS QGPGSGGQQG PGGQGPYGPG AAAAAAAVGG YGPGAGQQGP    180
GSQGPGSGGQ QGPGGQGPYG PSAAAAAAAA GGYGPGAGQQ GPGSQGPGSG GQQGPGGQGP    240
YGPSAAAAAA AA                                                       252

SEQ ID NO: 29           moltype = AA  length = 251
FEATURE                 Location/Qualifiers
source                  1..251
                        mol_type = protein
                        organism = synthetic construct
SEQUENCE: 29
GGYGPGAGQQ GPGGAGQQGP GSQGPGGQGP YGPGAGQQGP GSQGPGSGGQ QGPGGQGPYG    60
PSAAAAAAAA GGYGPGAGQQ GPGSQGPGSG GQQGPGSQGP GSGGQQGPGG QGPYGPSAAA    120
AAAAAGGYGP GAGQQGPGSQ GPGSGGQQGP GGQGPYGPGA AAAAAAVGGY GPGAGQQGPG    180
SQGPGSGGQQ GPGGQGPYGP SAAAAAAAAG GYGPGAGQQG PGSQGPGSGG QQGPGGQGPY    240
GPSAAAAAAA A                                                        251

SEQ ID NO: 30           moltype = AA  length = 248
FEATURE                 Location/Qualifiers
source                  1..248
                        mol_type = protein
                        organism = synthetic construct
SEQUENCE: 30
GHQGPHRKTP WETPEMAENF MNNVRENLEA SRIFPDELMK DMEAITNTMI AAVDGLEAQH    60
RSSYASLQAM NTAFASSMAQ LFATEQDYVD TEVIAGASAT AYQQITGYEN PHLASEVTRL    120
IQLFREEDDL ENEVEISFAD TDNAIARAAA GAAAGSAAAS SSADASATAE GASGDSGFLF    180
STGTFGRGGA GAGAGAAAAS AAAASAAAAG AEGDRGLFFS TGDFGRGGAG AGAGAAAASA    240
AAASAAAA                                                            248

SEQ ID NO: 31           moltype = AA  length = 245
FEATURE                 Location/Qualifiers
source                  1..245
                        mol_type = protein
                        organism = synthetic construct
SEQUENCE: 31
GGAQKHPSGE YSVATASAAA TSVTSGGAPV GKPGVPAPIF YPQGPLQQGP APGPSNVQPG    60
TSQQGPIGGV GESNTFSSSF ASALGGNRGF SGVISSASAT AVASAFQKGL APYGTAFALS    120
AASAAADAYN SIGSGASASA YAQAFARVLY PLLQQYGLSS SADASAFASA IASSFSTGVA    180
GQGPSVPYVG QQQPSIMVSA ASASAAASAA AVGGGPVVQG PYDGGQPQQP NIAASAAAAA    240
TATSS                                                               245

SEQ ID NO: 32           moltype = AA  length = 244
FEATURE                 Location/Qualifiers
source                  1..244
                        mol_type = protein
                        organism = synthetic construct
SEQUENCE: 32
GGQGGRGGFG GLGSQGEGGA GQGGAGAAAA AAAAGADGGF GLGGYGAGRG YGAGLGGAGG    60
AGAASAAAAA GGQGGRSGFG GLGSQGAGGA GQGGAGAAAA AAAAGADGGS GLGGYGAGRG    120
YGASLGGADG AGAASAAAAA GGQGGRGGFG GLGSQGAGGA GQGGAGAAAA AAAASGDGGS    180
GLGGYGAGRG YGAGLGGAGG AGAASAAAAA GGEGGRGGFG GLGSQGAGGA GQGGSLAAAA    240
AAAA                                                                244

SEQ ID NO: 33           moltype = AA  length = 244
FEATURE                 Location/Qualifiers
source                  1..244
                        mol_type = protein
```

```
                              -continued
                             organism = synthetic construct
SEQUENCE: 33
GPGGYGGPGQ PGPGQGQYGP GPGQQGPRQG GQQGPASAAA AAAAGPGGYG GPGQQGPRQG       60
QQQGPASAAA AAAAAAAGPR GYGGPGQQGP VQGGQQGPAS AAAAAAAAGV GGYGGPGQQG      120
PGQGQYGPGT GQQGQGPSGQ QGPAGAAAAA AGGAAGPGGY GGPGQQGPGQ GQYGPGTGQQ      180
GQGPSGQQGP AGAAAAAAAA AGPGGYGGPG QQGPGQGQYG PGAGQQGQGP GSQQGPASAA      240
AAAA                                                                   244

SEQ ID NO: 34                moltype = AA   length = 243
FEATURE                      Location/Qualifiers
source                       1..243
                             mol_type = protein
                             organism = synthetic construct
SEQUENCE: 34
GSGAGQGTGA GAGAAAAAAG AAGSGAGQGA GSGAGAAAAA AAASAAGAGQ GAGSGSGAGA       60
AAAAAAAAGA GQGAGSGSGA GAAAAAAAAA AAAQQQQQQQ AAAAAAAAAA AAAGSGQGAS      120
FGVTQQFGAP SGAASSAAAA AAAAAAAAAG SGAGQEAGTG AGAAAAAAAA GAAGSGAGQG      180
AGSGAGAAAA AAAASAAGA GQGAGSGSGA GAAAAAAAAA AAAQQQQQQQ AAAAAAAAAA      240
AAA                                                                    243

SEQ ID NO: 35                moltype = AA   length = 242
FEATURE                      Location/Qualifiers
source                       1..242
                             mol_type = protein
                             organism = synthetic construct
SEQUENCE: 35
GGAQKQPSGE SSVATASAAA TSVTSAGAPV GKPGVPAPIF YPQGPLQQGP APGPSYVQPA       60
TSQQGPIGGA GRSNAFSSSF ASALSGNRGF SEVISSASAT AVASAFQKGL APYGTAFALS      120
AASAAADAYN SIGSGANAFA YAQAFARVLY PLVQQYGLSS SAKASAFASA IASSFSSGAA      180
GQGQSIPYGG QQQPPMTISA ASASAGASAA AVKGGQVGQG PYGGQQQSTA ASASAAATTA      240
TA                                                                     242

SEQ ID NO: 36                moltype = AA   length = 241
FEATURE                      Location/Qualifiers
source                       1..241
                             mol_type = protein
                             organism = synthetic construct
SEQUENCE: 36
GADGGSGLGG YGAGRGYGAG LGGADGAGAA SAAAAAGGQG GRGGFGRLGS QGAGGAGQGG       60
AGAAAAVAAA GGDGGSGLGG YGAGRGYGAG LGGAGGAGAA SAAAAAGGQG GRGGFGGLGS      120
QGAGGAGQGG AGAAASGDGG SGLGGYGAGR GYGAGLGGAD GAGAASAASA AGGQGGRGGF      180
GGLGSQGAGG AGQGGAGAAA AATAGGDGGS GLGGYGAGR GYGAGLGGAG GAGAASAAAA      240
A                                                                      241

SEQ ID NO: 37                moltype = AA   length = 241
FEATURE                      Location/Qualifiers
source                       1..241
                             mol_type = protein
                             organism = synthetic construct
SEQUENCE: 37
GAGAGQGGRG GYGQGGFGGQ GSGAGAGASA AAGAGAGQGG RGGYGQGGFG GQGSGAGAGA       60
SAAAGAGAGQ GGRGGYGQGG FGGQGSGAGA GASAAAAAGA GQGGRGGYGQ GGLGGSGSGA      120
GAGAGAAAAA AAGAGGYGQG GLGGYGGAG AGQGGLGGYG SGAGAGASAA AAAGAGGAGQ      180
GGLGGYGQGA GAGQGGLGGY GSGAGAGAAA AAAAGAGGSG QGGLGGYGSG GGAGGASAAA      240
A                                                                      241

SEQ ID NO: 38                moltype = AA   length = 239
FEATURE                      Location/Qualifiers
source                       1..239
                             mol_type = protein
                             organism = synthetic construct
SEQUENCE: 38
GAYAYAYAIA NAFASILANT GLLSVSSAAS VASSVASAIA TSVSSSSAAA AASASAAAAA       60
SAGASAASSA SASSSASAAA GAGAGAGAGA SGASGAAGGS GGFGLSSGFG AGIGGLGGYP      120
SGALGGLGIP SGLLSSGLLS PAANQRIASL IPLILSAISP NGVNFGVIGS NIASLASQIS      180
QSGGGIAASQ AFTQALLELV AAFIQVLSSA QIGAVSSSSA SAGATANAFA QSLSSAFAG       239

SEQ ID NO: 39                moltype = AA   length = 239
FEATURE                      Location/Qualifiers
source                       1..239
                             mol_type = protein
                             organism = synthetic construct
SEQUENCE: 39
GAAQKQPSGE SSVATASAAA TSVTSGGAPV GKPGVPAPIF YPQGPLQQGP APGPSNVQPG       60
TSQQGPIGGV GGSNAFSSSF ASALSLNRGF TEVISSASAT AVASAFQKGL APYGTAFALS      120
AASAAADAYN SIGSGANAFA YAQAFARVLY PLVRQYGLSS SGKASAFASA IASSFSSGTS      180
GQGPSIGQQ PPVTISAASA SAGASAAAVG GGQVGQGPYG GQQQSTAASA SAAAATATS       239

SEQ ID NO: 40                moltype = AA   length = 239
```

```
FEATURE                 Location/Qualifiers
source                  1..239
                        mol_type = protein
                        organism = synthetic construct
SEQUENCE: 40
GAAQKQPSGE SSVATASAAA TSVTSGGAPV GKPGVPAPIF YPQGPLQQGP APGPSNVQPG    60
TSQQGPIGGV GGSNAFSSSF ASALSLNRGF TEVISSASAT AVASAFQKGL APYGTAFALS   120
AASAAADAYN SIGSGANAFA YAQAFARVLY PLVRQYGLSS SGKASAFASA IASSFSSGTS   180
GQGPSIGQQQ PPVTISAASA SAGASAAAVG GGVGQGPYG GQQQSTAASA SAAAATATS    239

SEQ ID NO: 41           moltype = AA   length = 239
FEATURE                 Location/Qualifiers
source                  1..239
                        mol_type = protein
                        organism = synthetic construct
SEQUENCE: 41
GAAQKQPSGE SSVATASAAA TSVTSGGAPV GKPGVPAPIF YPQGPLQQGP APGPSNVQPG    60
TSQQGPIGGV GGSNAFSSSF ASALSLNRGF TEVISSASAT AVASAFQKGL APYGTAFALS   120
AASAAADAYN SIGSGANAFA YAQAFARVLY PLVQQYGLSS SAKASAFASA IASSFSSGTS   180
GQGPSIGQQQ PPVTISAASA SAGASAAAVG GGVGQGPYG GQQQSTAASA SAAAATATS    239

SEQ ID NO: 42           moltype = AA   length = 239
FEATURE                 Location/Qualifiers
source                  1..239
                        mol_type = protein
                        organism = synthetic construct
SEQUENCE: 42
GGAQKQPSGE SSVATASAAA TSVTSAGAPV GKPGVPAPIF YPQGPLQQGP APGPSNVQPG    60
TSQQGPIGGV GGSNAFSSSF ASALSLNRGF TEVISSASAT AVASAFQKGL APYGTAFALS   120
AASAAADAYN SIGSGANAFA YAQAFARVLY PLVQQYGLSS SAKASAFASA IASSFSSGTS   180
GQGPSNGQQQ PPVTISAASA SAGASAAAVG GGVSQGPYG GQQQSTAASA SAAAATATS    239

SEQ ID NO: 43           moltype = AA   length = 239
FEATURE                 Location/Qualifiers
source                  1..239
                        mol_type = protein
                        organism = synthetic construct
SEQUENCE: 43
GGAQKQPSGE SSVATASAAA TSVTSAGAPG GKPGVPAPIF YPQGPLQQGP APGPSNVQPG    60
TSQQGPIGGV GGSNAFSSSF ASALSLNRGF TEVISSASAT AVASAFQKGL APYGTAFALS   120
AASAAADAYN SIGSGANAFA YAQAFARVLY PLVQQYGLSS SAKASAFASA IASSFSSGTS   180
GQGPSIGQQQ PPVTISAASA SAGASAAAVG GGVGQGPYG GQQQSTAASA SAAAATATS    239

SEQ ID NO: 44           moltype = AA   length = 236
FEATURE                 Location/Qualifiers
source                  1..236
                        mol_type = protein
                        organism = synthetic construct
SEQUENCE: 44
GPGGYGGPGQ QGPGQGQQQG PASAAAAAAA AGPGGYGGPG QQGPGQGQQQ GPASAAAAAA    60
AAAGPGGYGG PGQQRPGQAQ YGRGTGQQGQ GPGAQQGPAS AAAAAAAGAG LYGGPGQGYQ   120
GQGQQQGPAS AAAAAAAAAA AGPGGYGGPG QQGPGQAQQQ GPASAAAAAA AGPGGYSGPG   180
QQGPGQAQQQ GPASAAAAAA AAAGPGGYGG PGQQGPGQGQ QQGPASAAAA AAATAA       236

SEQ ID NO: 45           moltype = AA   length = 234
FEATURE                 Location/Qualifiers
source                  1..234
                        mol_type = protein
                        organism = synthetic construct
SEQUENCE: 45
GAGGDGGLFL SSGDFGRGGA GAGAGAAAAS AAAASSAAAG ARGGSGFGVG TGGFGRGGAG    60
DGASAAAASA AAASAAAAGA GGDSGLFLSS GDFGRGGAGA GAGAAAASAA AASAAAAGTG   120
GVGGLFLSSG DFGRGGAGAG AGAAAASAAA ASSAAAGARG GSGFGVGTGG FGRGGPGAGT   180
GAAAASAAAA SAAAAGAGGD SGLFLSSEDF GRGGAGAGTG AAAASAAAAS AAAA         234

SEQ ID NO: 46           moltype = AA   length = 233
FEATURE                 Location/Qualifiers
source                  1..233
                        mol_type = protein
                        organism = synthetic construct
SEQUENCE: 46
GAGRGYGGGY GGGAAAGAGA GAGAGRGYGG GYGGGAGSGA GSGAGAGGGS GYGRGAGAGA    60
GAGAAAAAGA GAGGAGGYGG GAGAGASA AAGAGAGGGY AGGYGGGYGG GAGAGAGA       120
AAAAGAGAGA GAGRGYGGGF GGGAGSGAGA GAGAGGGSGY GRGAGGYGGG YGGGAGTGAG   180
AAAATGAGAG AGAGRGYGGG YGGGAGAGAG AGAGAGGGSG YGRGAGAGAS VAA           233

SEQ ID NO: 47           moltype = AA   length = 231
FEATURE                 Location/Qualifiers
source                  1..231
```

```
                        mol_type = protein
                        organism = synthetic construct
SEQUENCE: 47
GALGQGASVW  SSPQMAENFM  NGFSMALSQA  GAFSGQEMKD  FDDVRDIMNS  AMDKMIRSGK   60
SGRGAMRAMN  AAFGSAIAEI  VAANGGKEYQ  IGAVLDAVTN  TLLQLTGNAD  NGFLNEISRL  120
ITLFSSVEAN  DVSASAGADA  SGSSGPVGGY  SSGAGAAVGQ  GTAQAVGYGG  GAQGVASSAA  180
AGATNYAQGV  STGSTQNVAT  STVTTTTNVA  GSTATGYNTG  YGIGAAAGAA  A           231

SEQ ID NO: 48           moltype = AA  length = 231
FEATURE                 Location/Qualifiers
source                  1..231
                        mol_type = protein
                        organism = synthetic construct
SEQUENCE: 48
GGQGGQGGYD  GLGSQGAGQG  GYGQGGAAAA  AAAASGAGSA  QRGGLGAGGA  GQGYGAGSGG   60
QGGAGQGGAA  AATAAAAGGQ  GGQGGYGGLG  SQGSGQGGYG  QGGAAAAAAA  ASGDGGAGQE  120
GLGAGGAGQG  YGAGLGGQGG  AGQGGAAAAA  AAAAGGQGGQ  GGYGGLGSQG  AGQGGYGQGG  180
AAAAAAAASG  AGGAGQGGLG  AAGAGQGYGA  GSGGQGGAGQ  GGAAAAAAAA  A           231

SEQ ID NO: 49           moltype = AA  length = 231
FEATURE                 Location/Qualifiers
source                  1..231
                        mol_type = protein
                        organism = synthetic construct
SEQUENCE: 49
GGQGGQGGYG  GLGSQGAGQG  GYGQGGVAAA  AAAASGAGGA  GRGGLGAGGA  GQEYGAVSGG   60
QGGAGQGGEA  AAAAAAAGGQ  GGQGGYGGLG  SQGAGQGGYG  QGGAAAAAAA  ASGAGGARRG  120
GLGAGGAGQG  YGAGLGGQGG  AGQGSASAAA  AAAAGGQGGQ  GGYGGLGSQG  SGQGGYGQGG  180
AAAAAAAASG  AGGAGRGSLG  AGGAGQGYGA  GLGGQGGAGQ  GGAAAASAA   A           231

SEQ ID NO: 50           moltype = AA  length = 229
FEATURE                 Location/Qualifiers
source                  1..229
                        mol_type = protein
                        organism = synthetic construct
SEQUENCE: 50
GPGGYGGPGQ  QGPGQGQYGP  GTGQQGQGPG  GQQGPVGAAA  AAAAAVSSGG  YGSQGAGQGG   60
QQGSGQRGPA  AAGPGGYSGP  GQQGPGQGGQ  QGPASAAAAA  AAAAGPGGYG  GSGQQGPGQG  120
RGTGQQGQGP  GGQQGPASAA  AAAAAGPGGY  GGPGQQGPGQ  GQYGPGTGQQ  GQGPASAAAA  180
AAAGPGYGG   PGQQGPGQGQ  YGPGTGQQGQ  GPGGQQGPGG  ASAAAAAAA               229

SEQ ID NO: 51           moltype = AA  length = 228
FEATURE                 Location/Qualifiers
source                  1..228
                        mol_type = protein
                        organism = synthetic construct
SEQUENCE: 51
GGYGPGAGQQ  GPGSGGQQGP  GGQGPYGSGQ  QGPGGAGQGG  PGGQGPYGPG  AAAAAAAAAG   60
GYGPGAGQQG  PGGAGQQGPG  SQGPGGQGPY  GPGAGQQGPG  SQGPGSGGQQ  GPGGQGPYGP  120
SAAAAAAAA   GGYGPGAGQR  SQGPGGQGPY  GPGAGQQGPG  SQGPGSGGQQ  GPGGQGPYGP  180
SAAAAAAAAG  PGAGRQGPGS  QGPGSGGQQG  PGGQGPYGPS  AAAAAAA                 228

SEQ ID NO: 52           moltype = AA  length = 225
FEATURE                 Location/Qualifiers
source                  1..225
                        mol_type = protein
                        organism = synthetic construct
SEQUENCE: 52
GQGGQGGQGG  LGQGGYGQGA  GSSAAAAAAA  AAAAAAAGRG  QGGYGQGSGG  NAAAAAAAAA   60
AAASGQGSQG  GQGGQGQGGY  GQGAGSSAAA  AAAAAAAAAA  SGRGQGGYGQ  GAGGNAAAAA  120
AAAAAAAAAG  QGGQGGYGGL  GQGGYGQGAG  SSAAAAAAAA  AAAAGQGGQ   GGGYGQGSG   180
GSAAAAAAAA  AAAAAAAGRG  QGGYGQGSGG  NAAAAAAAAA  AAAAA                   225

SEQ ID NO: 53           moltype = AA  length = 225
FEATURE                 Location/Qualifiers
source                  1..225
                        mol_type = protein
                        organism = synthetic construct
SEQUENCE: 53
GRGPGGYGPG  QQGPGGPGAA  AAAAGPGGYG  PGGYGPGQQG  PGGPAAAAA   AAGRGPGGYG   60
PGQQGPGQQG  PGGSGAAAAA  AGRGPGGYGP  GQQGPGGPGA  AAAAAGPGGY  GPGQQGPGAA  120
AAAAAGRGP   GGYGPGQQGP  GGPGAAAAAA  AGRGPGGYGP  GQQGPGQQGP  GGSGAAAAAA  180
GRGPGGYGPG  QQGPGGPGAA  AAAAGPGGYG  PGQQGPGAAA  AAAAA                   225

SEQ ID NO: 54           moltype = AA  length = 225
FEATURE                 Location/Qualifiers
source                  1..225
                        mol_type = protein
                        organism = synthetic construct
```

```
SEQUENCE: 54
GRGPGGYGPG QQGPGGSGAA AAAAGRGPGG YGPGQQGPGG PGAAAAAAGP GGYGPGQQGT    60
GAAAAAAAGS GAGGYGPGQQ GPGGPGAAAA AAGPGGYGPG QQGPGAAAAA AAGSGPGGYG   120
PGQQGPGGSS AAAAAAGPGR YGPGQQGPGA AAAASAGRGP GGYGPGQQGP GGPGAAAAAA   180
GPGGYGPGQQ GPGAAAAAAA GSGPGGYGPG QQGPGGPGAA AAAAA                   225

SEQ ID NO: 55           moltype = AA  length = 219
FEATURE                 Location/Qualifiers
source                  1..219
                        mol_type = protein
                        organism = synthetic construct
SEQUENCE: 55
GAAATAGAGA SVAGGYGGGA GAAAGAGAGG YGGGYGAVAG SGAGAAAAAS SGAGGAAGYG    60
RGYGAGSGAG AGAGTVAAYG GAGGVATSSS SATASGSRIV TSGGYGYGTS AAAGAGVAAG   120
SYAGAVNRLS SAEAASRVSS NIAAIASGGA SALPSVISNI YSGVVASGVS SNEALIQALL   180
ELLSALVHVL SSASIGNVSS VGVDSTLNVV QDSVGQYVG                           219

SEQ ID NO: 56           moltype = AA  length = 219
FEATURE                 Location/Qualifiers
source                  1..219
                        mol_type = protein
                        organism = synthetic construct
SEQUENCE: 56
GGQGGFSGQG QGGFGPGAGS SAAAAAAAAA AARQGGQGQG GFGQGAGGNA AAAAAAAAA     60
AAAQGGQGQG FSGRGQGGFG PGAGSSAAAA AAGQGGQGQG GFGQGAGGNA AAAAAAAAA    120
AAAAGQGGQG RGGFGQGAGG NAAAAAAAAA AAAAAQQGG QGGFGGRGQG GFGPGAGSSA    180
AAAAAGQGGQ GRGGFGQGAG GNAAAASAAA AASAAAAGQ                           219

SEQ ID NO: 57           moltype = AA  length = 218
FEATURE                 Location/Qualifiers
source                  1..218
                        mol_type = protein
                        organism = synthetic construct
SEQUENCE: 57
GGYGPGAGQQ GPGGAGQQGP GSQGPGGAGQ QGPGGQGPYG PGAAAAAAAV GGYGPGAGQQ    60
GPGSQGPGSG GQQGPGGQGP YGPSAAAAAA AAGGYGPGAG QQGPGSQGPG SGGQQGPGGL   120
GPYGPSAAAA AAAAGGYGPG AGQQGPGSQG PGSGGQQRPG GLGPYGPSAA AAAAAAGGYG   180
PGAGQQGPGS QGPGSGGQQR PGGLGPYGPS AAAAAAAA                            218

SEQ ID NO: 58           moltype = AA  length = 217
FEATURE                 Location/Qualifiers
source                  1..217
                        mol_type = protein
                        organism = synthetic construct
SEQUENCE: 58
GAGAGGGYGG GYSAGGGAGA GSGAAAGAGA GRGGAGGYSA GAGTGAGAAA GAGTAGGYSG    60
GYGAGASSSA GSSFISSSSM SSSQATGYSS SSGYGGGAAS AAAGAGAAAG GAGTAGGYSG   120
GAGAAAASGA TGRVANSLGA MASGGINALP GVFSNIFSQV SAASGGASGG AVLVQALTEV   180
IALLLHILSS ASIGNVSSQG LEGSMAIAQQ AIGAYAG                             217

SEQ ID NO: 59           moltype = AA  length = 216
FEATURE                 Location/Qualifiers
source                  1..216
                        mol_type = protein
                        organism = synthetic construct
SEQUENCE: 59
GAGAGGAGGY AQGYGAGAGA GAGAGTGAGG AGGYGQGYGA GSGAGAGGAG GYGAGAGAGA    60
GAGDASGYGQ GYGDGAGAGA GAAAAGAAA GARGAGGYGG GAGAGAGAGA GAAGGYGQGY   120
GAGAGEGAGA GAGAGAVAGA GAAAAGAGA GAGGAEGYGA GAGAGGAGGY GQSYGDGAAA   180
AAGSGAGAGG SGGYGAGAGA GSGAGAAGGY GGGAGA                              216

SEQ ID NO: 60           moltype = AA  length = 216
FEATURE                 Location/Qualifiers
source                  1..216
                        mol_type = protein
                        organism = synthetic construct
SEQUENCE: 60
GPGGYGPGQQ GPGGYGPGQQ GPGRYGPGQQ GPSGPGSAAA AAAGSGQQGP GGYGPRQQGP    60
GGYGQGQQGP SGPGSAAAAS AAASAESGQQ GPGGYGPGQQ GPGGYGPGQQ GPGGYGPGQQ   120
GPSGPGSAAA AAAASGPGQ QGPGGYGPGQ QGPGGYGPGQ QGPSGPGSAA AAAAASGPG    180
QQGPGGYGPG QQGPGGYGPG QQGLSGPGSA AAAAA                                216

SEQ ID NO: 61           moltype = AA  length = 216
FEATURE                 Location/Qualifiers
source                  1..216
                        mol_type = protein
                        organism = synthetic construct
SEQUENCE: 61
GRGPGGYGQQ QQGPGGPGAA AAAAGPGGYG PGQQGPGAAA AAAAGSGPGG YGPGQQGPGR    60
```

-continued

```
SGAAAAAAAA GRGPGGYGPG QQGPGGPGAA AAAAGPGGYG PGQQGPGAAA AASAGRGPGG  120
YGPGQQGPGG SGAAAAAAGR GPGGYGPGQQ GPGGPGAAAA AAAGRGPGGY GPGQQGPGQQ  180
GPGGSGAAAA AAGRGPGGYG PGQQGPGGPG AAAAAA                           216

SEQ ID NO: 62           moltype = AA  length = 214
FEATURE                 Location/Qualifiers
source                  1..214
                        mol_type = protein
                        organism = synthetic construct
SEQUENCE: 62
GVGAGGEGGY DQGYGAGAGA GSGGGAGGAG GYGGGAGAGS GGGAGGAGGY GGGAGAGAGA  60
GAGGAGGYGG GAGAGTGARA GAGGVGGYGQ SYGAGASAAA GAGVGAGGAG AGGAGGYGQG  120
YGAGAGIGAG DAGGYGGGAG AGASAGAGGY GGGAGAGAGG VGGYGKGYGA GSGAGAAAAA  180
GAGAGSAGGY GRGDGAGAGG ASGYGQGYGA GAAA                             214

SEQ ID NO: 63           moltype = AA  length = 212
FEATURE                 Location/Qualifiers
source                  1..212
                        mol_type = protein
                        organism = synthetic construct
SEQUENCE: 63
GYGAGAGRGY GAGAGAGAGA VAASGAGAGA GYGAGAGAGA GAGYGAGAGR GYGAGAGAGA  60
GSGAASGAGA GAGYGAGAGA GAGYGAGAGS GYGTGAGAGA GAAAAGGAGA GAGYGAGAGR  120
GYGAGAGAGA ASGAGAGAGA GAASGAGAGS GYGAGAAAAG GAGAGAGGGY GAGAGRGYGA  180
GAGAGAGAGS GSGSAAGYGQ GYGSGSGAGA AA                               212

SEQ ID NO: 64           moltype = AA  length = 198
FEATURE                 Location/Qualifiers
source                  1..198
                        mol_type = protein
                        organism = synthetic construct
SEQUENCE: 64
GQGTDSSASS VSTSTSVSSS ATGPDTGYPV GYYGAGQAEA AASAAAAAAA SAAEAATIAG  60
LGYGRQGQGT DSSASSVSTS TSVSSSATGP DMGYPVGNYG AGQAEAAASA AAAAAASAAE  120
AATIASLGYG RQGQGTDSSA SSVSTSTSVS SSATGPGSRY PVRDYGADQA EAAASAAAAA  180
AAAASAAEEI ASLGYGRQ                                               198

SEQ ID NO: 65           moltype = AA  length = 198
FEATURE                 Location/Qualifiers
source                  1..198
                        mol_type = protein
                        organism = synthetic construct
SEQUENCE: 65
GQGTDSVASS ASSSASASSS ATGPDTGYPV GYYGAGQAEA AASAAAAAAA SAAEAATIAG  60
LGYGRQGQGT DSSASSVSTS TSVSSSATGP GSRYPVRDYG ADQAEAAASA TAAAAAAASA  120
AEEIASLGYG RQGQGTDSVA SSASSSASAS SSATGPDTGY PVGYYGAGQA EAAASAAAAA  180
AASAAEAATI AGLGYGRQ                                               198

SEQ ID NO: 66           moltype = AA  length = 195
FEATURE                 Location/Qualifiers
source                  1..195
                        mol_type = protein
                        organism = synthetic construct
SEQUENCE: 66
GQGGQGGYGG LGQGGYGQGA GSSAAAAAAA AAAAAGGQG GQGQGRYGQG AGSSAAAAAA  60
AAAAAAAAGR GQGGYGQGSG GNAAAAAAAA AAAASGQGSQ GGGQGQGQGG YGQGAGSSAA  120
AAAAAAAAAA ASGRGQGGYG QGAGGNAAAA AAAAAAAAAA GQGGQGGYGG LGQGGYGQGA  180
GSSAAAAAAA AAAAA                                                  195

SEQ ID NO: 67           moltype = AA  length = 193
FEATURE                 Location/Qualifiers
source                  1..193
                        mol_type = protein
                        organism = synthetic construct
SEQUENCE: 67
GGLGQGGLG GLGSQGAGLG GYGQGGAGQG GAAAAAAAAG GLGQGGRGG LGSQGAGQGG  60
YGQGGAGQGG AAAAAAAAGG LGGQGGLGAL GSQGAGQGGA GQGGYGQGGA AAAAGGLGGQ  120
QGGLGGLGSQ GAGQGGYGQG GAGQGGAAAA AAAAGGLGGQ GGLGGLGSQG AGPGGYGQGG  180
AGQGGAAAAA AAA                                                    193

SEQ ID NO: 68           moltype = AA  length = 192
FEATURE                 Location/Qualifiers
source                  1..192
                        mol_type = protein
                        organism = synthetic construct
SEQUENCE: 68
GGGQGRGGFGQ GAGGNAAAAA AAAAAAAAAQ QVGQFGFGGR GQGGFGPFAG SSAAAAAAAS  60
AAAGQGGQGQ GGFGQGAGGN AAAAAAAAAA AARQGGQGQG GFSQGAGGNA AAAAAAAAAA  120
AAAQQGGQG GFGGRGQGGF GPGAGSSAAA AAAATAAAGQ GGQGRGGFGQ GAGSNAAAAA  180
```

```
SEQ ID NO: 69          moltype = AA  length = 190
FEATURE                Location/Qualifiers
source                 1..190
                       mol_type = protein
                       organism = synthetic construct
SEQUENCE: 69
GGQGGQGGYG GLGSQGAGQG GYGAGQGAAA AAAAAGGAGG AGRGGLGAGG AGQGYGAGLG      60
GQGGAGQAAA AAAAGGAGGA RQGGLGAGGA GQGYGAGLGG QGGAGQGGAA AAAAAAGGQG     120
GQGGYGGLGS QGAGQGGYGA GQGGAAAAAA AAGGQGGQGG YGGLGSQGAG QGGYGGRQGG     180
AGAAAAAAAA                                                            190

SEQ ID NO: 70          moltype = AA  length = 188
FEATURE                Location/Qualifiers
source                 1..188
                       mol_type = protein
                       organism = synthetic construct
SEQUENCE: 70
GGAGQRGYGG LGNQGAGRGG LGGQGAGAAA AAAAGGAGQG GYGGLGNQGA GRGGQGAAAA      60
AGGAGQGGYG GLGSQGAGRG GQGAGAAAAA AVGAGQEGIR GQGAGQGGYG GLGSQGSGRG     120
GLGGQGAGAA AAAAGGAGQG GLGGQGAGQG AGAAAAAAGG VRQGGYGGLG SQGAGRGGQG     180
AGAAAAAA                                                              188

SEQ ID NO: 71          moltype = AA  length = 186
FEATURE                Location/Qualifiers
source                 1..186
                       mol_type = protein
                       organism = synthetic construct
SEQUENCE: 71
GGAGQGGLGG QGAGQGAGAS AAAAGGAGQG GYGGLGSQGA GRGGEGAGAA AAAAGGAGQG      60
GYGGLGGQGA GQGGYGGLGS QGAGRGGLGG QGAGAAAAGG AGQGGLGGQG AGQGAGAAAA     120
AAGGAGQGGY GGLGSQGAGR GGLGGQGAGA VAAAAAGGAG QGGYGGLGSQ GAGRGGQGAG     180
AAAAAA                                                                186

SEQ ID NO: 72          moltype = AA  length = 182
FEATURE                Location/Qualifiers
source                 1..182
                       mol_type = protein
                       organism = synthetic construct
SEQUENCE: 72
GAGAGAGAGS GAGAAGGYGG GAGAGVGAGG AGGYDQGYGA GAGAGSGAGA GGAGGYGGGA      60
GAGADAGAGG AGGYGGGAGA GAGARAGAGG VGGYGQSYGA GAGAGAGVGA GGAGAGGADG     120
YGQGYGAGAG TGAGDAGGYG GGAGAGASAG AGGYGGGAGA GGVGVYKGY GSGSGAGAAA     180
AA                                                                    182

SEQ ID NO: 73          moltype = AA  length = 182
FEATURE                Location/Qualifiers
source                 1..182
                       mol_type = protein
                       organism = synthetic construct
SEQUENCE: 73
GGAGGYGVGQ GYGAGAGAGA AAGAGAGGAG GYGAGQGYGA GAGVGAAAAA GAGAGVGGAG      60
GYGRGAGAGA GAGAGAAAGA GAGAAAGAGA GGAGGYGAGQ GYGAGAGVGA AAAAGAGAGV     120
GGAGGYGRGA GAGAGAGAGG AGGYGRGAGA GAGAGAGAGG AGGYGAGQGY GAGAGAGAAA     180
AA                                                                    182

SEQ ID NO: 74          moltype = AA  length = 182
FEATURE                Location/Qualifiers
source                 1..182
                       mol_type = protein
                       organism = synthetic construct
SEQUENCE: 74
GEAFSSASSAS SAVVFESAGP GEEAGSSGDG ASAAASAAAA AGAGSGRRGP GGARSRGGAG      60
AGAGAGSGVG GYGSGSGAGA GAGAGAGAGG EGGFGEGQGY GAGAGAGFGS GAGAGAGAGS     120
GAGAGEGVGS GAGAGAGAGF GVGAGAGAGA GAGFGSGAGA GSGAGAGYGA GRAGGRGRGG     180
RG                                                                    182

SEQ ID NO: 75          moltype = AA  length = 182
FEATURE                Location/Qualifiers
source                 1..182
                       mol_type = protein
                       organism = synthetic construct
SEQUENCE: 75
GEAFSSASSAS SAVVFESAGP GEEAGSSGGG ASAAASAAAA AGAGSGRRGP GGARSRGGAG      60
AGAGAGSGVG GYGSGSGAGA GAGAGAGAGG EGGFGEGQGY GAGAGAGFGS GAGAGAGAGS     120
GAGAGEGVGS GAGAGAGAGF GVGAGAGAGA GAGFGSGAGA GSGAGAGYGA GRAGGRGRGG     180
RG                                                                    182
```

| SEQ ID NO: 76 | moltype = AA length = 182 |
| --- | --- |
| FEATURE | Location/Qualifiers |
| source | 1..182 |
| | mol_type = protein |
| | organism = synthetic construct |

SEQUENCE: 76
```
GNGLGQALLA NGVLNSGNYL QLANSLAYSF GSSLSQYSSS AAGASAAGAA SGAAGAGAGA   60
ASSGGSSGSA SSSTTTTTTT STSAAAAAAA AAAAASAAAS TSASASASAS ASASAFSQTF  120
VQTVLQSAAF GSYFGGNLSL QSAQAAASAA AQAAAQQIGL GSYGYALANA VASAFASAGA  180
NA                                                                182
```

| SEQ ID NO: 77 | moltype = AA length = 182 |
| --- | --- |
| FEATURE | Location/Qualifiers |
| source | 1..182 |
| | mol_type = protein |
| | organism = synthetic construct |

SEQUENCE: 77
```
GNGLGQALLA NGVLNSGNYL QLANSLAYSF GSSLSQYSSS AAGASAAGAA SGAAGAGAGA   60
ASSGGSSGSA SSSTTTTTTT STSAAAAAAA AAAAASAAAS TSASASASAS ASASAFSQTF  120
VQTVLQSAAF GSYFGGNLSL QSAQAAASAA AQAAAQQIGL GSYGYALANA VASAFASAGA  180
NA                                                                182
```

| SEQ ID NO: 78 | moltype = AA length = 182 |
| --- | --- |
| FEATURE | Location/Qualifiers |
| source | 1..182 |
| | mol_type = protein |
| | organism = synthetic construct |

SEQUENCE: 78
```
GNGLGQALLA NGVLNSGNYL QLANSLAYSF GSSLSQYSSS AAGASAAGAA SGAAGAGAGA   60
ASSGGSSGSA SSSTTTTTTT STSAAAAAAA AAAAASAAAS TSASASASAS ASASAFSQTF  120
VQTVLQSAAF GSYFGGNLSL QSAQAAASAA AQAAAQQIGL GSYGYALANA VASAFASAGA  180
NA                                                                182
```

| SEQ ID NO: 79 | moltype = AA length = 180 |
| --- | --- |
| FEATURE | Location/Qualifiers |
| source | 1..180 |
| | mol_type = protein |
| | organism = synthetic construct |

SEQUENCE: 79
```
GASGAGQGQG YGQQGQGGSS AAAAAAAAAA AAAAAQGQGQ GYGQQGQGSA AAAAAAAAAG   60
ASGAGQGQGY GQQGQGSAAA AAAAAAGAS GAGQGQGYGQ QGQGGSSAAA AAAAAAAAA   120
AAAQGQGYGQ QGQGSAAAAA AAAAAGASGAG QGQGYGQQGQ GGSSAAAAAA AAAAAAAAA  180
```

| SEQ ID NO: 80 | moltype = AA length = 179 |
| --- | --- |
| FEATURE | Location/Qualifiers |
| source | 1..179 |
| | mol_type = protein |
| | organism = synthetic construct |

SEQUENCE: 80
```
GRGQGGYGQG SGGNAAAAAA AGQGGFGGQE GNGQGAGSAA AAAAAAAAAA GGSGQGRYGG   60
RQGGGYGQGA GAAASAAAAA AAAAAGQGGF GGQEGNGQGA GSAAAAAAAA AAAAGGSGQG  120
GYGGRGQGGY GQGAGAAAAA AAAAAAAAG QGGQGGFGSQ GGNGQGAGSA AAAAAAAA   179
```

| SEQ ID NO: 81 | moltype = AA length = 178 |
| --- | --- |
| FEATURE | Location/Qualifiers |
| source | 1..178 |
| | mol_type = protein |
| | organism = synthetic construct |

SEQUENCE: 81
```
GQNTPWSSTE LADAFINAFM NEAGRTGAFT ADQLDDMSTI GDTIKTAMDK MARSNKSSKG   60
KLQALNMAFA SSMAEIAAVE QGGLSVDAKT NAIADSLNSA FYQTTGAANP QFVNEIRSLI  120
NMFAQSSANE VSYGGGYGGQ SAGAAASAAA AGGGQGGYG NLGGQGAGAA AAAAASAA    178
```

| SEQ ID NO: 82 | moltype = AA length = 178 |
| --- | --- |
| FEATURE | Location/Qualifiers |
| source | 1..178 |
| | mol_type = protein |
| | organism = synthetic construct |

SEQUENCE: 82
```
GQNTPWSSTE LADAFINAFL NEAGRTGAFT ADQLDDMSTI GDTLKTAMDK MARSNKSSQS   60
KLQALNMAFA SSMAEIAAVE QGGLSVAEKT NAIADSLNSA FYQTTGAVNV QFVNEIRSLI  120
SMFAQASANE VSYGGGYGGG QGGQSAGAAA AASAGAGQG GYGGLGGQGA GSAAAAAA    178
```

| SEQ ID NO: 83 | moltype = AA length = 177 |
| --- | --- |
| FEATURE | Location/Qualifiers |
| source | 1..177 |
| | mol_type = protein |
| | organism = synthetic construct |

SEQUENCE: 83

```
GGQGGQGGYG GLGSQGAGQG GYGQGGAAAA AASAGGQGGQ GGYGGLGSQG AGQGGYGGGA    60
FSGQQGGAAS VATASAAASR LSSPGAASRV SSAVTSLVSS GGPTNSAALS NTISNVVSQI   120
SSSNPGLSGC DVLVQALLEI VSALVHILGS ANIGQVNSSG VGRSASIVGQ SINQAFS     177

SEQ ID NO: 84            moltype = AA   length = 177
FEATURE                  Location/Qualifiers
source                   1..177
                         mol_type = protein
                         organism = synthetic construct
SEQUENCE: 84
GGAGQGGYGG LGGQGAGAAA AAAGGAGQGG YGGQGAGQGA AAAAASGAGQ GGYEGPGAGQ    60
GAGAAAAAAG GAGQGGYGGL GGQGAGQGAG AAAAAAGGAG QGGYGGLGGQ GAGQGAGAAA   120
AAAGGAGQGG YGGQGAGQGA AAAAGGAGQ GGYGGLGSQG GGYGRQGAGA AAAAAA       177

SEQ ID NO: 85            moltype = AA   length = 175
FEATURE                  Location/Qualifiers
source                   1..175
                         mol_type = protein
                         organism = synthetic construct
SEQUENCE: 85
GASSAAAAAA ATATSGGAPG GYGGYGPGIG GAFVPASTTG TGSGSGSGAG AAGSGGLGGL    60
GSSGGSGGLG GGNGGSGASA AASAAAASSS PGSGGYGPGQ GVGSGSGSGA AGGSGTGSGA   120
GGPGSGGYGG PQFFASAYGG QGLLGTSGYG NGQGGASGTG SGGVGGSGSG AGSNS       175

SEQ ID NO: 86            moltype = AA   length = 174
FEATURE                  Location/Qualifiers
source                   1..174
                         mol_type = protein
                         organism = synthetic construct
SEQUENCE: 86
GQPIWTNPNA AMTMTNNLVQ CASRSGVLTA DQMDDMGMMA DSVNSQMQKM GPNPPQHRLR    60
AMNTAMAAEV AEVVATSPPQ SYSAVLNTIG ACLRESMMQA TGSVDNAFTN EVMQLVKMLS   120
ADSANEVSTA SASGASYATS TSSAVSSSQA TGYSTAAGYG NAAGAGAGAA AAVS        174

SEQ ID NO: 87            moltype = AA   length = 174
FEATURE                  Location/Qualifiers
source                   1..174
                         mol_type = protein
                         organism = synthetic construct
SEQUENCE: 87
GQKIWTNPDA AMAMTNNLVQ CAGRSGALTA DQMDDLGMVS DSVNSQVRKM GANAPPHKIK    60
AMSTAVAAGV AEVVASSPPQ SYSAVLNTIG GCLRESMMQV TGSVDNTFTT EMMQMVNMFA   120
ADNANEVSAS ASGSGASYAT GTSSAVSTSQ ATGYSTAGGY GTAAGAGAGA AAAA        174

SEQ ID NO: 88            moltype = AA   length = 174
FEATURE                  Location/Qualifiers
source                   1..174
                         mol_type = protein
                         organism = synthetic construct
SEQUENCE: 88
GSGYGAGAGA GAGSGYGAGA GAGSGYGAGA GAGAGSGYVA GAGAGAGAGS GYGAGAGAGA    60
GSSYSAGAGA GAGSGYGAGS SASAGSGAVST QTVSSSATTS SQSAAAATGA AYGTRASTGS   120
GASAGAAASG AGAGYGGQAG YGQGGGAAAY RAGAGSQAAY GQGASGSSGA AAAA        174

SEQ ID NO: 89            moltype = AA   length = 171
FEATURE                  Location/Qualifiers
source                   1..171
                         mol_type = protein
                         organism = synthetic construct
SEQUENCE: 89
GGQGGRGGFG GLSSQGAGGA GQGGSGAAAA AAAAGGDGGS GLGDYGAGRG YGAGLGGAGG    60
AGVASAAASA AASRLSSPSA ASRVSSAVTS LISGGGPTNP AALSNTFSNV VYQISVSSPG   120
LSGCDVLIQA LLELVSALVH ILGSAIIGQV NSSAAGESAS LVGQSVYQAF S           171

SEQ ID NO: 90            moltype = AA   length = 169
FEATURE                  Location/Qualifiers
source                   1..169
                         mol_type = protein
                         organism = synthetic construct
SEQUENCE: 90
GVGQAATPWE NSQLAEDFIN SFLRFIAQSG AFSPNQLDDM SSIGDTLKTA IEKMAQSRKS    60
SKSKLQALNM AFASSMAEIA VAEQGGLSLE AKTNAIANAL ASAFLETTGF VNQQFVSEIK   120
SLIYMIAQAS SNEISGSAAA AGGGSGGGGG SGQGGYGQGA SASASAAAA              169

SEQ ID NO: 91            moltype = AA   length = 169
FEATURE                  Location/Qualifiers
source                   1..169
                         mol_type = protein
                         organism = synthetic construct
```

```
SEQUENCE: 91
GGGDGYGQGG YGNQRGVGSY GQGAGAGAAA TSAAGGAGSG RGGYGEQGGL GGYGQGAGAG      60
AASTAAGGGD GYGQGGYGNQ GGRGSYGQGS GAGAGAAVAA AAGGAVSGQG GYDGEGGQGG     120
YGQGSGAGAA VAAASGGTGA GQGGYGSQGS QAGYGQGAGF RAAAATAAA                 169

SEQ ID NO: 92           moltype = AA   length = 168
FEATURE                 Location/Qualifiers
source                  1..168
                        mol_type = protein
                        organism = synthetic construct
SEQUENCE: 92
GAGAGYGGQV GYGQGAGASA GAAAAGAGAG YGGQAGYGQG AGGSAGAAAA GAGAGRQAGY      60
GQGAGASARA AAAAGAGTGYG QGAGASAGAA AAGAGAGSQV GYGQGAGASS GAAAAAGAGA    120
GYGGQVGYEQ GAGASAGAEA AASSAGAGYG GQAGYGQGAG ASAGAAAA                 168

SEQ ID NO: 93           moltype = AA   length = 166
FEATURE                 Location/Qualifiers
source                  1..166
                        mol_type = protein
                        organism = synthetic construct
SEQUENCE: 93
GGAGQGGYGG LGGQGAGQGG LGGQRAGAAA AAAGGAGQGG YGGLGSQGAG RGGYGGVGSG      60
ASAASAAASR LSSPEASSRV SSAVSNLVSS GPTNSAALSS TISNVVSQIS ASNPGLSGCD    120
VLVQALLEVV SALIQILGSS SIGQVNYGTA GQAAQIVGQS VYQALG                  166

SEQ ID NO: 94           moltype = AA   length = 166
FEATURE                 Location/Qualifiers
source                  1..166
                        mol_type = protein
                        organism = synthetic construct
SEQUENCE: 94
GGYGPGSGQQ GPGGAGQQGP GGQGPYGPGS SSAAAVGGYG PSSGLQGPAG QGPYGPGAAA      60
SAAAAAGASR LSSPQASSRV SSAVSSLVSS GPTNSAALTN TISSVVSQIS ASNPGLSGCD    120
VLIQALLEIV SALVHILGYS SIGQINYDAA AQYASLVGQS VAQALA                  166

SEQ ID NO: 95           moltype = AA   length = 166
FEATURE                 Location/Qualifiers
source                  1..166
                        mol_type = protein
                        organism = synthetic construct
SEQUENCE: 95
GGAGAGQGSY GGQGGYGQGG AGAATATAAA AGGAGSGQGG YGGQGGLGGY GQGAGAGAAA      60
AAAAAGGAG AGQGGYGGQG GQGGYGQGAG AGAAAAAAGG AGAGQGGYGG QGGYGQGGGA     120
GAAAAAAAS GGSGSGQGGY GGQGGLGGYG QGAGAGAGAA ASAAAA                  166

SEQ ID NO: 96           moltype = AA   length = 165
FEATURE                 Location/Qualifiers
source                  1..165
                        mol_type = protein
                        organism = synthetic construct
SEQUENCE: 96
GQGGQGGYGR QSQGAGSAAA AAAAAAAAAA AGSGQGGYGG QGGYGQGSS ASASAAASAA      60
STVANSVSRL SSPSAVSRVS SAVSSLVSNG QVNMAALPNI ISNISSSVSA SAPGASGCEV    120
IVQALLEVIT ALVQIVSSSS VGYINPSAVN QITNVVANAM AQVMG                 165

SEQ ID NO: 97           moltype = AA   length = 164
FEATURE                 Location/Qualifiers
source                  1..164
                        mol_type = protein
                        organism = synthetic construct
SEQUENCE: 97
GGAGQGGYGG LGGQGSGAAA AGTGQGGYGS LGGQGAGAAG AAAAAVGGAG QGGYGGVGSA      60
AASAAASRLS SPEASSRVSS AVSNLVSSGP TNSAALSNTI SNVVSQISSS NPGLSGCDVL    120
VQALLEVVSA LIHILGSSSI GQVNYGSAGQ ATQIVGQSVY QALG                  164

SEQ ID NO: 98           moltype = AA   length = 164
FEATURE                 Location/Qualifiers
source                  1..164
                        mol_type = protein
                        organism = synthetic construct
SEQUENCE: 98
GAGAGGAGGY GAGQGYGAGA GAGAAAGAGA GGARGYGARQ GYGSGAGAGA GARAGGAGGY      60
GRGAGAGAAA ASGAGAGGYG AGQGYGAGAG AVASAAAGAG SGAGGAGGYG RGAGAVAGAG    120
AGGAGGYGAG AGAAAGVGAG GSSGGYGGRQG GYSAGAGAGA AAAA                 164

SEQ ID NO: 99           moltype = AA   length = 163
FEATURE                 Location/Qualifiers
source                  1..163
                        mol_type = protein
```

-continued

```
                            organism = synthetic construct
SEQUENCE: 99
GQGGQGGYGG LGQGGYGQGA GSSAAAAAAA AAAAGRGQGG YGQGSGGNAA AAAAAAAAAA        60
SGQGGQGGGG GQGQGGYGQG AGSSAAAAAA AAAAAAAAAG RGQGGYGQGA GGNAAAAAAA       120
AAAAASGQGG QGGQGGGQGG GYGQGAGSSA AAAAAAAAAA AAA                        163

SEQ ID NO: 100          moltype = AA  length = 162
FEATURE                 Location/Qualifiers
source                  1..162
                        mol_type = protein
                        organism = synthetic construct
SEQUENCE: 100
GGYGPGSGQQ GPGQQGPGQQ GPGQQGPYGA GASAAAAAAG GYGPGSGQQG PGVRVAAPVA        60
SAAASRLSSS AASSRVSSAV SSLVSSGPTT PAALSNTISS AVSQISASNP GLSGCDVLVQ       120
ALLEVVSALV HILGSSSVGQ INYGASAQYA QMVGQSVTQA LV                         162

SEQ ID NO: 101          moltype = AA  length = 161
FEATURE                 Location/Qualifiers
source                  1..161
                        mol_type = protein
                        organism = synthetic construct
SEQUENCE: 101
GAGAGGAGYG RGAGAGAGAA AGAGAGAAAG AGAGAGGYGG QGGYGAGAGA GAAAAGAGA         60
GGAAGYSRGG RAGAAGAGAG AAAAGAGAGAG GYGQGGYGA GAGAGAAAAA GAGSGGAGGY       120
GRGAGAGAAA GAGAAAGAGA GAGGYGGQGG YGAGAGAAAA A                          161

SEQ ID NO: 102          moltype = AA  length = 160
FEATURE                 Location/Qualifiers
source                  1..160
                        mol_type = protein
                        organism = synthetic construct
SEQUENCE: 102
GAGAGRGGYG RGAGAGGYGG QGGYGAGAGA GAAAAGAGA GGYGDKEIAC WSRCRYTVAS         60
TTSRLSSAEA SSRISSAAST LVSGGYLNTA ALPSVISDLF AQVGASSPGV SDSEVLIQVL       120
LEIVSSLIHI LSSSSVGQVD FSSVGSSAAA VGQSMQVVMG                            160

SEQ ID NO: 103          moltype = AA  length = 160
FEATURE                 Location/Qualifiers
source                  1..160
                        mol_type = protein
                        organism = synthetic construct
SEQUENCE: 103
GAGAGAGGAG GYGRGAGAGA GAGAGAAAGQ GYGSGAGAGA GASAGGAGSY GRGAGAGAAA        60
ASGAGAGGYG AGQGYGAGAG AVASAAAGAG SGAGGAGGYG RGAVAGSGAG AGAGAGGAGG       120
YGAGAGAGAA AGAVAGGSGG YGGRQGGYSA GAGAGAAAAA                            160

SEQ ID NO: 104          moltype = AA  length = 159
FEATURE                 Location/Qualifiers
source                  1..159
                        mol_type = protein
                        organism = synthetic construct
SEQUENCE: 104
GPGGYGPVQQ GPSGPGSAAG PGGYGPAQQG PARYGPGSAA AAAAAAGSAG YGPGPQASAA        60
ASRLASPDSG ARVASAVSNL VSSGPTSSAA LSSVISNAVS QIGASNPGLS GCDVLIQALL       120
EIVSACVTIL SSSSIGQVNY GAASQFAQVV GQSVLSAFS                             159

SEQ ID NO: 105          moltype = AA  length = 156
FEATURE                 Location/Qualifiers
source                  1..156
                        mol_type = protein
                        organism = synthetic construct
SEQUENCE: 105
GTGGVGGLFL SSGDFGRGGA GAGAGAAAAS AAAASSAAAG ARGGSGFGVG TGGFGRGGAG        60
AGTGAAAASA AAASAAAAGA GGDGGLFLSS GDFGRGGAGA GAGAAAASAA AASSAAAGAR       120
GGSGFGVGTG GFGRGGAGDG ASAAAASAAA ASAAAA                                156

SEQ ID NO: 106          moltype = AA  length = 153
FEATURE                 Location/Qualifiers
source                  1..153
                        mol_type = protein
                        organism = synthetic construct
SEQUENCE: 106
GGYGPGAGQQ GPGGAGQQGP GGQGPYGPSV AAAAASAAGG YGPGAGQQGP ASAAVSRLSS        60
PQASSRVSSA VSSLVSSGPT NPAALSNAMS SVVSQVSASN PGLSGCDVLV QALLEIVSAL       120
VHILGSSSIG QINYAASSQY AQMVGQSVAQ ALA                                   153

SEQ ID NO: 107          moltype = AA  length = 153
FEATURE                 Location/Qualifiers
source                  1..153
```

```
                         mol_type = protein
                         organism = synthetic construct
SEQUENCE: 107
GGAGQGGYGG  LGSQGAGRGG  YGGQGAGAAA  AATGGAGQGG  YGGVGSGASA  ASAAASRLSS   60
PQASSRVSSA  VSNLVASGPT  NSAALSSTIS  NAVSQIGASN  PGLSGCDVLI  QALLEVVSAL  120
IHILGSSSIG  QVNYGSAGQA  TQIVGQSVYQ  ALG                                 153

SEQ ID NO: 108           moltype = AA  length = 153
FEATURE                  Location/Qualifiers
source                   1..153
                         mol_type = protein
                         organism = synthetic construct
SEQUENCE: 108
GGAGQGGYGG  LGSQGAGRGG  YGGQGAGAAV  AAIGGVGQGG  YGGVGSGASA  ASAAASRLSS   60
PEASSRVSSA  VSNLVSSGPT  NSAALSSTIS  NVVSQIGASN  PGLSGCDVLI  QALLEVVSAL  120
VHILGSSSIG  QVNYGSAGQA  TQIVGQSVYQ  ALG                                 153

SEQ ID NO: 109           moltype = AA  length = 152
FEATURE                  Location/Qualifiers
source                   1..152
                         mol_type = protein
                         organism = synthetic construct
SEQUENCE: 109
GASGGYGGGA  GEGAGAAAAA  GAGAGGAGGY  GGGAGSGAGA  VARAGAGGAG  GYGSGIGGGY   60
GSGAGAAAGA  GAGGAGAYGG  GYGTGAGAGA  RGADSAGAAA  GYGGGVGTGT  GSSAGYGRGA  120
GAGAGAGAAA  GSGAGAAGGY  GGGYGAGAGA  GA                                  152

SEQ ID NO: 110           moltype = AA  length = 152
FEATURE                  Location/Qualifiers
source                   1..152
                         mol_type = protein
                         organism = synthetic construct
SEQUENCE: 110
GAGSGQGGYG  GQGGLGGYGQ  GAGAGAAAGA  SGSGSGGAGQ  GGLGGYGQGS  GAGAAAAGAA   60
ASGAGQGGFG  PYGSSYQSST  SYSVTSQGAA  GGLGGYGQGS  GAGAAAAGAA  GQGGQGGYGQ  120
GAGAGAGAGA  GQGGLGGYGQ  GAGSSAASAA  AA                                  152

SEQ ID NO: 111           moltype = AA  length = 151
FEATURE                  Location/Qualifiers
source                   1..151
                         mol_type = protein
                         organism = synthetic construct
SEQUENCE: 111
GGAGQGGYGG  LGGQGVGRGG  LGGQGAGAAA  AGGAGQGGYG  GVGSGASAAS  AAASRLSSPQ   60
ASSRLSSAVS  NLVATGPTNS  AALSSTISNV  VSQIGASNPG  LSGCDVLIQA  LLEVVSALIQ  120
ILGSSSIGQV  NYGSAGQATQ  IVGQSVYQAL  G                                   151

SEQ ID NO: 112           moltype = AA  length = 150
FEATURE                  Location/Qualifiers
source                   1..150
                         mol_type = protein
                         organism = synthetic construct
SEQUENCE: 112
GAGSGGAGGY  GRGAGAGAGA  AAGAGAGAGS  YGGQGGYGAG  AGAGAAAAAG  AGAGAGGYGR   60
GAGAGAGAGA  GAAARAGAGA  GGAGYGGQGG  YGAGAGAGAA  AAAGAGAGGA  GGYGRGAGAG  120
AGAAAGAGAG  AGGYGGQSGY  GAGAGAAAAA                                      150

SEQ ID NO: 113           moltype = AA  length = 150
FEATURE                  Location/Qualifiers
source                   1..150
                         mol_type = protein
                         organism = synthetic construct
SEQUENCE: 113
GASGAGQGQG  YGQQGQGGSS  AAAAAAAAAA  AQGQGQGYGQ  QGQGYGQQGQ  GGSSAAAAAA   60
AAAAAAAQGQ  GQGYGQQGQG  SAAAAAAAAA  GASGAGQGQG  YGQQGQGGSS  AAAAAAAAAA  120
AAAAAQGQGY  GQQGQGSAAA  AAAAAAAAAA                                      150

SEQ ID NO: 114           moltype = AA  length = 945
FEATURE                  Location/Qualifiers
source                   1..945
                         mol_type = protein
                         organism = synthetic construct
SEQUENCE: 114
GGYGPGAGQQ  GPGSGGQQGP  GGQGPYGSGQ  QGPGGAGQQG  PGGQGPYGPG  AAAAAAAAG    60
GYGPGAGQQG  PGGAGQQGPG  SQGPGGQGPY  GPGAGQQGPG  SQGPGSGGQQ  GPGGQGPYGP  120
SAAAAAAAAG  GGYGPGAGQR  SQGPGGQGPY  GPGAGQQGPG  SQGPGSGGQQ  GPGGQGPYGP  180
SAAAAAAAAG  GYGPGAGQQG  PGSQGPGSGG  QQGPGGQGPY  GPGAAAAAAA  VGGYGPGAGQ  240
QGPGSQGPGS  GQQGPGGQQG  PYGPSAAAAA  AAAGGYGPGA  GQQGPGSQGP  GSGGQQGPGG  300
QGPYGPSAAA  AAAAGGYGP   GAGQQGPGSG  GQQGPGGQPY  YGSGQQGPGG  AGQQGPGGQG  360
```

```
PYGPGAAAAA AAAAGGYGPG AGQQGPGGAG QQGPGPYGPG QQGPGPSQGPG    420
SGGQQGPGGQ GPYGPSAAAA AAAAAGGYGP GAGQRSQGPG GQGPYGPGAG QQGPGPSQGPG    480
SGGQQGPGGQ GPYGPSAAAA AAAAAGGYGPG AGQQGPGSQG PGSGGQQGPG GQGPYGPGAA    540
AAAAAVGGYG PGAGQQGPGS QGPGSGGQQG PGGQGPYGPS AAAAAAAAGG YGPGAGQQGP    600
GSQGPGSGGQ QGPGGAGQPYG PSAAAAAAAA GGYGPGAGQQGP GGQGPYGSGQ    660
QGPGGAGQQG PGGQGPYGPG AAAAAAAAAG GYGPGAGQQG PGGAGQQGPG SQGPGGGPY    720
GPGAGQQGPG SQGPGSGGQQ GPGGQGPYGP SAAAAAAAAA GGYGPGAGQR SQGPGGGPY    780
GPGAGQQGPG SQGPGSGGQQ GPGGQGPYGP SAAAAAAAAG GYGPGAGQQG PGSQGPGSGG    840
QQGPGGGPY GPGAAAAAAA VGGYGPGAGQ QGPGSQGPGS GGQQGPGGQ PYGPSAAAAA    900
AAAAGGYGPGA GQQGPGSQGP GSGGQQGPGG QGPYGPSAAA AAAAA    945

SEQ ID NO: 115              moltype = AA    length = 89
FEATURE                     Location/Qualifiers
source                      1..89
                            mol_type = protein
                            organism = synthetic construct
SEQUENCE: 115
MRFPSIFTAV LFAASSALAA PVNTTTEDET AQIPAEAVIG YLDLEGDFDV AVLPFSNSTN    60
NGLLFINTTI ASIAAKEEGV SLDKREAEA                                     89

SEQ ID NO: 116              moltype = AA    length = 48
FEATURE                     Location/Qualifiers
source                      1..48
                            mol_type = protein
                            organism = Saccharomyces cerevisiae
SEQUENCE: 116
MEGGEEEVER IPDELFDTKK KHLLDKLIRV GIILVLLIWG TVLLLKSI                 48

SEQ ID NO: 117              moltype = AA    length = 43
FEATURE                     Location/Qualifiers
source                      1..43
                            mol_type = protein
                            organism = Saccharomyces cerevisiae
SEQUENCE: 117
MFFNRLSAGK LLVPLSVVLY ALFVVILPLQ NSFHSSNVLV RGA                      43

SEQ ID NO: 118              moltype = AA    length = 26
FEATURE                     Location/Qualifiers
source                      1..26
                            mol_type = protein
                            organism = Saccharomyces cerevisiae
SEQUENCE: 118
MPFGIDNTDF TVLAGLVLAV LLYVKR                                         26

SEQ ID NO: 119              moltype = AA    length = 17
FEATURE                     Location/Qualifiers
source                      1..17
                            mol_type = protein
                            organism = Saccharomyces cerevisiae
SEQUENCE: 119
MKPQCILISL LVNLAYA                                                   17

SEQ ID NO: 120              moltype = AA    length = 24
FEATURE                     Location/Qualifiers
source                      1..24
                            mol_type = protein
                            organism = Saccharomyces cerevisiae
SEQUENCE: 120
MISANSLLIS TLCAFAIATP LSKR                                           24

SEQ ID NO: 121              moltype = AA    length = 19
FEATURE                     Location/Qualifiers
source                      1..19
                            mol_type = protein
                            organism = Saccharomyces cerevisiae
SEQUENCE: 121
MLQSVVFFAL LTFASSVSA                                                 19

SEQ ID NO: 122              moltype = AA    length = 21
FEATURE                     Location/Qualifiers
source                      1..21
                            mol_type = protein
                            organism = Rattus norvegicus
SEQUENCE: 122
MRLAVVCLCL FGLASCLPVK V                                              21

SEQ ID NO: 123              moltype = AA    length = 31
FEATURE                     Location/Qualifiers
source                      1..31
```

```
                            mol_type = protein
                            organism = Pichia pastoris
SEQUENCE: 123
MLSLKPSWLT LAALMYAMLL VVVPFAKPVR A                                       31

SEQ ID NO: 124              moltype = AA  length = 23
FEATURE                     Location/Qualifiers
source                      1..23
                            mol_type = protein
                            organism = Pichia pastoris
SEQUENCE: 124
MSFSSNVPQL FLLLVLLTNI VSG                                                23

SEQ ID NO: 125              moltype = AA  length = 16
FEATURE                     Location/Qualifiers
source                      1..16
                            mol_type = protein
                            organism = Pichia pastoris
SEQUENCE: 125
MNLYLITLLF ASLCSA                                                        16

SEQ ID NO: 126              moltype = AA  length = 19
FEATURE                     Location/Qualifiers
source                      1..19
                            mol_type = protein
                            organism = Saccharomyces cerevisiae
SEQUENCE: 126
MHWAAAVAIF FIVVTKFLQ                                                     19

SEQ ID NO: 127              moltype = AA  length = 18
FEATURE                     Location/Qualifiers
source                      1..18
                            mol_type = protein
                            organism = Pichia pastoris
SEQUENCE: 127
MRFSNFLTVS ALLTGALG                                                      18

SEQ ID NO: 128              moltype = AA  length = 20
FEATURE                     Location/Qualifiers
source                      1..20
                            mol_type = protein
                            organism = Saccharomyces cerevisiae
SEQUENCE: 128
MSLLYIILLF TQFLLLPTDA                                                    20

SEQ ID NO: 129              moltype = AA  length = 44
FEATURE                     Location/Qualifiers
source                      1..44
                            mol_type = protein
                            organism = Pichia pastoris
SEQUENCE: 129
MAKADGSLLY YNPHNPPRRY YFYMAIFAVS VICVLYGPSQ QLSS                         44

SEQ ID NO: 130              moltype = AA  length = 90
FEATURE                     Location/Qualifiers
source                      1..90
                            mol_type = protein
                            organism = synthetic construct
SEQUENCE: 130
MKLSTNLILA IAAASAVVSA APVNTTTEDE TAQIPAEAVI GYSDLEGDFD VAVLPFSNST         60
NNGLLFINTT IASIAAKEEG VSLEKREAEA                                         90

SEQ ID NO: 131              moltype = AA  length = 118
FEATURE                     Location/Qualifiers
source                      1..118
                            mol_type = protein
                            organism = synthetic construct
SEQUENCE: 131
MEGGEEEVER IPDELFDTKK KHLLDKLIRV GIILVLLIWG TVLLLKSIAP VNTTTEDETA         60
QIPAEAVIGY SDLEGDFDVA VLPFSNSTNN GLLFINTTIA SIAAKEEGVS LEKREAEA         118

SEQ ID NO: 132              moltype = AA  length = 113
FEATURE                     Location/Qualifiers
source                      1..113
                            mol_type = protein
                            organism = synthetic construct
SEQUENCE: 132
MFFNRLSAGK LLVPLSVVLY ALFVVILPLQ NSFHSSNVLV RGAAPVNTTT EDETAQIPAE         60
AVIGYSDLEG DFDVAVLPFS NSTNNGLLFI NTTIASIAAK EEGVSLEKRE AEA              113
```

SEQ ID NO: 133          moltype = AA   length = 96
FEATURE                 Location/Qualifiers
source                  1..96
                        mol_type = protein
                        organism = synthetic construct
SEQUENCE: 133
MPFGIDNTDF TVLAGLVLAV LLYVKRAPVN TTTEDETAQI PAEAVIGYSD LEGDFDVAVL    60
PFSNSTNNGL LFINTTIASI AAKEEGVSLE KREAEA                              96

SEQ ID NO: 134          moltype = AA   length = 87
FEATURE                 Location/Qualifiers
source                  1..87
                        mol_type = protein
                        organism = synthetic construct
SEQUENCE: 134
MKPQCILISL LVNLAYAAPV NTTTEDETAQ IPAEAVIGYS DLEGDFDVAV LPFSNSTNNG    60
LLFINTTIAS IAAKEEGVSL EKREAEA                                        87

SEQ ID NO: 135          moltype = AA   length = 94
FEATURE                 Location/Qualifiers
source                  1..94
                        mol_type = protein
                        organism = synthetic construct
SEQUENCE: 135
MISANSLLIS TLCAFAIATP LSKRAPVNTT TEDETAQIPA EAVIGYSDLE GDFDVAVLPF    60
SNSTNNGLLF INTTIASIAA KEEGVSLEKR EAEA                                94

SEQ ID NO: 136          moltype = AA   length = 89
FEATURE                 Location/Qualifiers
source                  1..89
                        mol_type = protein
                        organism = synthetic construct
SEQUENCE: 136
MLQSVVFFAL LTFASSVSAA PVNTTTEDET AQIPAEAVIG YSDLEGDFDV AVLPFSNSTN    60
NGLLFINTTI ASIAAKEEGV SLEKREAEA                                      89

SEQ ID NO: 137          moltype = AA   length = 91
FEATURE                 Location/Qualifiers
source                  1..91
                        mol_type = protein
                        organism = synthetic construct
SEQUENCE: 137
MRLAVVCLCL FGLASCLPVK VAPVNTTTED ETAQIPAEAV IGYSDLEGDF DVAVLPFSNS    60
TNNGLLFINT TIASIAAKEE GVSLEKREAE A                                   91

SEQ ID NO: 138          moltype = AA   length = 101
FEATURE                 Location/Qualifiers
source                  1..101
                        mol_type = protein
                        organism = synthetic construct
SEQUENCE: 138
MLSLKPSWLT LAALMYAMLL VVVPFAKPVR AAPVNTTTED ETAQIPAEAV IGYSDLEGDF    60
DVAVLPFSNS TNNGLLFINT TIASIAAKEE GVSLEKREAE A                       101

SEQ ID NO: 139          moltype = AA   length = 93
FEATURE                 Location/Qualifiers
source                  1..93
                        mol_type = protein
                        organism = synthetic construct
SEQUENCE: 139
MSFSSNVPQL FLLLVLLTNI VSGAPVNTTT EDETAQIPAE AVIGYSDLEG DFDVAVLPFS    60
NSTNNGLLFI NTTIASIAAK EEGVSLEKRE AEA                                 93

SEQ ID NO: 140          moltype = AA   length = 86
FEATURE                 Location/Qualifiers
source                  1..86
                        mol_type = protein
                        organism = synthetic construct
SEQUENCE: 140
MNLYLITLLF ASLCSAAPVN TTTEDETAQI PAEAVIGYSD LEGDFDVAVL PFSNSTNNGL    60
LFINTTIASI AAKEEGVSLE KREAEA                                         86

SEQ ID NO: 141          moltype = AA   length = 89
FEATURE                 Location/Qualifiers
source                  1..89
                        mol_type = protein
                        organism = synthetic construct
SEQUENCE: 141

```
MHWAAAVAIF FIVVTKFLQA PVNTTTEDET AQIPAEAVIG YSDLEGDFDV AVLPFSNSTN    60
NGLLFINTTI ASIAAKEEGV SLEKREAEA                                      89

SEQ ID NO: 142          moltype = AA  length = 88
FEATURE                 Location/Qualifiers
source                  1..88
                        mol_type = protein
                        organism = synthetic construct
SEQUENCE: 142
MRFSNFLTVS ALLTGALGAP VNTTTEDETA QIPAEAVIGY SDLEGDFDVA VLPFSNSTNN    60
GLLFINTTIA SIAAKEEGVS LEKREAEA                                       88

SEQ ID NO: 143          moltype = AA  length = 90
FEATURE                 Location/Qualifiers
source                  1..90
                        mol_type = protein
                        organism = synthetic construct
SEQUENCE: 143
MSLLYIILLF TQFLLLPTDA APVNTTTEDE TAQIPAEAVI GYSDLEGDFD VAVLPFSNST    60
NNGLLFINTT IASIAAKEEG VSLEKREAEA                                     90

SEQ ID NO: 144          moltype = AA  length = 37
FEATURE                 Location/Qualifiers
source                  1..37
                        mol_type = protein
                        organism = synthetic construct
SEQUENCE: 144
APVAPAEEAA NHLHKRAYYT DTTKTHTFTE VVTVYRT                              37

SEQ ID NO: 145          moltype = AA  length = 483
FEATURE                 Location/Qualifiers
source                  1..483
                        mol_type = protein
                        organism = synthetic construct
SEQUENCE: 145
ANLNGTLMQY FEWYMPNDGQ HWKRLQNDSA YLAEHGITAV WIPPAYKGTS QDDVGYGAYD    60
LYDLGEFHQK GTVRTKYGTK GELQSAINSL HSRDINVYGD VVINHKGGAD ATEDVTAVEV   120
DPADRNRVTS GEQRIKAWTH FQFPGRGSTY SDFKWHWYHF DGTDWDESRK LNRIYKFQGK   180
AWDWEVSNVN GNYDYLMYAD IDYDHPDATA EIKRWGTWYA NELQLDGFRL DAVKHIKFSF   240
LRDWVNHVRE KTGKEMFTVA EYWQNDLGAL ENYLNKTNFN HSVFDVPLHY QFHAASTQGG   300
GYDMRKLLNG TVVSKHPVKA VTFVDNHDTQ PGQSLESTVQ TWFKPLAYAF ILTREAGYPQ   360
IFYGDMYGTK GASQREIPAL KHKIEPILKA RIQYAYGAQH DYFDHHDIVG WTREGDSSVA   420
NSGLAALITD GPGGTKRMYV GRQNAGETWH DITGNRSDSV VINAEGWGEF HVNGGSVSIY   480
VQR                                                                  483

SEQ ID NO: 146          moltype = AA  length = 235
FEATURE                 Location/Qualifiers
source                  1..235
                        mol_type = protein
                        organism = synthetic construct
SEQUENCE: 146
TALTEGAKLF EKEIPYITEL EGDVEGMKFI IKGEGTGDAT TGTIKAKYIC TTGDLPVPWA    60
TLVSTLSYGV QCFAKYPSHI KDFFKSAMPE GYTQERTISF EGDGVYKTRA MVTYERGSIY   120
NRVTLTGENF KKDGHILRKN VAFQCPPSIL YILPDTVNNG IRVEFNQAYD IEGVTEKLVT   180
KCSQMNRPLA GSAAVHIPRY HHITYHTKLS KDRDERRDHM CLVEVVKAVD LDTYQ         235

SEQ ID NO: 147          moltype = AA  length = 64
FEATURE                 Location/Qualifiers
VARIANT                 4..8
                        note = This region may encompass "SGGQQ," "GAGQQ," "GQGPY,"
                        "AGQQ" or "SQ," wherein some positions may be absent
VARIANT                 12..16
                        note = This region may encompass "SGGQQ," "GAGQQ," "GQGPY,"
                        "AGQQ" or "SQ," wherein some positions may be absent
VARIANT                 20..24
                        note = This region may encompass "SGGQQ," "GAGQQ," "GQGPY,"
                        "AGQQ" or "SQ," wherein some positions may be absent
VARIANT                 28..32
                        note = This region may encompass "SGGQQ," "GAGQQ," "GQGPY,"
                        "AGQQ" or "SQ," wherein some positions may be absent
VARIANT                 36..40
                        note = This region may encompass "SGGQQ," "GAGQQ," "GQGPY,"
                        "AGQQ" or "SQ," wherein some positions may be absent
VARIANT                 44..48
                        note = This region may encompass "SGGQQ," "GAGQQ," "GQGPY,"
                        "AGQQ" or "SQ," wherein some positions may be absent
VARIANT                 52..56
                        note = This region may encompass "SGGQQ," "GAGQQ," "GQGPY,"
                        "AGQQ" or "SQ," wherein some positions may be absent
```

```
VARIANT              60..64
                     note = This region may encompass "SGGQQ," "GAGQQ," "GQGPY,"
                     "AGQQ" or "SQ," wherein some positions may be absent
VARIANT              1..64
                     note = This region may encompass 4-8 "GPG-X1" repeating
                     units, wherein X1 is "SGGQQ," "GAGQQ," "GQGPY," "AGQQ" or
                     "SQ," and some positions may be absent
source               1..64
                     mol_type = protein
                     organism = synthetic construct
SEQUENCE: 147
GPGXXXXXGP GXXXXXGPGX XXXXGPGXXX XXGPGXXXXX GPGXXXXXGP GXXXXXGPGX   60
XXXX                                                                64

SEQ ID NO: 148       moltype = AA  length = 20
FEATURE              Location/Qualifiers
VARIANT              1..20
                     note = This sequence may encompass 6-20 residues
source               1..20
                     mol_type = protein
                     organism = synthetic construct
SEQUENCE: 148
AAAAAAAAAA AAAAAAAAAA                                               20

SEQ ID NO: 149       moltype = AA  length = 1800
FEATURE              Location/Qualifiers
VARIANT              7..11
                     note = This region may encompass "SGGQQ," "GAGQQ," "GQGPY,"
                     "AGQQ" or "SQ," wherein some positions may be absent
VARIANT              15..19
                     note = This region may encompass "SGGQQ," "GAGQQ," "GQGPY,"
                     "AGQQ" or "SQ," wherein some positions may be absent
VARIANT              23..27
                     note = This region may encompass "SGGQQ," "GAGQQ," "GQGPY,"
                     "AGQQ" or "SQ," wherein some positions may be absent
VARIANT              31..35
                     note = This region may encompass "SGGQQ," "GAGQQ," "GQGPY,"
                     "AGQQ" or "SQ," wherein some positions may be absent
VARIANT              39..43
                     note = This region may encompass "SGGQQ," "GAGQQ," "GQGPY,"
                     "AGQQ" or "SQ," wherein some positions may be absent
VARIANT              47..51
                     note = This region may encompass "SGGQQ," "GAGQQ," "GQGPY,"
                     "AGQQ" or "SQ," wherein some positions may be absent
VARIANT              55..59
                     note = This region may encompass "SGGQQ," "GAGQQ," "GQGPY,"
                     "AGQQ" or "SQ," wherein some positions may be absent
VARIANT              63..67
                     note = This region may encompass "SGGQQ," "GAGQQ," "GQGPY,"
                     "AGQQ" or "SQ," wherein some positions may be absent
VARIANT              4..67
                     note = This region may encompass 4-8 repeating "GPG-X1"
                     repeating units, wherein X1 is "SGGQQ," "GAGQQ," "GQGPY,"
                     "AGQQ" or "SQ," and some positions may be absent
VARIANT              71..90
                     note = This region may encompass 6-20 residues
VARIANT              97..101
                     note = This region may encompass "SGGQQ," "GAGQQ," "GQGPY,"
                     "AGQQ" or "SQ," wherein some positions may be absent
VARIANT              105..109
                     note = This region may encompass "SGGQQ," "GAGQQ," "GQGPY,"
                     "AGQQ" or "SQ," wherein some positions may be absent
VARIANT              113..117
                     note = This region may encompass "SGGQQ," "GAGQQ," "GQGPY,"
                     "AGQQ" or "SQ," wherein some positions may be absent
VARIANT              121..125
                     note = This region may encompass "SGGQQ," "GAGQQ," "GQGPY,"
                     "AGQQ" or "SQ," wherein some positions may be absent
VARIANT              129..133
                     note = This region may encompass "SGGQQ," "GAGQQ," "GQGPY,"
                     "AGQQ" or "SQ," wherein some positions may be absent
VARIANT              137..141
                     note = This region may encompass "SGGQQ," "GAGQQ," "GQGPY,"
                     "AGQQ" or "SQ," wherein some positions may be absent
VARIANT              145..149
                     note = This region may encompass "SGGQQ," "GAGQQ," "GQGPY,"
                     "AGQQ" or "SQ," wherein some positions may be absent
VARIANT              153..157
                     note = This region may encompass "SGGQQ," "GAGQQ," "GQGPY,"
```

```
                    -continued

VARIANT         94..157
                note = This region may encompass 4-8 repeating "GPG-X1"
                repeating units, wherein X1 is "SGGQQ," "GAGQQ," "GQGPY,"
                "AGQQ" or "SQ," and some positions may be absent
VARIANT         161..180
                note = This region may encompass 6-20 residues
VARIANT         187..191
                note = This region may encompass "SGGQQ," "GAGQQ," "GQGPY,"
                "AGQQ" or "SQ," wherein some positions may be absent
VARIANT         195..199
                note = This region may encompass "SGGQQ," "GAGQQ," "GQGPY,"
                "AGQQ" or "SQ," wherein some positions may be absent
VARIANT         203..207
                note = This region may encompass "SGGQQ," "GAGQQ," "GQGPY,"
                "AGQQ" or "SQ," wherein some positions may be absent
VARIANT         211..215
                note = This region may encompass "SGGQQ," "GAGQQ," "GQGPY,"
                "AGQQ" or "SQ," wherein some positions may be absent
VARIANT         219..223
                note = This region may encompass "SGGQQ," "GAGQQ," "GQGPY,"
                "AGQQ" or "SQ," wherein some positions may be absent
VARIANT         227..231
                note = This region may encompass "SGGQQ," "GAGQQ," "GQGPY,"
                "AGQQ" or "SQ," wherein some positions may be absent
VARIANT         235..239
                note = This region may encompass "SGGQQ," "GAGQQ," "GQGPY,"
                "AGQQ" or "SQ," wherein some positions may be absent
VARIANT         243..247
                note = This region may encompass "SGGQQ," "GAGQQ," "GQGPY,"
                "AGQQ" or "SQ," wherein some positions may be absent
VARIANT         184..247
                note = This region may encompass 4-8 repeating "GPG-X1"
                repeating units, wherein X1 is "SGGQQ," "GAGQQ," "GQGPY,"
                "AGQQ" or "SQ," and some positions may be absent
VARIANT         251..270
                note = This region may encompass 6-20 residues
VARIANT         277..281
                note = This region may encompass "SGGQQ," "GAGQQ," "GQGPY,"
                "AGQQ" or "SQ," wherein some positions may be absent
VARIANT         285..289
                note = This region may encompass "SGGQQ," "GAGQQ," "GQGPY,"
                "AGQQ" or "SQ," wherein some positions may be absent
VARIANT         293..297
                note = This region may encompass "SGGQQ," "GAGQQ," "GQGPY,"
                "AGQQ" or "SQ," wherein some positions may be absent
VARIANT         301..305
                note = This region may encompass "SGGQQ," "GAGQQ," "GQGPY,"
                "AGQQ" or "SQ," wherein some positions may be absent
VARIANT         309..313
                note = This region may encompass "SGGQQ," "GAGQQ," "GQGPY,"
                "AGQQ" or "SQ," wherein some positions may be absent
VARIANT         317..321
                note = This region may encompass "SGGQQ," "GAGQQ," "GQGPY,"
                "AGQQ" or "SQ," wherein some positions may be absent
VARIANT         325..329
                note = This region may encompass "SGGQQ," "GAGQQ," "GQGPY,"
                "AGQQ" or "SQ," wherein some positions may be absent
VARIANT         333..337
                note = This region may encompass "SGGQQ," "GAGQQ," "GQGPY,"
                "AGQQ" or "SQ," wherein some positions may be absent
VARIANT         274..337
                note = This region may encompass 4-8 repeating "GPG-X1"
                repeating units, wherein X1 is "SGGQQ," "GAGQQ," "GQGPY,"
                "AGQQ" or "SQ," and some positions may be absent
VARIANT         341..360
                note = This region may encompass 6-20 residues
VARIANT         367..371
                note = This region may encompass "SGGQQ," "GAGQQ," "GQGPY,"
                "AGQQ" or "SQ," wherein some positions may be absent
VARIANT         375..379
                note = This region may encompass "SGGQQ," "GAGQQ," "GQGPY,"
                "AGQQ" or "SQ," wherein some positions may be absent
VARIANT         383..387
                note = This region may encompass "SGGQQ," "GAGQQ," "GQGPY,"
                "AGQQ" or "SQ," wherein some positions may be absent
VARIANT         391..395
                note = This region may encompass "SGGQQ," "GAGQQ," "GQGPY,"
                "AGQQ" or "SQ," wherein some positions may be absent
```

-continued

| | |
|---|---|
| VARIANT | 399..403<br>note = This region may encompass "SGGQQ," "GAGQQ," "GQGPY,"<br>"AGQQ" or "SQ," wherein some positions may be absent |
| VARIANT | 407..411<br>note = This region may encompass "SGGQQ," "GAGQQ," "GQGPY,"<br>"AGQQ" or "SQ," wherein some positions may be absent |
| VARIANT | 415..419<br>note = This region may encompass "SGGQQ," "GAGQQ," "GQGPY,"<br>"AGQQ" or "SQ," wherein some positions may be absent |
| VARIANT | 423..427<br>note = This region may encompass "SGGQQ," "GAGQQ," "GQGPY,"<br>"AGQQ" or "SQ," wherein some positions may be absent |
| VARIANT | 364..427<br>note = This region may encompass 4-8 repeating "GPG-X1"<br>repeating units, wherein X1 is "SGGQQ," "GAGQQ," "GQGPY,"<br>"AGQQ" or "SQ," and some positions may be absent |
| VARIANT | 431..450<br>note = This region may encompass 6-20 residues |
| VARIANT | 457..461<br>note = This region may encompass "SGGQQ," "GAGQQ," "GQGPY,"<br>"AGQQ" or "SQ," wherein some positions may be absent |
| VARIANT | 465..469<br>note = This region may encompass "SGGQQ," "GAGQQ," "GQGPY,"<br>"AGQQ" or "SQ," wherein some positions may be absent |
| VARIANT | 473..477<br>note = This region may encompass "SGGQQ," "GAGQQ," "GQGPY,"<br>"AGQQ" or "SQ," wherein some positions may be absent |
| VARIANT | 481..485<br>note = This region may encompass "SGGQQ," "GAGQQ," "GQGPY,"<br>"AGQQ" or "SQ," wherein some positions may be absent |
| VARIANT | 489..493<br>note = This region may encompass "SGGQQ," "GAGQQ," "GQGPY,"<br>"AGQQ" or "SQ," wherein some positions may be absent |
| VARIANT | 497..501<br>note = This region may encompass "SGGQQ," "GAGQQ," "GQGPY,"<br>"AGQQ" or "SQ," wherein some positions may be absent |
| VARIANT | 505..509<br>note = This region may encompass "SGGQQ," "GAGQQ," "GQGPY,"<br>"AGQQ" or "SQ," wherein some positions may be absent |
| VARIANT | 513..517<br>note = This region may encompass "SGGQQ," "GAGQQ," "GQGPY,"<br>"AGQQ" or "SQ," wherein some positions may be absent |
| VARIANT | 454..517<br>note = This region may encompass 4-8 repeating "GPG-X1"<br>repeating units, wherein X1 is "SGGQQ," "GAGQQ," "GQGPY,"<br>"AGQQ" or "SQ," and some positions may be absent |
| VARIANT | 521..540<br>note = This region may encompass 6-20 residues |
| VARIANT | 547..551<br>note = This region may encompass "SGGQQ," "GAGQQ," "GQGPY,"<br>"AGQQ" or "SQ," wherein some positions may be absent |
| VARIANT | 555..559<br>note = This region may encompass "SGGQQ," "GAGQQ," "GQGPY,"<br>"AGQQ" or "SQ," wherein some positions may be absent |
| VARIANT | 563..567<br>note = This region may encompass "SGGQQ," "GAGQQ," "GQGPY,"<br>"AGQQ" or "SQ," wherein some positions may be absent |
| VARIANT | 571..575<br>note = This region may encompass "SGGQQ," "GAGQQ," "GQGPY,"<br>"AGQQ" or "SQ," wherein some positions may be absent |
| VARIANT | 579..583<br>note = This region may encompass "SGGQQ," "GAGQQ," "GQGPY,"<br>"AGQQ" or "SQ," wherein some positions may be absent |
| VARIANT | 587..591<br>note = This region may encompass "SGGQQ," "GAGQQ," "GQGPY,"<br>"AGQQ" or "SQ," wherein some positions may be absent |
| VARIANT | 595..599<br>note = This region may encompass "SGGQQ," "GAGQQ," "GQGPY,"<br>"AGQQ" or "SQ," wherein some positions may be absent |
| VARIANT | 603..607<br>note = This region may encompass "SGGQQ," "GAGQQ," "GQGPY,"<br>"AGQQ" or "SQ," wherein some positions may be absent |
| VARIANT | 544..607<br>note = This region may encompass 4-8 repeating "GPG-X1"<br>repeating units, wherein X1 is "SGGQQ," "GAGQQ," "GQGPY,"<br>"AGQQ" or "SQ," and some positions may be absent |
| VARIANT | 611..630<br>note = This region may encompass 6-20 residues |
| VARIANT | 637..641 |

|         |                                                                                                                                                                                                     |
|---------|-----------------------------------------------------------------------------------------------------------------------------------------------------------------------------------------------------|
|         | note = This region may encompass "SGGQQ," "GAGQQ," "GQGPY," "AGQQ" or "SQ," wherein some positions may be absent                                                                                    |
| VARIANT | 645..649                                                                                                                                                                                            |
|         | note = This region may encompass "SGGQQ," "GAGQQ," "GQGPY," "AGQQ" or "SQ," wherein some positions may be absent                                                                                    |
| VARIANT | 653..657                                                                                                                                                                                            |
|         | note = This region may encompass "SGGQQ," "GAGQQ," "GQGPY," "AGQQ" or "SQ," wherein some positions may be absent                                                                                    |
| VARIANT | 661..665                                                                                                                                                                                            |
|         | note = This region may encompass "SGGQQ," "GAGQQ," "GQGPY," "AGQQ" or "SQ," wherein some positions may be absent                                                                                    |
| VARIANT | 669..673                                                                                                                                                                                            |
|         | note = This region may encompass "SGGQQ," "GAGQQ," "GQGPY," "AGQQ" or "SQ," wherein some positions may be absent                                                                                    |
| VARIANT | 677..681                                                                                                                                                                                            |
|         | note = This region may encompass "SGGQQ," "GAGQQ," "GQGPY," "AGQQ" or "SQ," wherein some positions may be absent                                                                                    |
| VARIANT | 685..689                                                                                                                                                                                            |
|         | note = This region may encompass "SGGQQ," "GAGQQ," "GQGPY," "AGQQ" or "SQ," wherein some positions may be absent                                                                                    |
| VARIANT | 693..697                                                                                                                                                                                            |
|         | note = This region may encompass "SGGQQ," "GAGQQ," "GQGPY," "AGQQ" or "SQ," wherein some positions may be absent                                                                                    |
| VARIANT | 634..697                                                                                                                                                                                            |
|         | note = This region may encompass 4-8 repeating "GPG-X1" repeating units, wherein X1 is "SGGQQ," "GAGQQ," "GQGPY," "AGQQ" or "SQ," and some positions may be absent                                  |
| VARIANT | 701..720                                                                                                                                                                                            |
|         | note = This region may encompass 6-20 residues                                                                                                                                                      |
| VARIANT | 727..731                                                                                                                                                                                            |
|         | note = This region may encompass "SGGQQ," "GAGQQ," "GQGPY," "AGQQ" or "SQ," wherein some positions may be absent                                                                                    |
| VARIANT | 735..739                                                                                                                                                                                            |
|         | note = This region may encompass "SGGQQ," "GAGQQ," "GQGPY," "AGQQ" or "SQ," wherein some positions may be absent                                                                                    |
| VARIANT | 743..747                                                                                                                                                                                            |
|         | note = This region may encompass "SGGQQ," "GAGQQ," "GQGPY," "AGQQ" or "SQ," wherein some positions may be absent                                                                                    |
| VARIANT | 751..755                                                                                                                                                                                            |
|         | note = This region may encompass "SGGQQ," "GAGQQ," "GQGPY," "AGQQ" or "SQ," wherein some positions may be absent                                                                                    |
| VARIANT | 759..763                                                                                                                                                                                            |
|         | note = This region may encompass "SGGQQ," "GAGQQ," "GQGPY," "AGQQ" or "SQ," wherein some positions may be absent                                                                                    |
| VARIANT | 767..771                                                                                                                                                                                            |
|         | note = This region may encompass "SGGQQ," "GAGQQ," "GQGPY," "AGQQ" or "SQ," wherein some positions may be absent                                                                                    |
| VARIANT | 775..779                                                                                                                                                                                            |
|         | note = This region may encompass "SGGQQ," "GAGQQ," "GQGPY," "AGQQ" or "SQ," wherein some positions may be absent                                                                                    |
| VARIANT | 783..787                                                                                                                                                                                            |
|         | note = This region may encompass "SGGQQ," "GAGQQ," "GQGPY," "AGQQ" or "SQ," wherein some positions may be absent                                                                                    |
| VARIANT | 724..787                                                                                                                                                                                            |
|         | note = This region may encompass 4-8 repeating "GPG-X1" repeating units, wherein X1 is "SGGQQ," "GAGQQ," "GQGPY," "AGQQ" or "SQ," and some positions may be absent                                  |
| VARIANT | 791..810                                                                                                                                                                                            |
|         | note = This region may encompass 6-20 residues                                                                                                                                                      |
| VARIANT | 817..821                                                                                                                                                                                            |
|         | note = This region may encompass "SGGQQ," "GAGQQ," "GQGPY," "AGQQ" or "SQ," wherein some positions may be absent                                                                                    |
| VARIANT | 825..829                                                                                                                                                                                            |
|         | note = This region may encompass "SGGQQ," "GAGQQ," "GQGPY," "AGQQ" or "SQ," wherein some positions may be absent                                                                                    |
| VARIANT | 833..837                                                                                                                                                                                            |
|         | note = This region may encompass "SGGQQ," "GAGQQ," "GQGPY," "AGQQ" or "SQ," wherein some positions may be absent                                                                                    |
| VARIANT | 841..845                                                                                                                                                                                            |
|         | note = This region may encompass "SGGQQ," "GAGQQ," "GQGPY," "AGQQ" or "SQ," wherein some positions may be absent                                                                                    |
| VARIANT | 849..853                                                                                                                                                                                            |
|         | note = This region may encompass "SGGQQ," "GAGQQ," "GQGPY," "AGQQ" or "SQ," wherein some positions may be absent                                                                                    |
| VARIANT | 857..861                                                                                                                                                                                            |
|         | note = This region may encompass "SGGQQ," "GAGQQ," "GQGPY," "AGQQ" or "SQ," wherein some positions may be absent                                                                                    |
| VARIANT | 865..869                                                                                                                                                                                            |
|         | note = This region may encompass "SGGQQ," "GAGQQ," "GQGPY,"                                                                                                                                         |

-continued

```
                        "AGQQ" or "SQ," wherein some positions may be absent
VARIANT                 873..877
                        note = This region may encompass "SGGQQ," "GAGQQ," "GQGPY,"
                        "AGQQ" or "SQ," wherein some positions may be absent
VARIANT                 814..877
                        note = This region may encompass 4-8 repeating "GPG-X1"
                        repeating units, wherein X1 is "SGGQQ," "GAGQQ," "GQGPY,"
                        "AGQQ" or "SQ," and some positions may be absent
VARIANT                 881..900
                        note = This region may encompass 6-20 residues
VARIANT                 907..911
                        note = This region may encompass "SGGQQ," "GAGQQ," "GQGPY,"
                        "AGQQ" or "SQ," wherein some positions may be absent
VARIANT                 915..919
                        note = This region may encompass "SGGQQ," "GAGQQ," "GQGPY,"
                        "AGQQ" or "SQ," wherein some positions may be absent
VARIANT                 923..927
                        note = This region may encompass "SGGQQ," "GAGQQ," "GQGPY,"
                        "AGQQ" or "SQ," wherein some positions may be absent
VARIANT                 931..935
                        note = This region may encompass "SGGQQ," "GAGQQ," "GQGPY,"
                        "AGQQ" or "SQ," wherein some positions may be absent
VARIANT                 939..943
                        note = This region may encompass "SGGQQ," "GAGQQ," "GQGPY,"
                        "AGQQ" or "SQ," wherein some positions may be absent
VARIANT                 947..951
                        note = This region may encompass "SGGQQ," "GAGQQ," "GQGPY,"
                        "AGQQ" or "SQ," wherein some positions may be absent
VARIANT                 955..959
                        note = This region may encompass "SGGQQ," "GAGQQ," "GQGPY,"
                        "AGQQ" or "SQ," wherein some positions may be absent
VARIANT                 963..967
                        note = This region may encompass "SGGQQ," "GAGQQ," "GQGPY,"
                        "AGQQ" or "SQ," wherein some positions may be absent
VARIANT                 904..967
                        note = This region may encompass 4-8 repeating "GPG-X1"
                        repeating units, wherein X1 is "SGGQQ," "GAGQQ," "GQGPY,"
                        "AGQQ" or "SQ," and some positions may be absent
VARIANT                 971..990
                        note = This region may encompass 6-20 residues
VARIANT                 997..1001
                        note = This region may encompass "SGGQQ," "GAGQQ," "GQGPY,"
                        "AGQQ" or "SQ," wherein some positions may be absent
VARIANT                 1005..1009
                        note = This region may encompass "SGGQQ," "GAGQQ," "GQGPY,"
                        "AGQQ" or "SQ," wherein some positions may be absent
VARIANT                 1013..1017
                        note = This region may encompass "SGGQQ," "GAGQQ," "GQGPY,"
                        "AGQQ" or "SQ," wherein some positions may be absent
VARIANT                 1021..1025
                        note = This region may encompass "SGGQQ," "GAGQQ," "GQGPY,"
                        "AGQQ" or "SQ," wherein some positions may be absent
VARIANT                 1029..1033
                        note = This region may encompass "SGGQQ," "GAGQQ," "GQGPY,"
                        "AGQQ" or "SQ," wherein some positions may be absent
VARIANT                 1037..1041
                        note = This region may encompass "SGGQQ," "GAGQQ," "GQGPY,"
                        "AGQQ" or "SQ," wherein some positions may be absent
VARIANT                 1045..1049
                        note = This region may encompass "SGGQQ," "GAGQQ," "GQGPY,"
                        "AGQQ" or "SQ," wherein some positions may be absent
VARIANT                 1053..1057
                        note = This region may encompass "SGGQQ," "GAGQQ," "GQGPY,"
                        "AGQQ" or "SQ," wherein some positions may be absent
VARIANT                 994..1057
                        note = This region may encompass 4-8 repeating "GPG-X1"
                        repeating units, wherein X1 is "SGGQQ," "GAGQQ," "GQGPY,"
                        "AGQQ" or "SQ," and some positions may be absent
VARIANT                 1061..1080
                        note = This region may encompass 6-20 residues
VARIANT                 1087..1091
                        note = This region may encompass "SGGQQ," "GAGQQ," "GQGPY,"
                        "AGQQ" or "SQ," wherein some positions may be absent
VARIANT                 1095..1099
                        note = This region may encompass "SGGQQ," "GAGQQ," "GQGPY,"
                        "AGQQ" or "SQ," wherein some positions may be absent
VARIANT                 1103..1107
                        note = This region may encompass "SGGQQ," "GAGQQ," "GQGPY,"
                        "AGQQ" or "SQ," wherein some positions may be absent
```

-continued

| | |
|---|---|
| VARIANT | 1111..1115<br>note = This region may encompass "SGGQQ," "GAGQQ," "GQGPY,"<br>"AGQQ" or "SQ," wherein some positions may be absent |
| VARIANT | 1119..1123<br>note = This region may encompass "SGGQQ," "GAGQQ," "GQGPY,"<br>"AGQQ" or "SQ," wherein some positions may be absent |
| VARIANT | 1127..1131<br>note = This region may encompass "SGGQQ," "GAGQQ," "GQGPY,"<br>"AGQQ" or "SQ," wherein some positions may be absent |
| VARIANT | 1135..1139<br>note = This region may encompass "SGGQQ," "GAGQQ," "GQGPY,"<br>"AGQQ" or "SQ," wherein some positions may be absent |
| VARIANT | 1143..1147<br>note = This region may encompass "SGGQQ," "GAGQQ," "GQGPY,"<br>"AGQQ" or "SQ," wherein some positions may be absent |
| VARIANT | 1084..1147<br>note = This region may encompass 4-8 repeating "GPG-X1"<br>repeating units, wherein X1 is "SGGQQ," "GAGQQ," "GQGPY,"<br>"AGQQ" or "SQ," and some positions may be absent |
| VARIANT | 1151..1170<br>note = This region may encompass 6-20 residues |
| VARIANT | 1177..1181<br>note = This region may encompass "SGGQQ," "GAGQQ," "GQGPY,"<br>"AGQQ" or "SQ," wherein some positions may be absent |
| VARIANT | 1185..1189<br>note = This region may encompass "SGGQQ," "GAGQQ," "GQGPY,"<br>"AGQQ" or "SQ," wherein some positions may be absent |
| VARIANT | 1193..1197<br>note = This region may encompass "SGGQQ," "GAGQQ," "GQGPY,"<br>"AGQQ" or "SQ," wherein some positions may be absent |
| VARIANT | 1201..1205<br>note = This region may encompass "SGGQQ," "GAGQQ," "GQGPY,"<br>"AGQQ" or "SQ," wherein some positions may be absent |
| VARIANT | 1209..1213<br>note = This region may encompass "SGGQQ," "GAGQQ," "GQGPY,"<br>"AGQQ" or "SQ," wherein some positions may be absent |
| VARIANT | 1217..1221<br>note = This region may encompass "SGGQQ," "GAGQQ," "GQGPY,"<br>"AGQQ" or "SQ," wherein some positions may be absent |
| VARIANT | 1225..1229<br>note = This region may encompass "SGGQQ," "GAGQQ," "GQGPY,"<br>"AGQQ" or "SQ," wherein some positions may be absent |
| VARIANT | 1233..1237<br>note = This region may encompass "SGGQQ," "GAGQQ," "GQGPY,"<br>"AGQQ" or "SQ," wherein some positions may be absent |
| VARIANT | 1174..1237<br>note = This region may encompass 4-8 repeating "GPG-X1"<br>repeating units, wherein X1 is "SGGQQ," "GAGQQ," "GQGPY,"<br>"AGQQ" or "SQ," and some positions may be absent |
| VARIANT | 1241..1260<br>note = This region may encompass 6-20 residues |
| VARIANT | 1267..1271<br>note = This region may encompass "SGGQQ," "GAGQQ," "GQGPY,"<br>"AGQQ" or "SQ," wherein some positions may be absent |
| VARIANT | 1275..1279<br>note = This region may encompass "SGGQQ," "GAGQQ," "GQGPY,"<br>"AGQQ" or "SQ," wherein some positions may be absent |
| VARIANT | 1283..1287<br>note = This region may encompass "SGGQQ," "GAGQQ," "GQGPY,"<br>"AGQQ" or "SQ," wherein some positions may be absent |
| VARIANT | 1291..1295<br>note = This region may encompass "SGGQQ," "GAGQQ," "GQGPY,"<br>"AGQQ" or "SQ," wherein some positions may be absent |
| VARIANT | 1299..1303<br>note = This region may encompass "SGGQQ," "GAGQQ," "GQGPY,"<br>"AGQQ" or "SQ," wherein some positions may be absent |
| VARIANT | 1307..1311<br>note = This region may encompass "SGGQQ," "GAGQQ," "GQGPY,"<br>"AGQQ" or "SQ," wherein some positions may be absent |
| VARIANT | 1315..1319<br>note = This region may encompass "SGGQQ," "GAGQQ," "GQGPY,"<br>"AGQQ" or "SQ," wherein some positions may be absent |
| VARIANT | 1323..1327<br>note = This region may encompass "SGGQQ," "GAGQQ," "GQGPY,"<br>"AGQQ" or "SQ," wherein some positions may be absent |
| VARIANT | 1264..1327<br>note = This region may encompass 4-8 repeating "GPG-X1"<br>repeating units, wherein X1 is "SGGQQ," "GAGQQ," "GQGPY,"<br>"AGQQ" or "SQ," and some positions may be absent |

-continued

| | |
|---|---|
| VARIANT | 1331..1350<br>note = This region may encompass 6-20 residues |
| VARIANT | 1357..1361<br>note = This region may encompass "SGGQQ," "GAGQQ," "GQGPY,"<br>"AGQQ" or "SQ," wherein some positions may be absent |
| VARIANT | 1365..1369<br>note = This region may encompass "SGGQQ," "GAGQQ," "GQGPY,"<br>"AGQQ" or "SQ," wherein some positions may be absent |
| VARIANT | 1373..1377<br>note = This region may encompass "SGGQQ," "GAGQQ," "GQGPY,"<br>"AGQQ" or "SQ," wherein some positions may be absent |
| VARIANT | 1381..1385<br>note = This region may encompass "SGGQQ," "GAGQQ," "GQGPY,"<br>"AGQQ" or "SQ," wherein some positions may be absent |
| VARIANT | 1389..1393<br>note = This region may encompass "SGGQQ," "GAGQQ," "GQGPY,"<br>"AGQQ" or "SQ," wherein some positions may be absent |
| VARIANT | 1397..1401<br>note = This region may encompass "SGGQQ," "GAGQQ," "GQGPY,"<br>"AGQQ" or "SQ," wherein some positions may be absent |
| VARIANT | 1405..1409<br>note = This region may encompass "SGGQQ," "GAGQQ," "GQGPY,"<br>"AGQQ" or "SQ," wherein some positions may be absent |
| VARIANT | 1413..1417<br>note = This region may encompass "SGGQQ," "GAGQQ," "GQGPY,"<br>"AGQQ" or "SQ," wherein some positions may be absent |
| VARIANT | 1354..1417<br>note = This region may encompass 4-8 repeating "GPG-X1"<br>repeating units, wherein X1 is "SGGQQ," "GAGQQ," "GQGPY,"<br>"AGQQ" or "SQ," and some positions may be absent |
| VARIANT | 1421..1440<br>note = This region may encompass 6-20 residues |
| VARIANT | 1447..1451<br>note = This region may encompass "SGGQQ," "GAGQQ," "GQGPY,"<br>"AGQQ" or "SQ," wherein some positions may be absent |
| VARIANT | 1455..1459<br>note = This region may encompass "SGGQQ," "GAGQQ," "GQGPY,"<br>"AGQQ" or "SQ," wherein some positions may be absent |
| VARIANT | 1463..1467<br>note = This region may encompass "SGGQQ," "GAGQQ," "GQGPY,"<br>"AGQQ" or "SQ," wherein some positions may be absent |
| VARIANT | 1471..1475<br>note = This region may encompass "SGGQQ," "GAGQQ," "GQGPY,"<br>"AGQQ" or "SQ," wherein some positions may be absent |
| VARIANT | 1479..1483<br>note = This region may encompass "SGGQQ," "GAGQQ," "GQGPY,"<br>"AGQQ" or "SQ," wherein some positions may be absent |
| VARIANT | 1487..1491<br>note = This region may encompass "SGGQQ," "GAGQQ," "GQGPY,"<br>"AGQQ" or "SQ," wherein some positions may be absent |
| VARIANT | 1495..1499<br>note = This region may encompass "SGGQQ," "GAGQQ," "GQGPY,"<br>"AGQQ" or "SQ," wherein some positions may be absent |
| VARIANT | 1503..1507<br>note = This region may encompass "SGGQQ," "GAGQQ," "GQGPY,"<br>"AGQQ" or "SQ," wherein some positions may be absent |
| VARIANT | 1444..1507<br>note = This region may encompass 4-8 repeating "GPG-X1"<br>repeating units, wherein X1 is "SGGQQ," "GAGQQ," "GQGPY,"<br>"AGQQ" or "SQ," and some positions may be absent |
| VARIANT | 1511..1530<br>note = This region may encompass 6-20 residues |
| VARIANT | 1537..1541<br>note = This region may encompass "SGGQQ," "GAGQQ," "GQGPY,"<br>"AGQQ" or "SQ," wherein some positions may be absent |
| VARIANT | 1545..1549<br>note = This region may encompass "SGGQQ," "GAGQQ," "GQGPY,"<br>"AGQQ" or "SQ," wherein some positions may be absent |
| VARIANT | 1553..1557<br>note = This region may encompass "SGGQQ," "GAGQQ," "GQGPY,"<br>"AGQQ" or "SQ," wherein some positions may be absent |
| VARIANT | 1561..1565<br>note = This region may encompass "SGGQQ," "GAGQQ," "GQGPY,"<br>"AGQQ" or "SQ," wherein some positions may be absent |
| VARIANT | 1569..1573<br>note = This region may encompass "SGGQQ," "GAGQQ," "GQGPY,"<br>"AGQQ" or "SQ," wherein some positions may be absent |
| VARIANT | 1577..1581<br>note = This region may encompass "SGGQQ," "GAGQQ," "GQGPY," |

```
VARIANT         1585..1589
                "AGQQ" or "SQ," wherein some positions may be absent
                note = This region may encompass "SGGQQ," "GAGQQ," "GQGPY,"
                "AGQQ" or "SQ," wherein some positions may be absent
VARIANT         1593..1597
                note = This region may encompass "SGGQQ," "GAGQQ," "GQGPY,"
                "AGQQ" or "SQ," wherein some positions may be absent
VARIANT         1534..1597
                note = This region may encompass 4-8 repeating "GPG-X1"
                repeating units, wherein X1 is "SGGQQ," "GAGQQ," "GQGPY,"
                "AGQQ" or "SQ," and some positions may be absent
VARIANT         1601..1620
                note = This region may encompass 6-20 residues
VARIANT         1627..1631
                note = This region may encompass "SGGQQ," "GAGQQ," "GQGPY,"
                "AGQQ" or "SQ," wherein some positions may be absent
VARIANT         1635..1639
                note = This region may encompass "SGGQQ," "GAGQQ," "GQGPY,"
                "AGQQ" or "SQ," wherein some positions may be absent
VARIANT         1643..1647
                note = This region may encompass "SGGQQ," "GAGQQ," "GQGPY,"
                "AGQQ" or "SQ," wherein some positions may be absent
VARIANT         1651..1655
                note = This region may encompass "SGGQQ," "GAGQQ," "GQGPY,"
                "AGQQ" or "SQ," wherein some positions may be absent
VARIANT         1659..1663
                note = This region may encompass "SGGQQ," "GAGQQ," "GQGPY,"
                "AGQQ" or "SQ," wherein some positions may be absent
VARIANT         1667..1671
                note = This region may encompass "SGGQQ," "GAGQQ," "GQGPY,"
                "AGQQ" or "SQ," wherein some positions may be absent
VARIANT         1675..1679
                note = This region may encompass "SGGQQ," "GAGQQ," "GQGPY,"
                "AGQQ" or "SQ," wherein some positions may be absent
VARIANT         1683..1687
                note = This region may encompass "SGGQQ," "GAGQQ," "GQGPY,"
                "AGQQ" or "SQ," wherein some positions may be absent
VARIANT         1624..1687
                note = This region may encompass 4-8 repeating "GPG-X1"
                repeating units, wherein X1 is "SGGQQ," "GAGQQ," "GQGPY,"
                "AGQQ" or "SQ," and some positions may be absent
VARIANT         1691..1710
                note = This region may encompass 6-20 residues
VARIANT         1717..1721
                note = This region may encompass "SGGQQ," "GAGQQ," "GQGPY,"
                "AGQQ" or "SQ," wherein some positions may be absent
VARIANT         1725..1729
                note = This region may encompass "SGGQQ," "GAGQQ," "GQGPY,"
                "AGQQ" or "SQ," wherein some positions may be absent
VARIANT         1733..1737
                note = This region may encompass "SGGQQ," "GAGQQ," "GQGPY,"
                "AGQQ" or "SQ," wherein some positions may be absent
VARIANT         1741..1745
                note = This region may encompass "SGGQQ," "GAGQQ," "GQGPY,"
                "AGQQ" or "SQ," wherein some positions may be absent
VARIANT         1749..1753
                note = This region may encompass "SGGQQ," "GAGQQ," "GQGPY,"
                "AGQQ" or "SQ," wherein some positions may be absent
VARIANT         1757..1761
                note = This region may encompass "SGGQQ," "GAGQQ," "GQGPY,"
                "AGQQ" or "SQ," wherein some positions may be absent
VARIANT         1765..1769
                note = This region may encompass "SGGQQ," "GAGQQ," "GQGPY,"
                "AGQQ" or "SQ," wherein some positions may be absent
VARIANT         1773..1777
                note = This region may encompass "SGGQQ," "GAGQQ," "GQGPY,"
                "AGQQ" or "SQ," wherein some positions may be absent
VARIANT         1714..1777
                note = This region may encompass 4-8 repeating "GPG-X1"
                repeating units, wherein X1 is "SGGQQ," "GAGQQ," "GQGPY,"
                "AGQQ" or "SQ," and some positions may be absent
VARIANT         1781..1800
                note = This region may encompass 6-20 residues
VARIANT         1..1800
                note = This sequence may encompass 2-20
                "GGY-[GPG-X1]n1-GPS-(A)n2" repeating units, wherein X1 is
                "SGGQQ," "GAGQQ," "GQGPY," "AGQQ" or "SQ," n1 is 4-8 and
                n2 is 6-20 and some positions may be absent
source          1..1800
```

```
                    mol_type = protein
                    organism = synthetic construct
SEQUENCE: 149
GGYGPGXXXX XGPGXXXXXG PGXXXXXGPG XXXXXGPGXX XXXGPGXXXX XGPGXXXXXG    60
PGXXXXXGPS AAAAAAAAAA AAAAAAAAAA GGYGPGXXXX XGPGXXXXXG PGXXXXXGPG   120
XXXXXGPGXX XXXGPGXXXX XGPGXXXXXG PGXXXXXGPS AAAAAAAAAA AAAAAAAAAA   180
GGYGPGXXXX XGPGXXXXXG PGXXXXXGPG XXXXXGPGXX XXXGPGXXXX XGPGXXXXXG   240
PGXXXXXGPS AAAAAAAAAA AAAAAAAAAA GGYGPGXXXX XGPGXXXXXG PGXXXXXGPG   300
XXXXXGPGXX XXXGPGXXXX XGPGXXXXXG PGXXXXXGPS AAAAAAAAAA AAAAAAAAAA   360
GGYGPGXXXX XGPGXXXXXG PGXXXXXGPG XXXXXGPGXX XXXGPGXXXX XGPGXXXXXG   420
PGXXXXXGPS AAAAAAAAAA AAAAAAAAAA GGYGPGXXXX XGPGXXXXXG PGXXXXXGPG   480
XXXXXGPGXX XXXGPGXXXX XGPGXXXXXG PGXXXXXGPS AAAAAAAAAA AAAAAAAAAA   540
GGYGPGXXXX XGPGXXXXXG PGXXXXXGPG XXXXXGPGXX XXXGPGXXXX XGPGXXXXXG   600
PGXXXXXGPS AAAAAAAAAA AAAAAAAAAA GGYGPGXXXX XGPGXXXXXG PGXXXXXGPG   660
XXXXXGPGXX XXXGPGXXXX XGPGXXXXXG PGXXXXXGPS AAAAAAAAAA AAAAAAAAAA   720
GGYGPGXXXX XGPGXXXXXG PGXXXXXGPG XXXXXGPGXX XXXGPGXXXX XGPGXXXXXG   780
PGXXXXXGPS AAAAAAAAAA AAAAAAAAAA GGYGPGXXXX XGPGXXXXXG PGXXXXXGPG   840
XXXXXGPGXX XXXGPGXXXX XGPGXXXXXG PGXXXXXGPS AAAAAAAAAA AAAAAAAAAA   900
GGYGPGXXXX XGPGXXXXXG PGXXXXXGPG XXXXXGPGXX XXXGPGXXXX XGPGXXXXXG   960
PGXXXXXGPS AAAAAAAAAA AAAAAAAAAA GGYGPGXXXX XGPGXXXXXG PGXXXXXGPG  1020
XXXXXGPGXX XXXGPGXXXX XGPGXXXXXG PGXXXXXGPS AAAAAAAAAA AAAAAAAAAA  1080
GGYGPGXXXX XGPGXXXXXG PGXXXXXGPG XXXXXGPGXX XXXGPGXXXX XGPGXXXXXG  1140
PGXXXXXGPS AAAAAAAAAA AAAAAAAAAA GGYGPGXXXX XGPGXXXXXG PGXXXXXGPG  1200
XXXXXGPGXX XXXGPGXXXX XGPGXXXXXG PGXXXXXGPS AAAAAAAAAA AAAAAAAAAA  1260
GGYGPGXXXX XGPGXXXXXG PGXXXXXGPG XXXXXGPGXX XXXGPGXXXX XGPGXXXXXG  1320
PGXXXXXGPS AAAAAAAAAA AAAAAAAAAA GGYGPGXXXX XGPGXXXXXG PGXXXXXGPG  1380
XXXXXGPGXX XXXGPGXXXX XGPGXXXXXG PGXXXXXGPS AAAAAAAAAA AAAAAAAAAA  1440
GGYGPGXXXX XGPGXXXXXG PGXXXXXGPG XXXXXGPGXX XXXGPGXXXX XGPGXXXXXG  1500
PGXXXXXGPS AAAAAAAAAA AAAAAAAAAA GGYGPGXXXX XGPGXXXXXG PGXXXXXGPG  1560
XXXXXGPGXX XXXGPGXXXX XGPGXXXXXG PGXXXXXGPS AAAAAAAAAA AAAAAAAAAA  1620
GGYGPGXXXX XGPGXXXXXG PGXXXXXGPG XXXXXGPGXX XXXGPGXXXX XGPGXXXXXG  1680
PGXXXXXGPS AAAAAAAAAA AAAAAAAAAA GGYGPGXXXX XGPGXXXXXG PGXXXXXGPG  1740
XXXXXGPGXX XXXGPGXXXX XGPGXXXXXG PGXXXXXGPS AAAAAAAAAA AAAAAAAAAA  1800

SEQ ID NO: 150           moltype = AA  length = 5
FEATURE                  Location/Qualifiers
source                   1..5
                         mol_type = protein
                         organism = synthetic construct
SEQUENCE: 150
SGGQQ                                                                 5

SEQ ID NO: 151           moltype = AA  length = 5
FEATURE                  Location/Qualifiers
source                   1..5
                         mol_type = protein
                         organism = synthetic construct
SEQUENCE: 151
GAGQQ                                                                 5

SEQ ID NO: 152           moltype = AA  length = 5
FEATURE                  Location/Qualifiers
source                   1..5
                         mol_type = protein
                         organism = synthetic construct
SEQUENCE: 152
GQGPY                                                                 5

SEQ ID NO: 153           moltype = AA  length = 4
FEATURE                  Location/Qualifiers
source                   1..4
                         mol_type = protein
                         organism = synthetic construct
SEQUENCE: 153
AGQQ                                                                  4

SEQ ID NO: 154           moltype = AA  length = 8
FEATURE                  Location/Qualifiers
VARIANT                  1..8
                         note = This sequence may encompass 6-8 residues
source                   1..8
                         mol_type = protein
                         organism = synthetic construct
SEQUENCE: 154
HHHHHHHH                                                              8
```

What is claimed is:

1. An expression construct comprising a polynucleotide sequence that encodes a protein operably linked to a recombinant secretion signal, wherein said recombinant secretion signal comprises a leader peptide comprising the amino acid sequence of SEQ ID NO: 1 or SEQ ID NO: 2 and a signal peptide comprising the amino acid sequence of SEQ ID NO: 127.

2. The expression construct of claim 1, wherein said construct comprises multiple copies of the polynucleotide sequence.

3. The expression construct of claim 1, wherein said polynucleotide sequence is operably linked to the pGCW14 promoter of *Pichia pastoris* or the pGAP promoter of *Pichia pastoris*.

4. The expression construct of claim 1, wherein said protein is a silk protein.

5. The expression construct of claim 4, wherein said protein comprises SEQ ID NO: 17.

6. The expression construct of claim 4, wherein said protein comprises multiple copies of SEQ ID NO: 17.

7. A recombinant vector comprising the expression construct of claim 1.

8. The recombinant vector of claim 7, wherein said vector comprises multiple copies of said expression construct.

9. The recombinant vector of claim 7, wherein said vector comprises a *Pichia* autonomously replicating sequence.

10. A recombinant host cell comprising an expression construct comprising a polynucleotide sequence that encodes a protein operably linked to a recombinant secretion signal, wherein said recombinant secretion signal comprises a leader peptide comprising the amino acid sequence of SEQ ID NO: 1 or SEQ ID NO: 2 and a signal peptide comprising the amino acid sequence of SEQ ID NO: 127.

11. The recombinant host cell of claim 10, wherein said recombinant host cell is a yeast cell.

12. The recombinant host cell of claim 11, wherein said recombinant host cell is a methylotrophic yeast cell.

13. The recombinant host cell of claim 12, wherein said recombinant host cell is *Pichia pastoris*.

14. The recombinant host cell of claim 10, wherein said expression construct is stably integrated within the genome of said recombinant host cell.

15. The recombinant host cell of claim 10, wherein said expression construct is maintained extrachromosomally in said recombinant host cell.

16. A composition comprising the recombinant host cell of claim 10 and a culture medium.

17. A method for producing a protein, comprising the steps of:
   a) culturing the recombinant host cell of claim 10 in a culture medium; and
   b) extracting said protein from the culture medium.

* * * * *